US007601341B2

(12) United States Patent
Rosenblum

(10) Patent No.: US 7,601,341 B2
(45) Date of Patent: Oct. 13, 2009

(54) VASCULAR ENDOTHELIAL GROWTH FACTOR FUSION CONSTRUCTS USED TO INHIBIT OSTEOCLASTOGENESIS

(75) Inventor: Michael Rosenblum, Sugarland, TX (US)

(73) Assignee: Research Development Foundation, Carson City, NV (US)

( * ) Notice: Subject to any disclaimer, the term of this patent is extended or adjusted under 35 U.S.C. 154(b) by 435 days.

(21) Appl. No.: 10/919,193

(22) Filed: Aug. 16, 2004

(65) Prior Publication Data

US 2005/0037967 A1    Feb. 17, 2005

Related U.S. Application Data

(63) Continuation-in-part of application No. 10/846,022, filed on May 14, 2004, now abandoned.

(60) Provisional application No. 60/476,209, filed on Jun. 5, 2003.

(51) Int. Cl.
| A61K 38/46 | (2006.01) |
| A61K 38/43 | (2006.01) |
| A61K 38/18 | (2006.01) |
| A61K 38/19 | (2006.01) |
| A61K 38/20 | (2006.01) |
| C07K 14/475 | (2006.01) |
| C07K 14/49 | (2006.01) |
| C07K 14/52 | (2006.01) |
| C07K 14/54 | (2006.01) |

(52) U.S. Cl. ............... 424/85.1; 424/85.2; 424/94.63; 514/2; 514/12; 530/351; 530/399

(58) Field of Classification Search ............ None
See application file for complete search history.

(56) References Cited

U.S. PATENT DOCUMENTS

| 5,219,739 | A | 6/1993 | Tisher et al. |
| 5,889,155 | A | 3/1999 | Ashkenazi et al. |
| 5,994,104 | A | 11/1999 | Anderson et al. |
| 6,051,230 | A | 4/2000 | Thorpe et al. |
| 6,451,312 | B1 | 9/2002 | Thorpe |
| 6,692,724 | B1 | 2/2004 | Yang et al. |
| 7,067,111 | B1 | 6/2006 | Yang et al. |
| 7,229,604 | B2 | 6/2007 | Yang et al. |
| 2002/0114783 | A1 | 8/2002 | Appukuttan et al. |
| 2003/0040496 | A1 | 2/2003 | Chandler et al. |
| 2003/0082159 | A1 | 5/2003 | Appukuttan et al. |
| 2003/0086919 | A1 | 5/2003 | Rosenblum et al. |
| 2004/0166058 | A1 | 8/2004 | Yang et al. |
| 2004/0248805 | A1 | 12/2004 | Rosenblum |
| 2005/0024380 | A1 | 2/2005 | Lin et al. |
| 2005/0037967 | A1 | 2/2005 | Rosenblum |
| 2005/0129619 | A1 | 6/2005 | Yang et al. |
| 2006/0134810 | A1 | 6/2006 | Bullock |

FOREIGN PATENT DOCUMENTS

| EP | 1506787 | 2/2005 |
| WO | WO 90/13649 | 11/1990 |
| WO | WO 96/06641 | 3/1996 |
| WO | WO 02/083851 | 10/2002 |
| WO | WO 2004/108074 | 12/2004 |
| WO | WO 2006/031353 | 3/2006 |

OTHER PUBLICATIONS

Deckers et al. Endocrinology 141(5): 1667-1674, 2000.*
Pufe et al. Bone 33: 869-876, 2003.*
Cheung et al. Proc. Am. Assoc. Can. Res. 41: 387, 2000 (#2458).*
Kong et al. Molecular control of bone remodeling and osteoporosis. Experimental Gerontology 35: 947-956, 2000.*
Takayanagi et al. Biochem. Biophys. Res. Comm. 240: 279-286, 1997.*
Street et al. PNAS 99(15): 9656-9661, 2002.*
Cheung et al. #2458. In vitro and in vivo studies of VEGF121/RGEL fusion toxin targeting tumor neovasculature. Proc. Am. Assoc. Cancer Res. 41: 387, Mar. 2000.*
Kreitman et al. Immunotoxins for targeted cancer therapy. Advanced Drug Delivery Reviews 31: 53-88, 1998.*
Engsig et al. J. Cell Biol. 151(4): 879-889, 2000.*
Ferrara Endocrine Reviews 25(4): 581-611, 2004.*
Arora et al. Cancer research 59: 183-188, 1999.*
Liu et al., "Mechanistic studies of a novel human fusion toxin composed of vascular endothelial growth factor (VEGF)121 and the serine protease granzyme B: directed apoptotic events in vascular endothelial cells," *Mol. Cancer Therapeutics*, 2:949-959, 2003.
Veenendaal et al., "In vitro and in vivo studies of a VEGF121/rGelonin chimeric fusion toxin targeting the neovasculature of solid tumors," *Proc. Natl. Acad. Sci. USA*, 99:7866-7871, 2002.
Murata et al., "Combrastatin A-4 disodium phosphate: a vascular targeting agent that improves the anti-tumor effects of hyperthermia, radiation, and mild thermotherapy," *Int. J. Radiation Oncology Biol. Phys.*, 51:1081-1024, 2001.
Wild et al., "Inhibition of angiogenesis and tumor growth by VEGF121-toxin conjugate: differential effect on proliferating endothelial cells," *Br. J. Cancer*, 83:1077-1083, 2000.
Arora et al., "Vascular endothelial growth factor chimeric toxin is highly active against endothelial cells," *Cancer Res.*, 59:183-188, 1999.
Cheung et al., "In vitro and in vivo studies of VEGF121/RGEL fusion toxin targeting tumor neovasculature," *Proc. Am. Assoc. Cancer Res.*, 41:387, 2000 (Abstract No. 2458).
Gerber et al., "Andiogenesis and Bone Growth," *TCM*, 10:223-228, 2000.

(Continued)

*Primary Examiner*—Christine J Saoud
(74) *Attorney, Agent, or Firm*—Fulbright & Jaworski LLP

(57) ABSTRACT

The 121-amino acid isoform of vascular endothelial growth factor ($VEGF_{121}$) is linked by a flexible G4S tether to a cytotoxic molecule such as toxin gelonin or granzyme B and expressed as a soluble fusion protein. The $VEGF_{121}$ fusion protein exhibits significant anti-tumor vascular-ablative effects that inhibit the growth of primary tumors and inhibit metastatic spread and vascularization of metastases. The $VEGF_{121}$ fusion protein also target osteoclast precursor cells in vivo and inhibits osteoclastogenesis.

12 Claims, 39 Drawing Sheets

OTHER PUBLICATIONS

Kreitman et al., "Immunotoxins for targeted cancer therapy," *Adv. Drug Delivery Rev.*, 31:53-88, 1998.

Rosenblum et al., "Recombinant immunotoxins directed against the c-erb-2/HER2/neu oncogene product: in vitro cytotoxicity, pharmacokinetics, and in vivo efficacy studies in xenograft models," *Clin. Cancer Res.*, 5:865-874, 1999.

Smyth et al., "Granzymes: exogenous proteinases that induce target cell apoptosis," *Immunology Today*, 16: 202-206, 1995.

Adamis et al., "Increased vascular endothelial growth factor levels in the vitreous of eyes with proliferative diabetic retinopathy," *Am. J. Opthalmol.*, 118:445-450, 1994.

Adamis et al., "Inhibition of vascular endothelial growth factor prevents retinal ischemia-associated iris neovascularization in a nonhuman primate," *Arch. Ophthalmol.*, 114:66-71, 1996.

Aiello et al., "Suppression of retinal neovascularization in vivo by inhibition of vascular endothelial growth factor (VEGF) using soluble VEGF-receptor chimeric proteins," *Proc. Natl. Acad. Sci. USA*, 92:10457-10461, 1995.

Aiello et al., "Vascular endothelial growth factor in ocular fluid of patients with diabetic retinopathy and other retinal disorders," *N. Engl. J. Med.*, 331:1480-1487, 1994.

Anand-Apte et al., "A review of tissue inhibitor of metalloproteinases-3 (TIMP-3) and experimental analysis of its effect on primary tumor growth," *Biochem. Cell. Biol.*, 74:853-862, 1996.

Bergers et al., "Effects of Angiogenesis Inhibitors of Multistage Carcinogenesis of Mice," *Science*, 284:808-812, 1999.

Bhisitkul et al., "An antisense oligodeoxynucleotide against vascular endothelial growth factor in a nonhuman primate model of iris neovascularization," *Arch Ophthalmol*, 123:214-219, 2005.

Bigg et al., "Specific, high affinity binding of tissue inhibitor of metalloproteinases-4 (TIMP-4) to the COOH-terminal hemopexin-like domain of human gelatinase A. TIMP-4 binds progelatinase A and the COOH-terminal domain in a similar manner to TIMP-2," *J. Biol. Chem.*, 272:15496-15500, 1997.

Bird et al., "Single-Chain Antigen-Binding Proteins," *Science*, 242:423-426, 1988.

Boehm et al., "Antiangiogenic therapy of experimental cancer does not induce acquired drug resistance," *Nature*, 390:404-407, 1997.

Brinkmann and Pastan, "Immunotoxins against cancer," *Biochim. Biophys. Acta*, 1198(1):27-45, 1994.

Brooks et al., "Vitreous levels of vascular endothelial growth factor and stromal-derived factor 1 in patients with diabetic retinopathy and cystoid macular edema before and after intraocular injection of triamcinolone," *Arch Ophthalmol*, 122:1801-1807, 2004.

Burbage et al., "Ricin fusion toxin targeted to the human granulocyte-macrophage colony stimulating factor receptor is selectively toxic to acute myeloid leukemia cells," *Leuk Res.*, 21(7):681-690, 1997.

Cao et al., "Kringle 5 of plasminogen is a novel inhibitor of endothelial cell growth," *J. Biol. Chem.*, 272: 22924-22928, 1997.

Chaudhary et al., "A rapid method of cloning functional variable-region antibody genes in *Escherichia coli* as single-chain immunotoxins," *Proc. Natl. Acad. Sci. USA*, 87(3):1066-1070, 1990.

Denekamp, "The tumour microcirculation as a target in cancer therapy: a clearer perspective," *Eur. J. Clin. Invest.*, 29:733-736, 1999.

Endo et al., "Increased levels of vascular endothelial growth factor and advanced glycation end products in aqueous humor of patients with diabetic retinopathy," *Horm Metab Res*, 33:317-322, 2001.

Funatsu et al., "Risk evaluation of outcome of vitreous surgery for proliferative diabetic retinopathy based on vitreous level of vascular endothelial growth factor and angiotensin II," *Br J Ophthalmol*, 88:1064-1068, 2004.

Gan et al., "Vascular endothelial growth factor (VEGF) and its receptor VEGFR-2 in the regulation of corneal neovascularization and wound healing," *Acta Ophthalmol Scand.*, 82:557-563, 2004.

Gaudreault et al., "Preclinical pharmacokinetics of Ranibizumab (rhuFabV2) after a single intravitreal administration," *Invest Ophthalmol Vis Sci*, 46:726-733, 2005.

Gomez et al., "Tissue inhibitors of metalloproteinases: structure, regulation and biological functions," *Eur. J. Cell. Biol.*, 74: 111-122, 1997.

Gragoudas et al., "Pegaptanib for Neovascular Age-Related Macular Degeneration," *N. Eng. J. Med.*, 351:2805-2816, 2004.

Greene et al., "Molecular cloning and characterization of human tissue inhibitor of metalloproteinase 4," *J. Biol. Chem.*, 271:30375-30380, 1996.

Huston et al., "Flexibility of the myosin heavy chain: direct evidence that the region containing SH1 and SH2 can move 10 A under the influence of nucleotide binding," *Biochemistry*, 27(25):8945-8952, 1988.

Ishida et al., "VEGF164-mediated inflammation is required for pathological, but not physiological, ischemia-induced retinal neovascularization," *J Exp Med*, 198:483-489, 2003.

Ji et al., "Selective inhibition by kringle 5 of human plasminogen on endothelial cell migration, an important process in angiogenesis," *Biochem. Biophys. Res. Commun.*, 247:414-419, 1998.

Jin et al., "In vitro and in vivo Studies of VEGF/RGEL Fusion Toxin Targeting Tumor Vascular Endothelium," *Proceedings of the American Association for Cancer Research Annual Meeting*, 42:822, 2001 (Abstract #4414).

Kedar et al., "Targeting bladder tumor vascular endothelium with VEGF/RGEL fusion toxin," *Journal of Urology*, 167:120, 2002 (Abstract #481).

Kelly et al., "Cell type-specific regulation of angiogenic growth factor gene expression and induction of angiogenesis in nonischemic tissue by a constitutively active form of hypoxia-inducible factor 1," *Circ Res*, 93:1074-1081, 2003.

Kirsch et al., "Angiostatin suppresses malignant glioma growth in vivo," *Cancer Res.*, 58:4654-4659, 1998.

Kwak et al., "VEGF is major stimulator in model of choroidal neovascularization," *Invest. Ophthalmol Vis. Sci.*, 41:3158-3164, 2000.

Levin et al., "Registration of clinical trials," *Arch. Ophthalmol.*, 123:1263-1264, 2005.

Lidor et al., "In vitro expression of the diphtheria toxin A-chain gene under the control of human chorionic gonadotropin gene promoters as a means of directing toxicity to ovarian cancer cell lines," *Am. J. Obstet. Gynecol*, 177(3):579-585, 1997.

Liu et al., "Prostate-specific membrane antigen directed selective thrombotic infarction of tumors," *Cancer Res.*, 62:5470-5475, 2002.

Luna et al., "Antagonists of integrin alpha v beta 3 inhibit retinal neovascularization in a murine model," *Lab. Invest.*, 75:563-573, 1996.

Luster and Leder, "IP-10, a -C-X-C- chemokine, elicits a potent thymus-dependent antitumor response in vivo," *J. Exp. Med.*, 178:1057-1065, 1993.

Maguire et al., "Correspondence: To the Editor," *Retina*, 25:101-103, 2005.

Maier et al., "Intravitreal injection of specific receptor tyrosine kinase inhibitor PTK787/ZK222 584 improves ischemia-induced retinopathy in mice," *Graefes Arch Clin Exp Ophthalmol*, 243:593-600, 2005.

Martin et al., "Inhibition of SV40 T antigen-induced hepatocellular carcinoma in TIMP-1 transgenic mice," *Oncogene*, 13:569-576, 1996.

Massuda et al., "Regulated expression of the diphtheria toxin A chain by a tumor-specific chimeric transcription factor results in selective toxicity for alveolar rhabdomyosarcoma cells," *Proc. Natl. Acad. Sci. USA*, 94(26):14701-14706, 1997.

Matsuoka et al., "Expression of pigment epithelium derived factor and vascular endothelial growth factor in choroidal neovascular membranes and polypoidal choroidal vasculopathy," *Br J Ophthalmol*, 88:809-815, 2004.

Mauceri et al., "Combined effects of angiostatin and ionizing radiation in antitumor therapy," *Nature*, 394:287-291, 1998.

McColm et al., "VEGF isoforms and their expression after a single episode of hypoxia or repeated fluctuations between hyperoxia and hypoxia: relevance to clinical ROP," *Mol Vis*, 10:512-520, 2004.

Mohamedali et al., "In vitro and in vivo anti-angiogenic effects of VEGF121/rGel fusion toxin," *Proceedings of the American Association for Cancer Research Annual Meeting*, 44:7, 2003.

Musso et al., "In situ detection of matrix metalloproteinase-2 (MMP2) and the metalloproteinase inhibitor TIMP2 transcripts in human primary hepatocellular carcinoma and in liver metastasis," *J. Hepatol.*, 26:593-605, 1997.

Nambu et al., "Combretastatin A-4 phosphate suppresses development and induces regression of choroidal neovascularization," *Invest. Ophthalmol. Vis. Sci.*, 44:3650-3655, 2003.

Nilsson et al., "Targeted delivery of tissue factor to the ED-B domain of fibronectin, a marker of angiogenesis, mediates the infarction of solid tumors in mice," *Cancer Res.*, 61:711-716, 2001.

O'Reilly et al., "Endostatin: an endogenous inhibitor of angiogenesis and tumor growth," *Cell*, 88:277-85, 1997.

Okamoto et al., "Transgenic mice with increased expression of vascular endothelial growth factor in the retina: a new model of intraretinal and subretinal neovascularization," *Am. J. Pathol*, 151:281-91, 1997.

Ozaki et al., "Blockade of Vascular Endothelial Cell Growth Factor Receptor Signaling Is Sufficient to Completely Prevent Retinal Neovascularization," *Am. J. Pathol.*, 156:679-707, 2000.

Pasqualini et al., "Alpha v integrins as receptors for tumor targeting by circulating ligands," *Nat. Biotechnol.*, 15:542-546, 1997.

Pierce et al., "Vascular endothelial growth factor/vascular permeability factor expression in a mouse model of retinal neovascularization," *Proc. Natl. Acad. Sci. USA*, 92:905-909, 1995.

Ramakrishnan et al., "Vascular endothelial growth factor-toxin conjugate specifically inhibits KDR/flk-1-positive endothelial cell proliferation in vitro and angiogenesis in vivo," *Cancer Res.*, 56:1324-1330, 1996.

Ran et al., "Infarction of solid Hodgkin's tumors in mice by antibody-directed targeting of tissue factor to tumor vasculature," *Cancer Res.*, 58:4646-4653, 1998.

Ran et al., "VEGF121 gelonin fusion protein inhibits breast cancer metastasis in nude mice," *Proceedings of the American Association for Cancer Research Annual Meeting*, 44:1, 2003 (Abstract #4).

Ran et al., "VEGF121-gelonin fusion toxin specifically localizes to tumor blood vesels and induces robust vascular damage in human tumor xenograft models," *Proceedings of the American Association for Cancer Research Annual Meeting*, 43:1006, 2002 (Abstract #4986).

Reich et al., "Small interfering RNA (siRNA) targeting VEGF effectively inhibits ocular neovascularization in a mouse model," *Mol. Vis.*, 9:210-216, 2003.

Saishin et al., "VEGF-TRAP(R1R2) suppresses choroidal neovascularization and VEGF-induced breakdown of the blood-retinal barrier," *J. Cell. Physiol.*, 195:241-248, 2003.

Sasaki et al., "Endostatins derived from collagens XV and XVIII differ in structural and binding properties, tissue distribution and anti-angiogenic activity," *J. Mol. Biol.*, 301(5):1179-1190, 2000.

Seo et al., "Dramatic inhibition of retinal and choroidal neovascularization by oral administration of a kinase inhibitor," *Am. J. Pathol.*, 154:1743-1753, 1999.

Sgadari et al., "Interferon-inducible protein-10 identified as a mediator of tumor necrosis in vivo," *Proc. Natl. Acad. Sci. USA*, 93:13791-13796, 1996.

Sgadari et al., "Mig, the monokine induced by interferon-gamma, promotes tumor necrosis in vivo," *Blood*, 89:2635-2643, 1997.

Smith et al., "Oxygen-induced retinopathy in the mouse," *Invest. Ophthalmol. Vis. Sci.*, 35:101-111, 1994.

Stetler-Stevenson et al., "Tissue inhibitor of metalloproteinases-2 (TIMP-2) mRNA expression in tumor cell lines and human tumor tissues," *J. Biol. Chem.*, 265:13933-13938, 1990.

Tanaka et al., "Downregulation of Fas ligand by shedding," *Nat. Med.*, 4(1):31-36, 1998.

Tannenbaum et al., "The CXC chemokines IP-10 and Mig are necessary for IL-12-mediated regression of the mouse RENCA tumor," *J. Immunol.*, 161:927-932, 1998.

Thorpe, "Vascular targeting agents as cancer therapeutics," *Clin. Cancer Res.*, 10:415-427, 2004.

Tobe et al., "Evolution of neovascularization in mice with overexpression of vascular endothelial growth factor in photoreceptors," *Invest. Ophthalmol. Vis. Sci.*, 39:180-8, 1998.

Wang et al., "Inhibition of tumor growth and metastasis of human breast cancer cells transfected with tissue inhibitor of metalloproteinase 4," *Oncogene*, 14:2767-2774, 1997.

Werdich et al., "Variable oxygen and retinal VEGF levels: correlation with incidence and severity of pathology in a rat model of oxygen-induced retinopathy," *Exp Eye Res*, 79:623-630, 2004.

Witmer et al., "Altered expression patterns of VEGF receptors in human diabetic retina and in experimental VEGF-induced retinopathy in monkey," *Invest Ophthalmol Vis Sci*, 43:849-857, 2002.

Witmer et al., "Vascular endothelial growth factors and angiogenesis in eye disease," *Prog. Retin. Eye Res.*, 22(1):1-29, 2003.

Zhang et al., "Genetic difference in susceptibility to the blood-retina barrier breakdown in diabetes and oxygen-induced retinopathy," *Am J. Pathol*, 166:313-321, 2005.

D'Amore, "Mechanisms of Retinal and Choroidal Neovascularization," *Investigative Opthalmology & Visual Science*, 35(12):3974-3979, 1994.

Fulcher et al., "Use of Immunotoxin to Inhibit Proliferating Human Corneal Endothelium," *Investigative Opthalmology & Visual Science*, 29(5): 755-759, 1988.

Pan et al., "Effects of endostatin-vascular endothelial growth inhibitor chimeric recombinant adenoviruses on antiangiogenesis," *World Journal of Gastroenterology*, 10(10):1409-1414, 2004.

\* cited by examiner

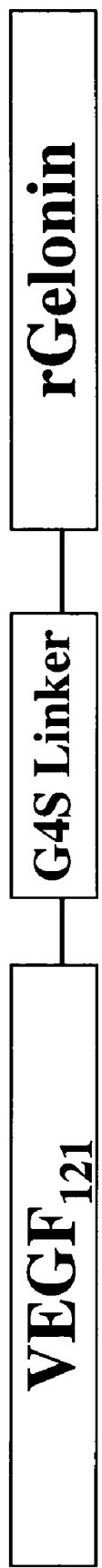
Fig. 1

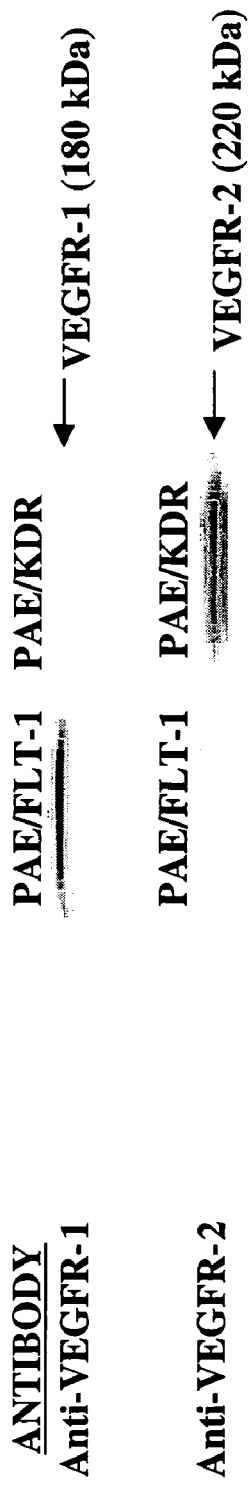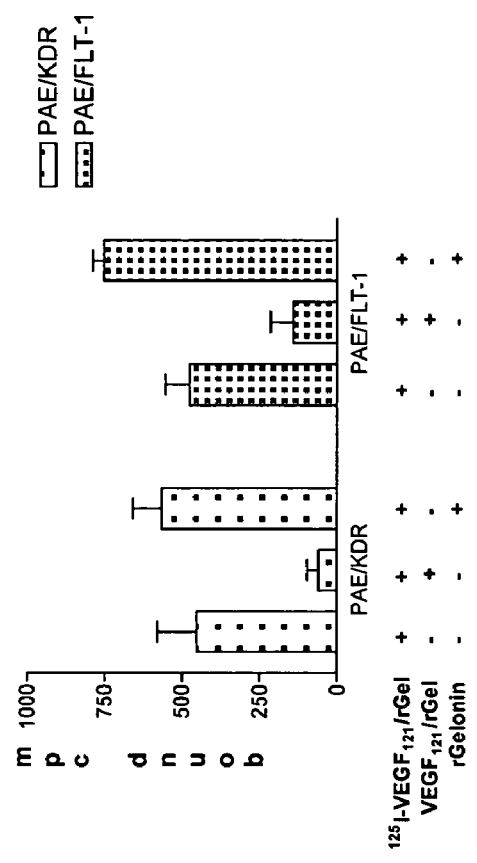
Fig. 6A
Fig. 6B

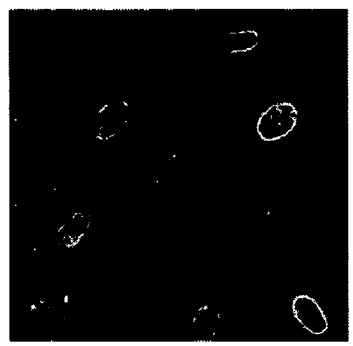
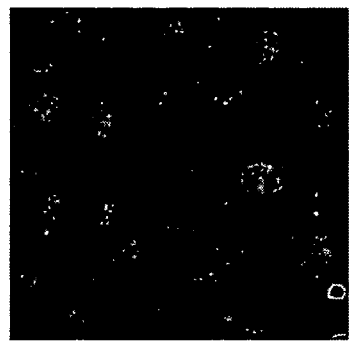
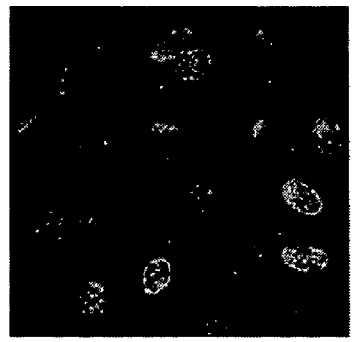
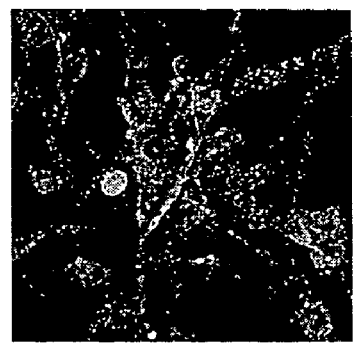
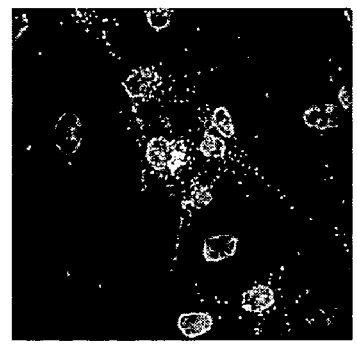
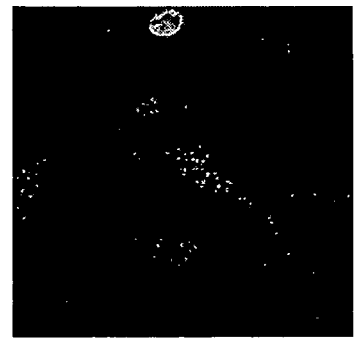
Fig. 7

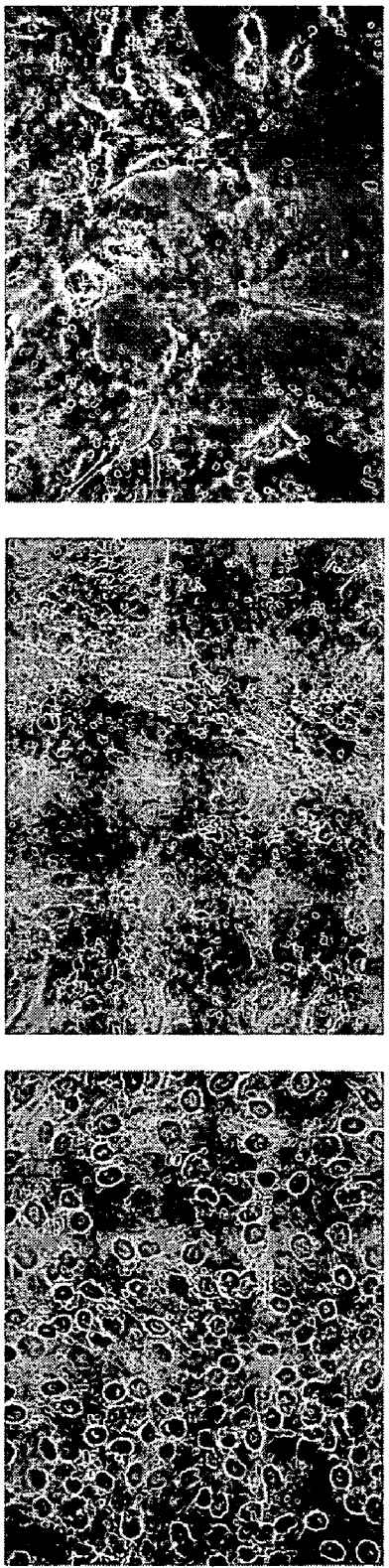
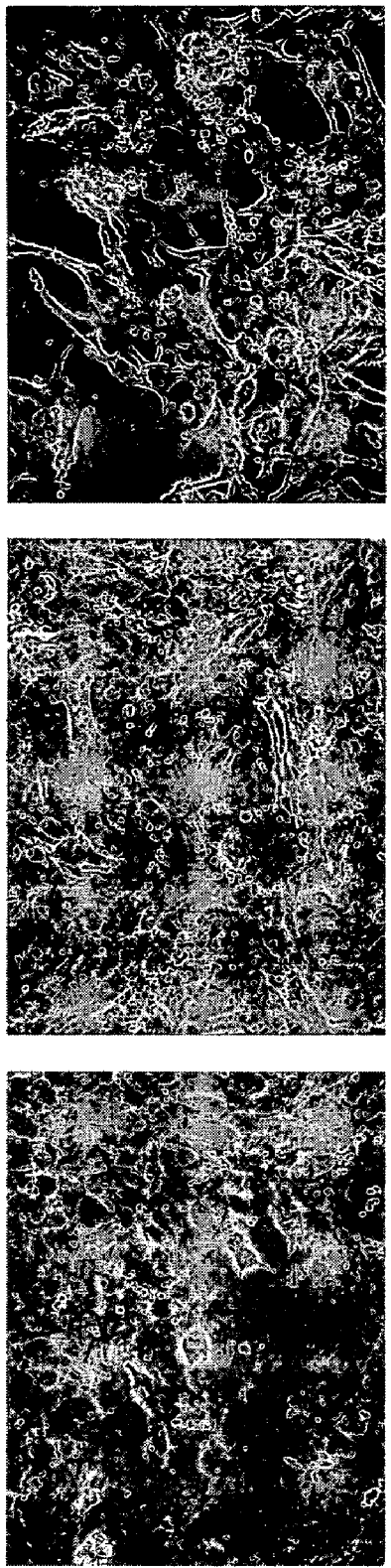
Fig. 9

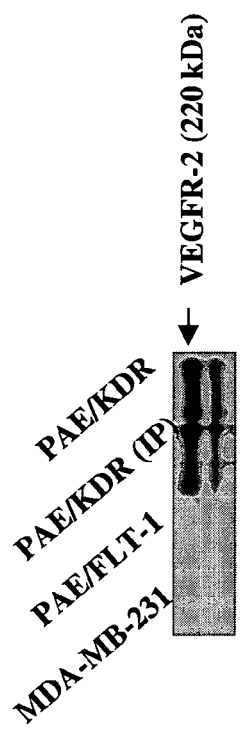
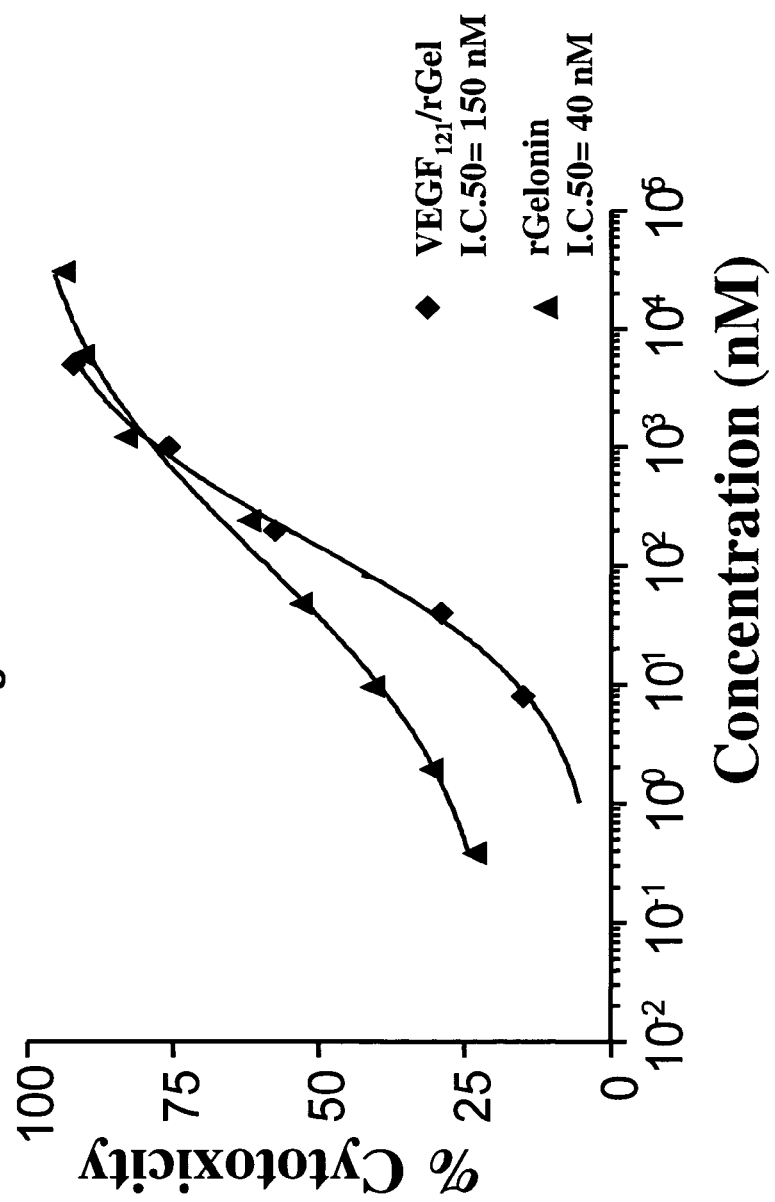
Fig. 15A
Fig. 15B

Mean number of blood vessels per mm

↓ Treatment days
* One mouse did not recover from anesthesia (no tumor)

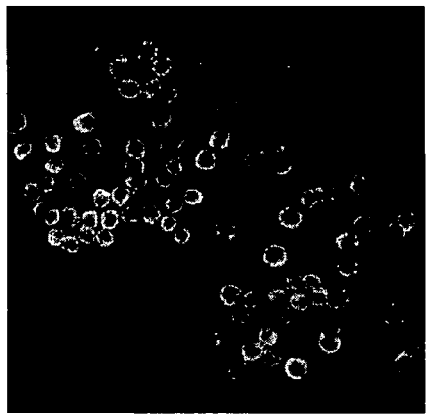
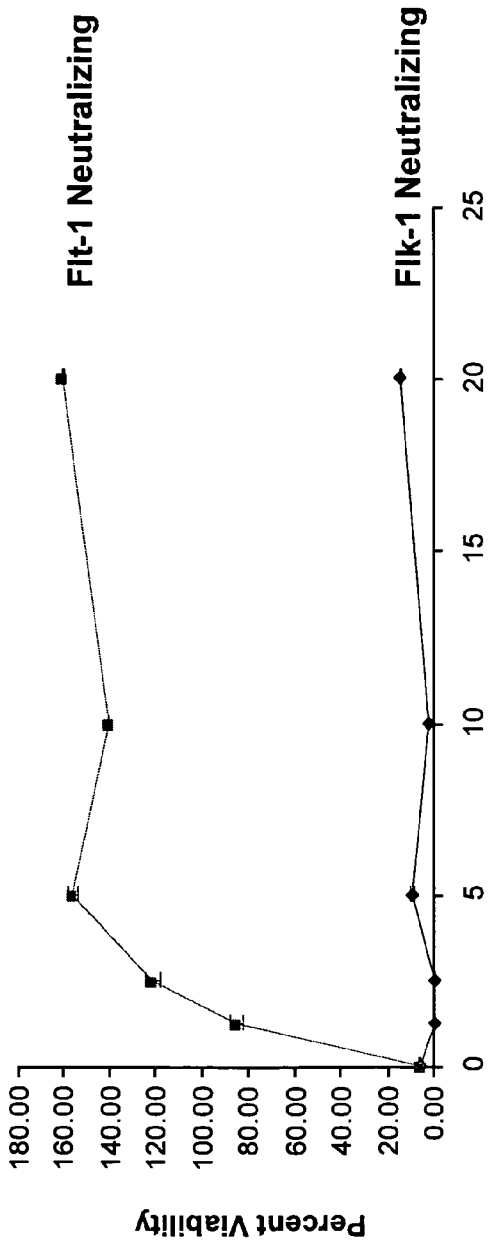
VEGF$_{121}$/rGel     rGel
Fig. 32
Fig. 33

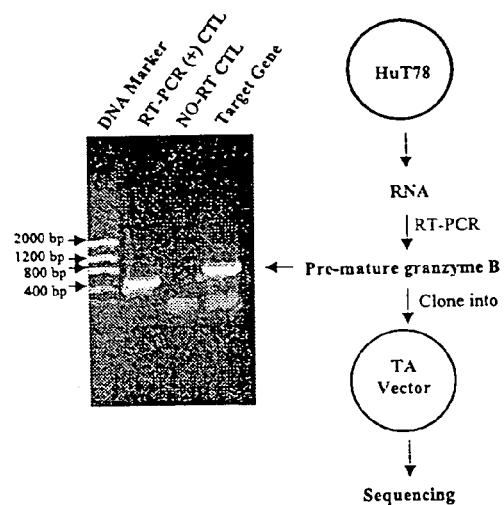

```
1/1                                                              54/18
ATG CAA CCA ATC CTG CTT CTG CTG GCC TTC CTC CTG CTG CCC AGG GCA GAT GCA
 M   Q   P   I   L   L   L   L   A   F   L   L   L   P   R   A   D   A
55/19                                                           108/36
GGG GAG ATC ATC GGG GGA CAT GAG GCC AAG CCC CAC TCC CGC CCC TAC ATG GCT
 G   E   I   I   G   G   H   E   A   K   P   H   S   R   P   Y   M   A
109/37                                                          162/54
TAT CTT ATG ATC TGG GAT CAG AAG TCT CTG AAG AGG TGC GGT GGC TTC CTG ATA
 Y   L   M   I   W   D   Q   K   S   L   K   R   C   G   G   F   L   I
163/55                                                          216/72
CAA GAC GAC TTC GTG CTG ACA GCT GCT CAC TGT TGG GGA AGC TCC ATA AAT GTC
 Q   D   D   F   V   L   T   A   A   H   C   W   G   S   S   I   N   V
217/73                                                          270/90
ACC TTG GGG GCC CAC AAT ATC AAA GAA CAG GAG CCG ACC CAG CAG TTT ATC CCT
 T   L   G   A   H   N   I   K   E   Q   E   P   T   Q   Q   F   I   P
271/91                                                          324/108
GTG AAA AGA CCC ATC CCC CAT CCA GCC TAT AAT CCT AAG AAC TTC TCC AAC GAC
 V   K   R   P   I   P   H   P   A   Y   N   P   K   N   F   S   N   D
325/109                                                         378/126
ATC ATG CTA CTG CAG CTG GAG AGA AAG GCC AAG CGG ACC AGA GCT GTG CAG CCC
 I   M   L   L   Q   L   E   R   K   A   K   R   T   R   A   V   Q   P
379/127                                                         432/144
CTC AGG CTA CCT AGC AAC AAG GCC CAG GTG AAG CCA GGG CAG ACA TGC AGT GTG
 L   R   L   P   S   N   K   A   Q   V   K   P   G   Q   T   C   S   V
433/145                                                         486/162
GCC GGC TGG GGG CAG ACG GCC CCC CTG GGA AAA CAC TCA CAC ACA CTA CAA GAG
 A   G   W   G   Q   T   A   P   L   G   K   H   S   H   T   L   Q   E
487/163                                                         540/180
GTG AAG ATG ACA GTG CAG GAA GAT CGA AAG TGC GAA TCT GAC TTA CGC CAT TAT
 V   K   M   T   V   Q   E   D   R   K   C   E   S   D   L   R   H   Y
541/181                                                         594/198
TAC GAC AGT ACC ATT GAG TTG TGC GTG GGG GAC CCA GAG ATT AAA AAG ACT TCC
 Y   D   S   T   I   E   L   C   V   G   D   P   E   I   K   K   T   S
595/199                                                         648/216
TTT AAG GGG GAC TCT GGA GGC CCT CTT GTG TGT AAC AAG GTG GCC CAG GGC ATT
 F   K   G   D   S   G   G   P   L   V   C   N   K   V   A   Q   G   I
649/217                                                         702/234
GTC TCC TAT GGA CGA AAC AAT GGC ATG CCT CCA CGA GCC TGC ACC AAA GTC
 V   S   Y   G   R   N   N   G   M   P   P   R   A   C   T   K   V
703/235                                                         744/248
TCA AGC TTT GTA CAC TGG ATA AAG AAA ACC ATG AAA CGC TAC TAA  (SEQ ID NO: 14)
 S   S   F   V   H   W   I   K   K   T   M   K   R   Y   -   (SEQ ID NO:15)
```

Fig. 35

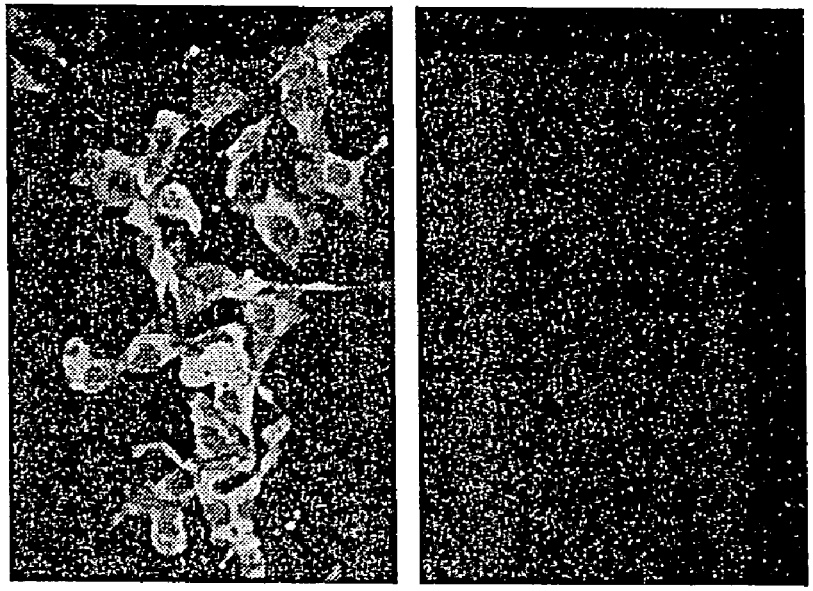
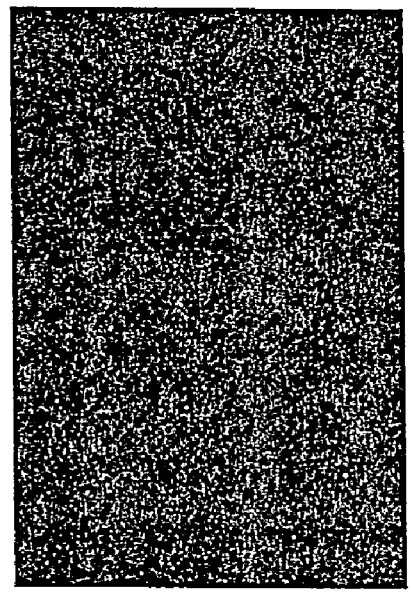
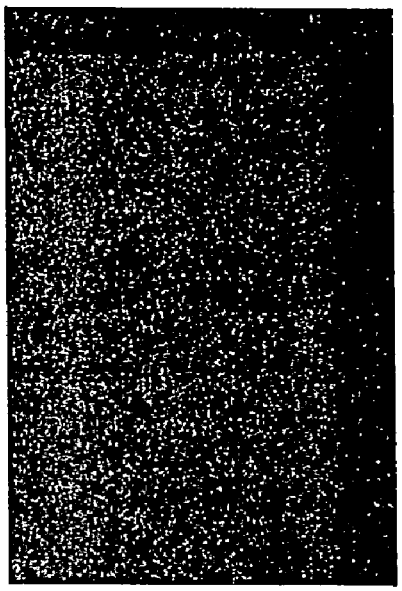
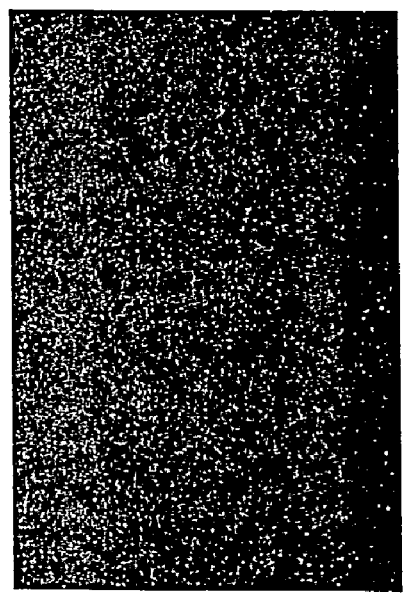
Fig. 39

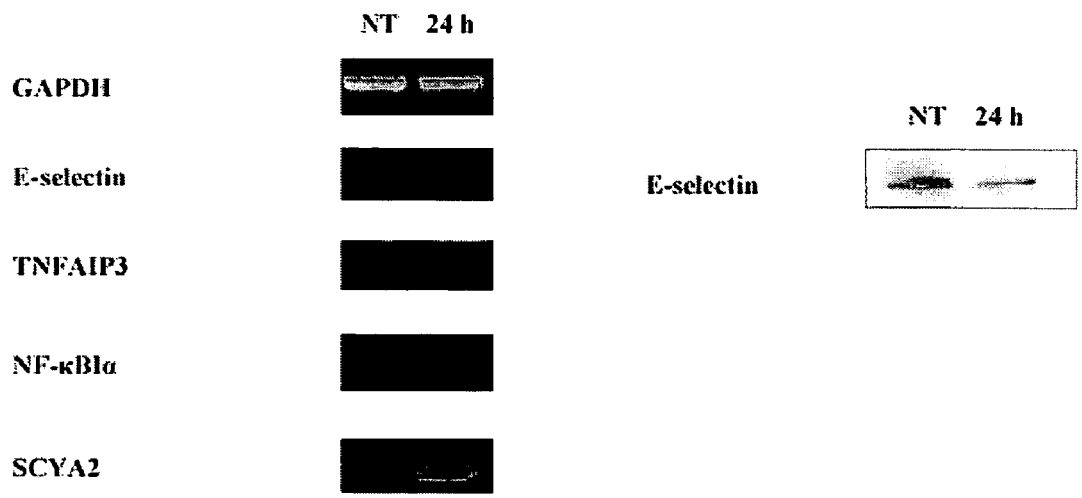
Fig. 45
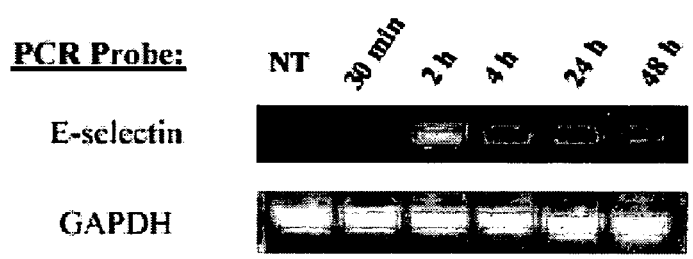
Fig. 46

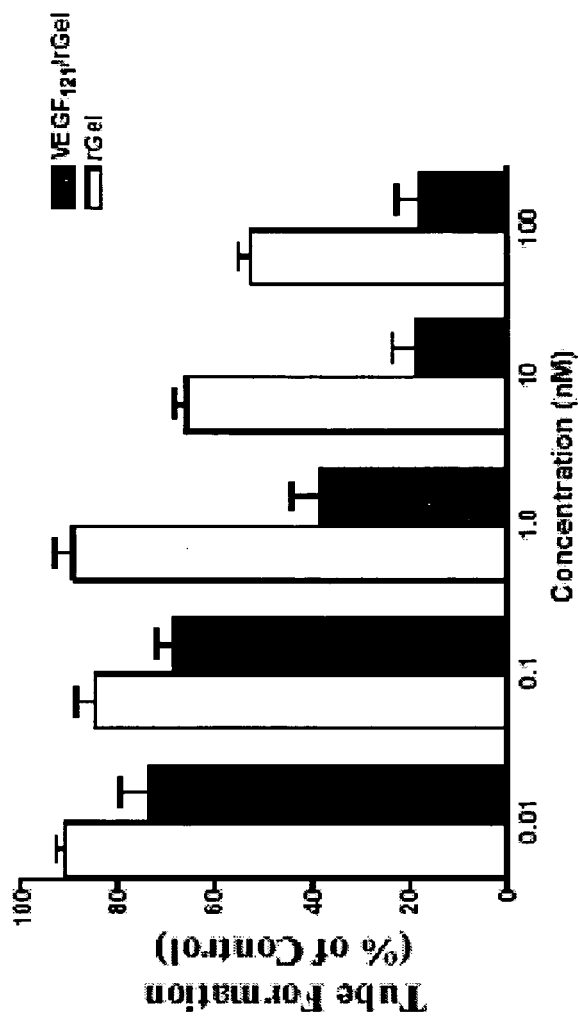
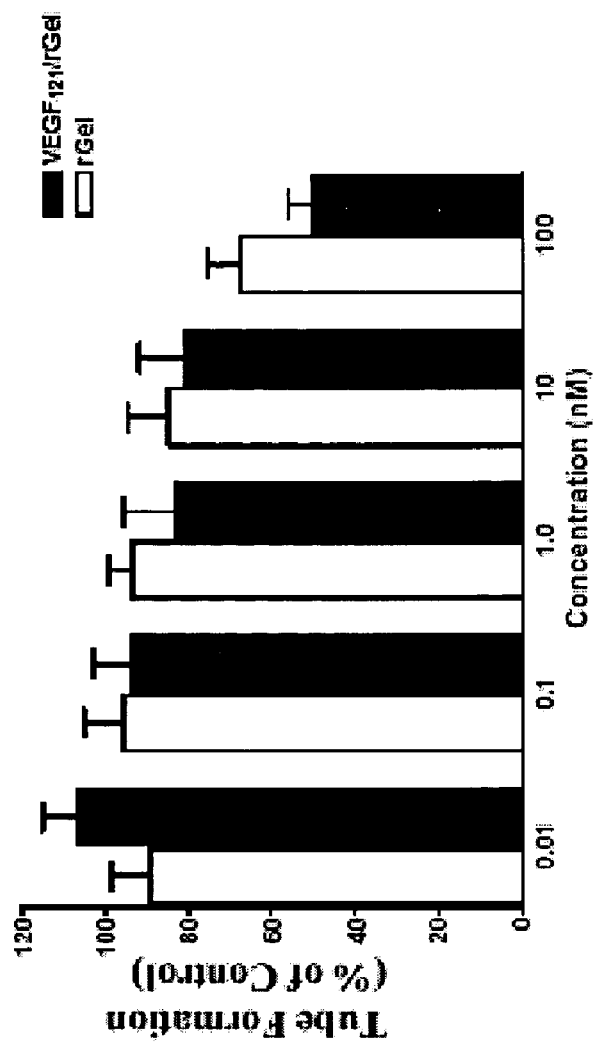
Fig. 47A
Fig. 47B

US 7,601,341 B2

VASCULAR ENDOTHELIAL GROWTH FACTOR FUSION CONSTRUCTS USED TO INHIBIT OSTEOCLASTOGENESIS

CROSS-REFERENCE TO RELATED APPLICATION

This continuation-in-part patent application claims benefit of priority of U.S. Ser. No. 10/846,022, filed May 14, 2004 now abandoned, which claims benefit of provisional patent application U.S. Ser. No. 60/476,209, filed Jun. 5, 2003.

FEDERAL FUNDING LEGEND

This invention was produced in part using funds obtained through Grants 5P30CA16672-26 and P30 CA016672-28 from the National Cancer Institute and Grants ROI CA 7495 and P50 CA91846 from the National Institutes of Health. Consequently, the federal government has certain rights in this invention.

BACKGROUND OF THE INVENTION

1. Field of the Invention

The present invention relates generally to the fields of cancer research and targeted therapy. More specifically, the present invention relates to fusion constructs comprising an isoform of vascular endothelial growth factor and uses of such constructs.

2. Description of the Related Art

Vascular endothelial growth factor (VEGF)-A plays a central role in the growth and metastasis of solid tumors, and acts as a primary stimulant of vascularization in solid tumors. VEGF-A enhances endothelial cell proliferation, migration, and survival and is essential for blood vessel formation. Other roles of vascular endothelial growth factor include wound healing, vascular permeability and the regulation of blood flow. Through alternative splicing of RNA, human vascular endothelial growth factor exists as at least four isoforms of 121, 165, 189, or 206 amino acids. The lowest molecular weight isoform, designated $VEGF_{121}$, is a non-heparan sulfate-binding isoform that exists in solution as a disulfide-linked homodimer.

VEGF is released by a variety of tumor cells. The angiogenic actions of VEGF are mediated through two related receptor tyrosine kinases, kinase domain receptor (KDR) and FLT-1 in the human, and Flk-1 and Flt-1 in the mouse. Both are largely restricted to vascular endothelial cells. KDR/Flk-1 and FLT-1 receptors are overexpressed on the endothelium of tumor vasculature. In contrast, these receptors are almost undetectable in the vascular endothelium of adjacent normal tissues. The receptors for vascular endothelial growth factor thus seem to be excellent targets for the development of therapeutic agents that inhibit tumor growth and metastatic spread through inhibition of tumor neovascularization.

To this end, $VEGF_{121}$ would be an appropriate carrier to deliver a toxic agent selectively to tumor vascular endothelium. $VEGF_{121}$, exists in solution as a disulfide linked homodimer and binds to KDR and FLT-1 in a heparin-independent manner. It does not bind neuropilin-1 or neuropilin-2. $VEGF_{121}$ has been shown to contain the full biological activity of the larger variants.

Molecular engineering enabled the synthesis of novel chimeric molecules having therapeutic potential. Chimeric fusion constructs targeting the IL-2 receptor, the EGF receptor, and other growth factor/cytokine receptors have been described. It has also been showed that a chemical conjugate of vascular endothelial growth factor and truncated diphtheria toxin has impressive cytotoxic activity on cell lines expressing receptors for vascular endothelial growth factor. Further studies with VEGF/diphtheria toxin fusion constructs demonstrated selective toxicity to Caprice's sarcoma cells and dividing endothelial cells in vitro and in vivo. However, the prior art is deficient in fusion constructs comprising vascular endothelial growth factor and other cytotoxic molecule with improved biochemical and pharmacological properties. The present invention fulfills this long-standing need and desire in the art.

SUMMARY OF THE INVENTION

The present invention discloses targeting of neovasculature of solid tumors with a chimeric fusion toxin comprising the 121-amino acid isoform of vascular endothelial growth factor ($VEGF_{121}$). In one embodiment, the chimeric fusion toxin ($VEGF_{121}$/rGel) consists of $VEGF_{121}$ and recombinant gelonin (rGel), a low molecular weight single chain toxin with a mechanism of action similar to that of ricin A-chain. $VEGF_{121}$ is linked by a flexible G4S tether to the toxin gelonin and expressed as a soluble protein in bacteria. Both $VEGF_{121}$/rGel and $VEGF_{121}$ stimulated cellular kinase domain receptor (KDR) phosphorylation. The $VEGF_{121}$/rGel fusion construct was highly cytotoxic to endothelial cells overexpressing the KDR/Flk-1 receptor. Endothelial cells overexpressing FLT-1 were not sensitive to the fusion protein.

While several studies have shown both receptors of $VEGF_{121}$, namely VEGFR-1 (FLT-1) and VEGFR-2 (KDR/Flk-1), to be over-expressed on the endothelium of tumor vasculature, the present invention reports several surprising results which demonstrate that $VEGF_{121}$/rGel has several advantageous properties. Cell ELISA using antibodies specific to either KDR or FLT-1 indicate binding of $VEGF_{121}$/rGel to both receptors. While $VEGF_{121}$/rGel binds to both FLT-1 and KDR, internalization of $VEGF_{121}$/rGel is mediated only by KDR and not FLT-1.

Experiments with human melanoma, human prostate tumor or bladder tumor xenografts demonstrate successful use of $VEGF_{121}$/rGel fusion construct for the targeted destruction of tumor vasculature in vivo. The present invention also indicates that the anti-tumor vascular-ablative effect of $VEGF_{121}$/rGel may be utilized not only for treating primary tumors but also for inhibiting metastatic spread and vascularization of metastases. Taken together, these results indicate that selective destruction of tumor vasculature can be achieved with $VEGF_{121}$/rGel in mice, giving impressive anti-tumor effects. Gross morphological toxicity to normal organs was not visible in animals treated with a therapeutic dose. Therefore, $VEGF_{121}$/rGel is a potential antitumor agent useful for treating cancer patients.

In another embodiment, there is provided a chimeric fusion toxin (GrB/$VEGF_{121}$) consisting of $VEGF_{121}$, and granzyme B (GrB), a serine protease capable of inducing apoptosis through both caspase-dependent and caspase-independent pathways. GrB/$VEGF_{121}$ induced apoptotic events specifically on FLK-1-expressing porcine aortic endothelial cells as assessed by terminal deoxynucleotidyl transferase-mediated nick end labeling assay, DNA laddering, and cytochrome c release from mitochondria. In addition, the fusion construct mediated cleavage of caspase-8, caspase-3, and poly(ADP-ribose) polymerase in target endothelial cells within 4 h after treatment. In conclusion, delivery of the human proapoptotic pathway enzyme granzyme B to tumor vascular endothelial cells or to tumor cells may have significant therapeutic potential and represents a potent new class of targeted therapeutic agents with a unique mechanism of action.

Thus, the present invention is directed to compositions of matter comprising a conjugate comprising an isoform of vascular endothelial growth factor (VEGF) and a cytotoxic molecule. In another embodiment, the conjugate comprises a cytotoxic molecule and a peptide that binds to both VEGF receptor type 1 (Flt-1) and VEGF receptor type 2 (kinase domain receptor/Flk-1). In general, the cytotoxic molecule is a toxin such as gelonin or a molecule that induces apoptosis such as granzyme B.

In another embodiment of the present invention, there are provided methods of killing cells expressing type 2 or type 1 VEGF receptors by the present conjugates which are internalized by VEGF receptor type 2 or type 1 respectively.

In yet another embodiment, there are provided methods of using the conjugates of the present invention to inhibit tumor growth, metastatic spread or vascularization of metastases in an animal or a human.

The present invention further provides methods of using the conjugates of the present invention to inhibit osteoclastogenesis or angiogenesis in an animal or a human.

Other aspects, features, and advantages of the present invention will be apparent from the following description of the presently preferred embodiments of the invention. These embodiments are given for the purpose of disclosure.

BRIEF DESCRIPTION OF THE DRAWINGS

FIG. 1 shows the design and construction of $VEGF_{121}$/rGel. Constructs of the targeting molecule ($VEGF_{121}$) to the cytotoxic agent (gelonin) were expressed in two orientations, with either $VEGF_{121}$ or gelonin at the N-terminus. A G4S tether was used to fuse $VEGF_{121}$, and gelonin and reduce steric hindrance.

FIGS. 6A-B show expression of KDR and FLT-1. FIG. 6A: Whole cell lysate (30 µg) of PAE/KDR and PAE/FLT-1 was run on an SDS-PAGE gel, transferred to a PVDF membrane and immunoblotted using the appropriate antibody. Expression of both receptors on their respective cell lines was confirmed. FIG. 6B: Receptor-specific binding of radio-labeled $VEGF_{121}$/rGel is demonstrated on cells expressing these receptors. Binding was reduced with unlabeled $VEGF_{121}$/rGel but not by unlabeled gelonin.

FIG. 7 shows internalization of $VEGF_{121}$/rGel into PAE/KDR and PAE/FLT-1 cells. PAE/KDR cells were incubated with 4 µg/ml $VEGF_{121}$/rGel at the timepoints indicated. Cells were then incubated with an anti-gelonin polyclonal antibody (1:200) followed by a FITC-conjugated secondary antibody (1:80). Nuclei were stained with propidium iodide. $VEGF_{121}$/rGel enters PAE/KDR cells within one hour of treatment. However, PAE/FLT-1 cells did not internalize $VEGF_{121}$/rGel even after 24 hours of incubation with $VEGF_{121}$/rGel.

FIG. 9 shows that cytotoxicity of $VEGF_{121}$/rGel to PAE/KDR cells does not result in apoptosis. PAE/KDR cells were grown overnight. 1 nM $VEGF_{121}$/rGel (twice the $IC_{50}$) was added and incubated for 24, 48 and 72 hours. The cells were analyzed for TUNEL. Positive control cells were incubated with 1 mg/ml DNAse for 10 minutes at 37° C.

FIGS. 15A-B show VEGF$_{121}$/rGel is not cytotoxic to MDA-MB-231 cells. Log-phase MDA-MB-231 cells were treated with various doses of VEGF$_{121}$/rGel or rGel for 72 hrs. The cytotoxic effects of both agents were similar, indicating no specific cytotoxicity of the fusion construct compared to free toxin on these cells (FIG. 15B). Western analysis demonstrated the presence of VEGFR-2 on endothelial cells transfected with the R2 receptor (PAE/KDR) but not on cells expressing the FLT-1 receptor (PAE/FLT-1, negative control). The MDA-MB-231 cells did not express detectable amounts of VEGFR-2 (FIG. 15A).

FIG. 18B shows representative images demonstrating reduction of vascular density in foci of comparable size in mice treated with rGel (left) and VEGF$_{121}$/rGel fusion protein (right).

FIG. 32 shows intracellular delivery of VEGF$_{121}$/rGel to RAW cells. RAW cells were treated with either VEGF$_{121}$/rGel or rGel for 24 hrs. The cells were fixed, acid-washed to remove surface-bound material, permeabilized, and immunostained for the presence of rGel (green). The cells were counterstained with propidium iodide (red) to identify nuclei.

FIG. 33 shows neutralizing antibody to Flt-1, but not anti-Flk-1/KDR, blocks the cytotoxic effect of VEGF$_{121}$/rGel. Cells were pre-treated with neutralizing antibody for 1 h prior to addition of 40 nM VEGF$_{121}$/rGel.

FIG. 35 shows cloning of human granzyme B (GrB) gene from HuT-78 cells. HuT-78 RNA was isolated, and premature GrB cDNA (~800 bp) was amplified by reverse transcription-PCR and cloned into the PCR 2.1 TA vector. The human granzyme B sequence with 20-amino acid signal sequence was confirmed and designated as premature granzyme B. Once the signal peptide was removed, the mature amino-terminal Ile-Ile-Gly-Gly sequence of granzyme B was generated.

FIG. 39 shows internalization of GrB/VEGF$_{121}$ into porcine aortic endothelial (PAE) cells. PAE cells were plated onto 16-well chamber slides (1×10$^4$ cells/well), treated with 100 nM of GrB/VEGF$_{121}$ for 4 h and then washed briefly with PBS. The cell surface was stripped with glycine buffer (pH 2.5) and the cells were fixed in 3.7% formaldehyde and permeabilized in PBS containing 0.2% Triton X-100. After blocking, samples were incubated with anti-granzyme B antibody and treated with FITC-coupled anti-mouse IgG. The slides were analyzed under a fluorescence microscope. The granzyme B moiety of GrB/VEGF$_{121}$ was delivered into the cytosol of PAE/FLK-1 but not into that of PAE/FLT-1 cells after 4-h treatment.

FIG. 41B shows apoptotic cells as percentage of the total counted cells (>200 cells) in randomly selected fields (200×); bars, SD.

FIG. 45 shows validation of the microarray analysis by PCR. Upregulation of genes for E-selectin, TNFAIP3, NF-kBIa and SCYA2 were validated by RT-PCR. GAPDH levels were assessed as a control. Protein levels of E-selectin in HUVECs treated with VEGF$_{121}$/rGel are shown on the right. NT, not treated.

FIG. 46 shows VEGF$_{121}$/rGel-induced E-selectin expression in PAE/KDR cells. RNA from PAE/KDR cells that were untreated or treated with VEGF$_{121}$/rGel for the periods indicated were examined by PCR. GAPDH primers were used as a control for loading. RNA levels of E-selectin were all upregulated in PAE/KDR cells (FIG. 46A). Protein levels of E-selectin are also upregulated (FIG. 46B).

FIGS. 47A-B show VEGF$_{121}$/rGel-mediated inhibition of tube formation in PAE/KDR cells. PAE/KDR (FIG. 47A) and PAE/Flt-1 cells (FIG. 47B) were added to Matrigel-coated plates, treated with VEGF$_{121}$/rGel or rGel at the concentrations indicated, and analyzed for tube formation after 24 h. For PAE/KDR cells, a dose of 1 nM VEGF$_{121}$/rGel was sufficient to inhibit tube formation by 50%, whereas the same degree of inhibition was seen with rGel only at 100 nM. In contrast, up to 100 nM VEGF$_{121}$/rGel was needed to inhibit tube formation in PAE/Flt-1 cells.

FIG. 50B shows VEGF$_{121}$/rGel decreased the number of newly sprouting vessels. VEGF$_{121}$/rGel at a concentration of 1 nM dramatically affected the formation of the neovasculature, completely inhibiting bFGF-mediated stimulation of the neovasculature. As expected, rGel did not affect the number of newly sprouting vessels. Data shown represent the means±standard deviations from replicated experiments. *, P<0.001; t-test, double-sided.

DETAILED DESCRIPTION OF THE INVENTION

Figure 2:
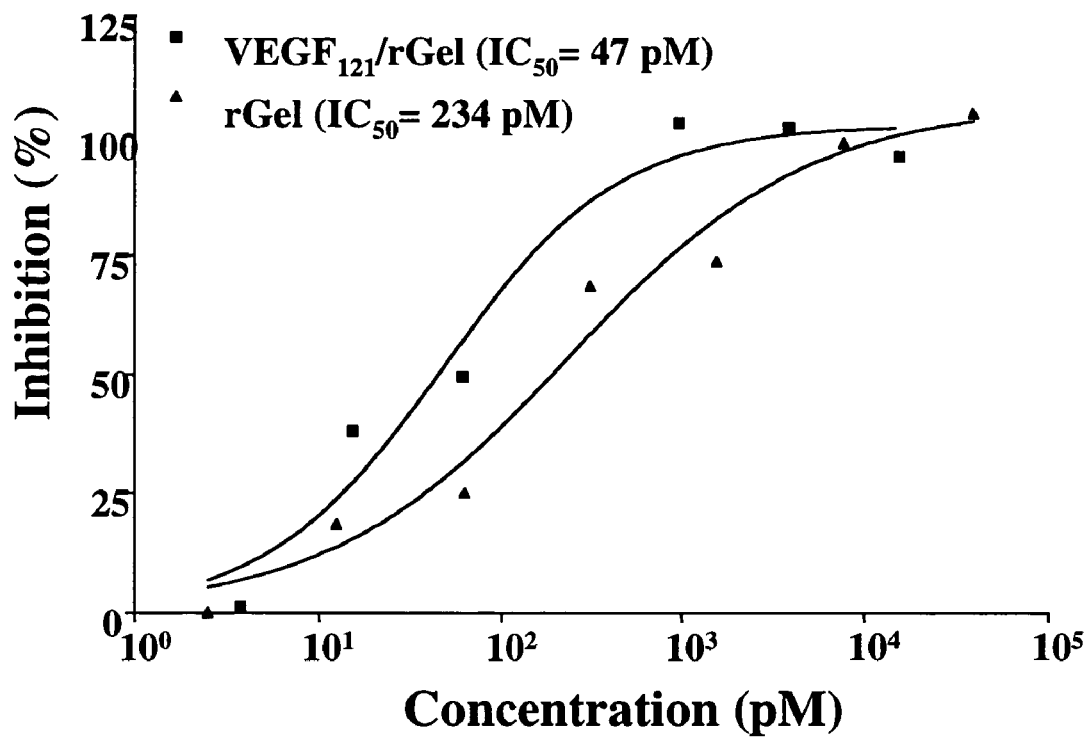
FIG. 2 shows a rabbit reticulocyte assay used to determine the ability of $VEGF_{121}$/rGel and rGel to inhibit translation in a cell-free system. The fusion of $VEGF_{121}$, and recombinant gelonin does not reduce the activity of the toxin component.

The expression of vascular endothelial growth factor and its receptors has been closely linked to tumor vascularity, metastasis, and progression. Several groups have developed anti-angiogenic drugs that block kinase activity of the vascular endothelial growth factor receptors or monoclonal antibodies that block vascular endothelial growth factor-receptor interactions. The present invention demonstrates chimeric fusion constructs containing the 121-amino acid isoform of vascular endothelial growth factor (VEGF$_{121}$) and a cytotoxic molecule such as plant toxin gelonin or serine protease granzyme B.

Agents targeting the neovascularization process in tumors have significant potential for therapeutic impact. Molecules which interfere with the growth and development of vascular endothelial cells by targeting the VEGF/receptor complex have an additional advantage since these agents do not have to penetrate into the tumor parenchyma and the receptor targets are expressed on the luminal surface of tumor vascular endothelium.

Possible binding of vascular endothelial growth factor-containing constructs to the neuropilin receptor could be a source of unwanted toxicity and mis-targeting of the complex; however, it has been shown that the VEGF$_{121}$ fragment as opposed to other isoforms of VEGF-A does not appear to bind to this receptor.

It is specifically contemplated that pharmaceutical compositions may be prepared using the novel fusion constructs of the present invention. In such a case, the pharmaceutical composition comprises the novel fusion constructs of the present invention and a pharmaceutically acceptable carrier. A person having ordinary skill in this art would readily be able to determine, without undue experimentation, the appropriate dosages and routes of administration of this fusion toxin of the present invention. When used in vivo for therapy, the fusion construct of the present invention is administered to the patient or an animal in therapeutically effective amounts, i.e., amounts that eliminate or reduce the tumor burden or other desired biological effects. It will normally be administered parenterally, preferably intravenously, but other routes of administration will be used as appropriate.

The dose and dosage regimen will depend upon the nature of the disease or cancer (primary or metastatic) and its population, the characteristics of the particular fusion toxin, e.g., its therapeutic index, the patient, the patient's history and other factors. The amount of fusion toxin administered will typically be in the range of about 0.01 to about 100 mg/kg of patient weight. The schedule will be continued to optimize effectiveness while balanced against negative effects of treatment. See *Remington's Pharmaceutical Science,* 17th Ed. (1990) Mark Publishing Co., Easton, Pa.; and *Goodman and Gilman's: The Pharmacological Basis of Therapeutics,* 8th Ed. (1990) Pergamon Press. For parenteral administration, the fusion toxin protein will most typically be formulated in a unit dosage injectable form (solution, suspension, emulsion) in association with a pharmaceutically acceptable parenteral vehicle. Such vehicles are preferably non-toxic and non-therapeutic. Examples of such vehicles are water, saline, Ringer's solution, dextrose solution, and 5% human serum albumin. Non-aqueous vehicles such as fixed oils and ethyl oleate may also be used.

Liposomes may be used as carriers. The vehicle may contain minor amounts of additives such as substances that enhance isotonicity and chemical stability, e.g., buffers and preservatives. The fusion toxin will typically be formulated in such vehicles at concentrations of about 0.01 mg/ml to 1000 mg/ml.

The present invention is directed to a composition of matter comprising a conjugate comprising a cytotoxic molecule, such as a small interfering RNA, and a peptide that binds to both VEGF receptor type 1 (Flt-1) and VEGF receptor type 2 (kinase domain receptor/Flk-1). In one embodiment, the peptide is an isoform of VEGF such as those having a sequence of SEQ ID NOs:28-34. In general, the cytotoxic molecule is a toxin such as gelonin or a signal transduction protein capable of generating apoptotic signals. Representative signal transduction proteins for apoptosis induction include granzyme B, Bax, TNF-a, TNF-b, TNF-like molecule, TGF-b, IL-12, IL-3, IL-24, IL-18, TRAIL, IFN-a, IFN-b, IFN-g, Bcl-2, Fas ligand and caspases. In one embodiment, the conjugate is a fusion protein of the 121-amino acid isoform of VEGF (VEGF$_{121}$) and a cytotoxic molecule. For example, the fusion protein may include a linker such as G$_4$S, (G$_4$S)2, the 218 linker, (G$_4$S)3, enzymatically cleavable linker, pH cleavable linker or any similar linker well known to a person having ordinary skill in this art.

In addition to the 121-amino acid isoform of VEGF, the present invention encompasses other peptides that bind to both VEGF receptor type 1 and type 2. A number of such peptides have been reported. For example, peptides binding type 2 VEGF receptor can be identified by screening with membrane-expressed type 2 VEGF receptors or with anti-VEGF neutralizing monoclonal antibody (Binetruy-Tournaire et al., 2000; Wu et al., 2002). A heterodimeric VEGF antagonist comprising binding domains for VEGF receptor type 1 and type 2 at one pole of the dimer has been shown to block VEGF receptor type 1- and type 2-mediated activities (Leenders et al., 2002). Moreover, VEGF receptor-targeting peptides can be high affinity antibodies selected from phage display library (Lu et al., 2003).

In another embodiment, there is provided a method of using the conjugates of the present invention to kill cells expressing type 2 VEGF receptors (kinase domain receptor/Flk-1 receptors). The conjugate can bind to both VEGF receptor type 1 (Flt-1) and VEGF receptor type 2 (KDR/Flk-1) but is internalized by VEGF receptor type 2 expressed on the cells. In general, the conjugate is cytotoxic to cells expressing more than 2000 type 2 VEGF receptors per cell. Examples of cells that are susceptible to the claimed conjugate include prostate tumor cells, breast cancer cells and bladder tumor cells.

In another embodiment, there is provided a method of using the conjugates of the present invention to kill cells expressing type 1 VEGF receptors. The conjugate can bind to both VEGF receptor type 1 (Flt-1) and VEGF receptor type 2 (KDR/Flk-1) but is internalized by VEGF receptor type 1 expressed on the cells. Examples of cells that are susceptible to the claimed conjugate include osteoclast precursor cells.

In yet another embodiment, there is provided a method of using the claimed conjugates to inhibit tumor growth, metastatic spread or vascularization of metastases in a subject. As used herein, a "subject" refers to an animal or a human. The method involves using a biologically effective amount of the claimed conjugates to exert cytotoxic effect on the tumor vasculature. The method may further comprise treatment with chemotherapeutic agents or radiotherapeutic agents well known in the art.

The present invention further provides methods of using the claimed conjugates to inhibit osteoclastogenesis, angiogenesis or to treat bone disease such as osteoporosis and osteoarthritis in an animal or a human.

In yet another embodiment, there is provided a method of inducing a cytotoxic effect or an anti-tumor effect such as inhibition of tumor growth, metastatic spread or vascularization of metastases. The method comprises the step of inducing expression of one or more genes listed in Table 4.

The following examples are given for the purpose of illustrating various embodiments of the invention and are not meant to limit the present invention. The present examples, along with the methods, procedures, treatments, and specific compounds described herein are representative of preferred embodiments. One skilled in the art will appreciate that the present invention is well adapted to carry out the objects and obtain the advantages mentioned, as well as those objects, ends and advantages inherent herein. Changes therein and other uses which are encompassed within the spirit of the invention as defined by the scope of the claims will occur to those skilled in the art.

EXAMPLE 1

Cell Lines and Reagents

Endothelial cell growth supplement from bovine neural tissue was obtained from Sigma. Murine brain endothelioma bEnd.3 cells were provided by Werner Risau (Max Plank Institute, Munich, Germany). Porcine aortic endothelial cells (PAE) transfected with either the human FLT-1 receptor (PAE/FLT-1) or the KDR receptor (PAE/KDR) were provided by Dr. J. Waltenberger. Soluble mouse Flk-1 was expressed in Sf9 cells as described by Warren et al. (1995). The human melanoma A-375 M cell line, human breast cancer SKBR3-HP, and HuT-78 cells were obtained from American Type Culture Collection. Tissue culture reagents were from GIBCO/BRL or Mediatech Cellgro (Herndon, Va.).

Rabbit anti-gelonin antisera was obtained from the Veterinary Medicine Core Facility at M. D. Anderson Cancer Center. Anti-flt-1 (sc-316), anti-flk-1 (sc-504), and anti-PARP (sc-8007) antibodies were purchased from Santa Cruz Biotechnology, Inc. (Santa Cruz, Calif.). BALB/c nude mice were purchased from The Jackson Laboratory and maintained under sterile pathogen-free conditions according to American Association of Laboratory Animal Care standards.

Anti-granzyme B mouse monoclonal antibody, and anti-caspase antibodies were obtained from Santa Cruz Biotechnology (Santa Cruz, Calif.). Horseradish peroxidase-goat anti-mouse (HRP-GAM) or anti-rabbit conjugate were purchased from Bio-Rad (Hercules, Calif.). FITC-coupled anti-mouse IgG was obtained from Sigma Chemical Co. (St. Louis, Mo.). Cytochrome c release apoptosis assay kit was purchased from Oncogene Research Products (Boston, Mass.). In situ cell death detection kit, AP [terminal deoxynucleotidyl transferase-mediated nick end labeling (TUNEL) assay], and Fast Red were from Roche Molecular Biochemicals (Indianapolis, Ind.).

The PCR reagents were obtained from Fisher Scientific, and the molecular biology enzymes were purchased from Roche Molecular Biochemicals or New England Biolabs. Bacterial strains, pET bacterial expression plasmids, and recombinant enterokinase were obtained from Novagen. All other chemicals were obtained from Sigma or Fisher Scientific. Metal affinity resin (Talon) was obtained from CLONTECH. Other chromatography resin and materials were purchased from Amersham Pharmacia.

EXAMPLE 2

Construction of $VEGF_{121}$/rGelonin Fusion Toxin

The cDNA encoding human $VEGF_{121}$ and recombinant gelonin were fused together by using the splice overlap extension PCR method with VEGF and gelonin DNA as templates. Primers used were: VEGF Nterm, (5'-TGGTCCCAGGCTCATATGGCA CCCATGGCAGAA-3', SEQ ID NO:1); VEGF Cterm, (5'-TCTAGACCGGAGCCACCGCCAC-CCCGCCTCGGCTTGTC-3', SEQ ID NO:2); Gel Nterm, (5'-GGTGGCGGTGG CTCCGGTCTAGACACCGT-GAGC-3', SEQ ID NO:3); Gel Cterm, (5'-AAGGCTCGT-GTCGACCTCGAGTCATTAAGCTTTAGGAT CTTTATC-3', SEQ ID NO:4). A G4S linker was incorporated between the $VEGF_{121}$ and the rGel sequences. Purified PCR products were digested with the restriction enzymes BspHI and XhoI and ligated into pET-32a. The constructs were transformed into *Escherichia coli* strain AD494 (DE3) pLys S for expression of the fusion protein.

The combination of $VEGF_{121}$ and recombinant gelonin was originally prepared in two different orientations (FIG. 1) with both orientations displaying similar cytotoxicity profiles. However, the orientation with $VEGF_{121}$ at the N-terminus results in a higher yield following purification from bacteria, and is used in subsequent experiments.

EXAMPLE 3

$VEGF_{121}$/rGelonin Expression in *E. coli* and Purification

The expression and purification of $VEGF_{121}$/rGel has been previously described (Veenendaal et al., 2002). Bacterial colonies transformed with the plasmid carrying the $VEGF_{121}$/rGel insert were cultured in LB growth medium (Sigma) containing 200 mg/ml ampicillin, 70 mg/ml chloramphenicol, and 15 mg/ml kanamycin at 37° C. overnight in a shaker bath at 240 rpm. The cultures then were diluted 1:20 with fresh LB medium with antibiotics and grown to early log phase (A600/0.6) at 37° C. Thereafter, the cultures were diluted 1:1 with fresh LB medium plus antibiotics. Protein synthesis was induced at 23° C. by the addition of 0.1 mM isopropyl b-D-thiogalactoside (IPTG) overnight. The cells were collected by centrifugation, resuspended in 10 mM Tris/HCl (pH 8.0), and frozen.

The fusion protein was expressed and purified from bacterial supernatant. *E. coli* cells were lysed with 100 ml 0.1 mm glass beads (BioSpec Products, Inc) in a Bead Beater (BioSped Products, Inc) for eight cycles of 3 minutes each. The lysate was ultracentrifuged at 40,000 rpm for 90 minutes at 4° C. The supernatant was carefully collected and adjusted to 40 mM Tris-HCl (pH 8.0), 300 mM NaCl, and incubated at 4° C. with metal affinity resin. The resin was washed with 40 mM Tris-HCl (pH8.0), 0.5 M NaCl buffer containing 5 mM Imidazole and eluted with buffer containing 100 mM Imidazole. After pooling fractions containing $VEGF_{121}$/rGel, the sample was dialyzed against 20 mM Tris (pH 8.0), 200 mM NaCl and digested with recombinant Enterokinase at room temperature. Enterokinase was removed by agarose-linked soybean trypsin inhibitor. Other proteins of non-interest were removed by Q Sepharose Fast Flow resin and metal affinity resin as described previously[26]. $VEGF_{121}$/rGel was concentrated and stored in sterile PBS at −20° C.

SDS/PAGE analysis of protein expression after induction with IPTG showed a new protein at 62 kDa, which is the expected molecular weight for the fusion protein plus the 21 kDa purification tag. This material was purified by binding and elution from IMAC resin. Cleavage with recombinant enterokinase removed the tag resulting in a 42-kDa protein under reducing conditions. The construct migrated as a homodimer at 84 kDa under nonreducing conditions. The fusion construct was immunoreactive with antibodies to both VEGF and rGel. One liter of induced bacterial culture initially contained ~2,000 mg of soluble fusion construct. Initial IMAC purification resulted in 750 mg of $VEGF_{121}$/rGel product (yield 37.5%), and digestion with recombinant enterokinase generated 400 mg of target protein (yield 20%). Subsequent purification yielded 230 mg of $VEGF_{121}$/rGel final product (11.5% overall yield).

EXAMPLE 4

Anti-VEGF and Anti-rGel Western Blot Analysis

Protein samples were analyzed by SDS/15% PAGE under reducing conditions. The gel was electrophoretically transferred to nitrocellulose overnight at 4° C. in transfer buffer (25 mM Tris/HCl, pH 7.6/190 mM glycine/20% HPLC-grade methanol). The membranes were blocked by the addition of 5% BSA in Western blocking buffer [(TBS)/Tween] and then incubated for 1 h with rabbit anti-gelonin polyclonal antibody (2 mg/ml in TBS/Tween) or mouse anti-VEGF monoclonal antibody 2C3 (2 mg/ml in TBS/Tween). The membrane then was incubated with goat-anti-rabbit IgG horseradish peroxidase (HRP) or goat-anti-mouse IgG-HRP (1:5,000 dilution in TBS/Tween). Then, the membrane was developed with the Amersham Pharmacia enhanced chemiluminescence (ECL) detection system and exposed to x-ray film.

EXAMPLE 5

Biological Activity of the rGel Component

The functional activity of rGel and $VEGF_{121}$/rGel were assayed by using a cell-free protein translation inhibition assay kit from Amersham Pharmacia as described by the manufacturer. As determined by the rabbit reticulocyte translation assay, the purified $VEGF_{121}$/rGel and rGel had $IC_{50}$ values of ~47 and 234 pM, respectively, showing that fusion of rGel and $VEGF_{121}$ did not reduce the activity of the toxin component (FIG. 2).

EXAMPLE 6

Binding of $VEGF_{121}$/rGelonin to Soluble Flk-1 Receptor

Binding to Flk-1 was tested on microtiter plates coated with soluble mouse Flk-1. Plates were treated with 2 mg/ml of NeutrAvidin (Pierce) for 6 h. Purified, biotinylated Flk-1 (Warren et al., 1995) was incubated with NeutrAvidin-coated wells for 2 h. $VEGF_{121}$ or $VEGF_{121}$/rGel was added to the wells at various concentrations in the presence of PBS containing 2% (vol/vol) BSA. After 2 h of incubation, plates were washed and incubated with nonblocking mouse monoclonal anti-VEGF antibody, 2C3 (Brekken et al., 1998), or rabbit polyclonal anti-gelonin IgG. For competition studies of $VEGF_{121}$/rGel and $VEGF_{121}$, binding of the $VEGF_{121}$/rGel fusion protein was detected by using a rabbit anti-gelonin antibody. Mouse and rabbit IgG were detected by HRP-labeled goat anti-mouse and anti-rabbit antibodies, respectively (Dako). Peroxidase activity was measured by adding O-phenylenediamine (0.5 mg/ml) and hydrogen peroxide (0.03% vol/vol) in citrate-phosphate buffer (pH 5.5). The reaction was stopped by the addition of 100 ml of 0.18 M of $H_2SO_4$. The absorbance was read at 490 nM. In competition experiments, a 10-fold molar excess of $VEGF_{121}$ was premixed with $VEGF_{121}$/rGel before addition to the plate.

Figure 3:
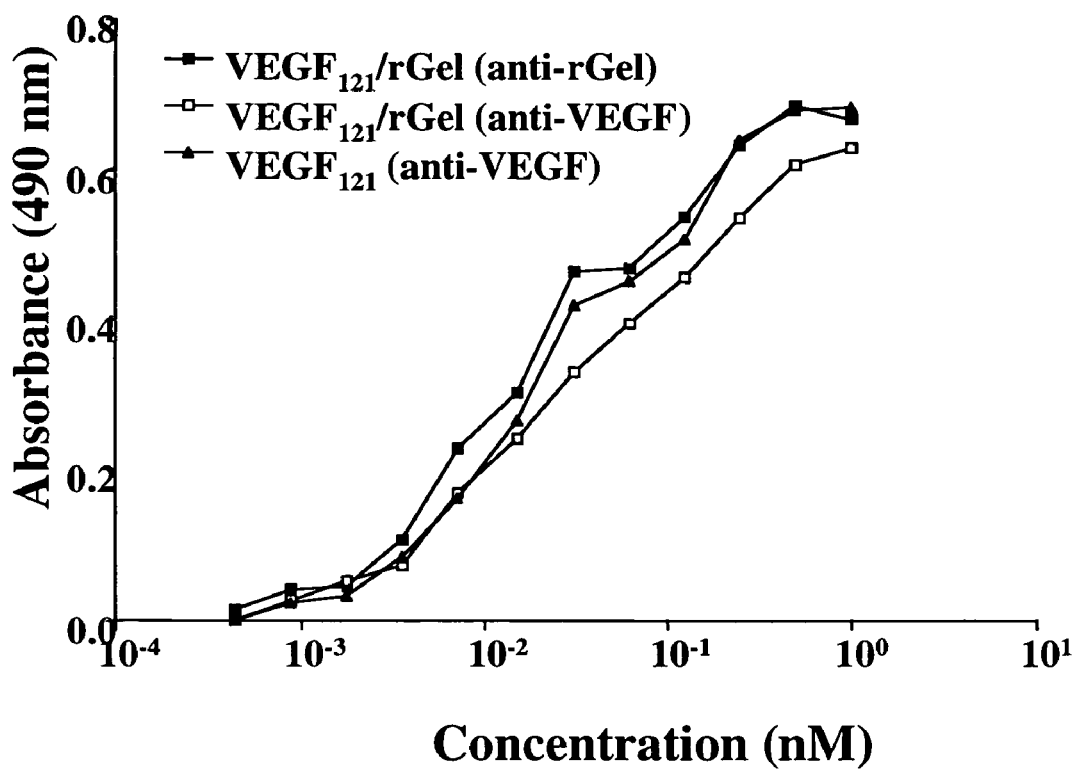
FIG. 3 shows an ELISA demonstrating that $VEGF_{121}$/rGel binds to the receptor. $VEGF_{121}$/rGel, $VEGF_{121}$ and rGel were incubated with biotinylated mouse flk-1 receptor attached to NeutrAvidin-coated plates. Binding was assessed using anti-gelonin and anti-VEGF antibodies.
Figure 4:
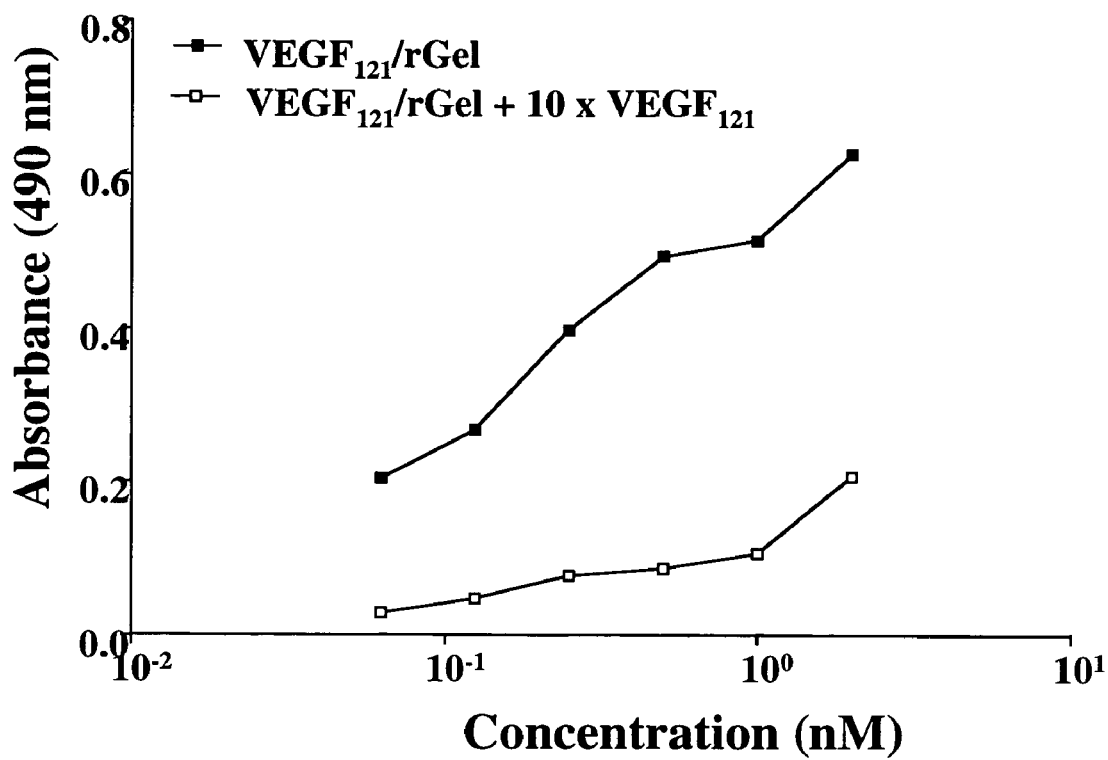
FIG. 4 shows binding to flk-1 receptor is specific for $VEGF_{121}$/rGel. $VEGF_{121}$/rGel or $VEGF_{121}$ was incubated with flk-1 receptor. Binding of $VEGF_1$/rGel was competed with $VEGF_{121}$ and a rabbit anti-gelonin antibody was used for detection. $VEGF_{121}$ specifically reduced binding of $VEGF_{121}$/rGel to flk-1. $VEGF_{121}$ was not detected by the anti-gelonin antibody (data not shown).

As shown in FIG. 3, $VEGF_{121}$/rGel and native human $VEGF_{121}$ bind equally well to Flk-1 at all concentrations, indicating that the VEGF component of the fusion protein is fully capable of binding to Flk-1. The specificity of binding of $VEGF_{121}$/rGel to Flk-1 was confirmed by using a 10-fold molar excess of free $VEGF_{121}$ (FIG. 4).

EXAMPLE 7

$VEGF_{121}$/rGelonin and $VEGF_{121}$-Induced Phosphorylation of KDR

Porcine aortic endothelial cells (PAE/KDR) overexpressing the kinase domain receptor (KDR) were incubated overnight in F-12 culture medium and then incubated at 37° C. for 5 min with 100 mM Na3 VO4. VEGF or $VEGF_{121}$/rGel then were added and, at various times, cells were lysed by the addition of a lysis buffer (50 mM Hepes, pH 7.4/150 mM NaCl/1 mM EGTA/10 mM sodium pyrophosphate/1.5 mM MgCl2/100 mM NaF/10% (vol/vol) glycerol/1% Triton X-100). Cell lysates were centrifuged (16,000×g), the supernatants were removed, and their protein concentrations were determined. Lysate supernatants were incubated with 9 mg anti-phosphotyrosine monoclonal antibody (Santa Cruz Biotechnology) for 2 h at 4° C. and then precipitated by the addition of Protein A Sepharose beads for 2 h at 4° C. Beads were washed and mixed with SDS sample buffer, heated for 5 min at 100° C., centrifuged, analyzed by SDS/10% PAGE, and then transferred to nitrocellulose filters. The membranes were blocked with 5% nonfat dry milk and incubated with rabbit polyclonal anti-KDR antibody (1:250; Santa Cruz Biotechnology) for 1 h at room temperature. The membranes then were washed, incubated with a peroxidase-linked goat anti-rabbit antibody (1:2,000) for 1 h at room temperature, and then enhanced chemiluminescence reagent (Amersham Pharmacia) was used to visualize the immunoreactive bands.

Results from these experiments showed that addition of $VEGF_{121}$/rGel or $VEGF_{121}$ increased phosphotyrosine content. There were two phases of phosphorylation; an early phase (1-10 min) and a later phase (4-8 h). The time course of induction of KDR phosphorylation was the same for $VEGF_{121}$/rGel and $VEGF_{121}$. Phosphorylation of FLT-1 in PAE/FLT-1 cells treated with either $VEGF_{121}$/rGel or $VEGF_{121}$ was not observed, as expected from the weaker signaling of FLT-1 compared with KDR observed by others.

Although $VEGF_{121}$/rGel induces phosphorylation of KDR receptor, no growth-stimulatory effects of the fusion toxin on VEGF receptor-expressing cells were observed. These findings are in keeping with studies of other fusion toxins such as IL-2/DT that initially stimulate target cells in a manner similar to that of IL-2 itself, but ultimately kill the target cells through the actions of the internalized toxin.

EXAMPLE 8

Cytotoxicity of $VEGF_{121}$/rGelonin to Endothelial Cells in Vitro

To determine cytotoxicity on adult bovine aortic arch-derived endothelial cells (ABAE), log-phase adult bovine aortic arch-derived endothelial cells in DMEM [10% (vol/vol) FBS] were diluted to 4,000 cells per 200 ml. Aliquots (200 ml) were added to 96-well flat-bottomed tissue culture plates and incubated at 37° C. for 1-72 h in 5% $CO_2$. Purified $VEGF_{121}$/rGel or rGel were diluted in culture medium to various concentrations, added to the plate, and the cultures were incubated for 72 h. Remaining adherent cells were stained by the addition of 100 ml of crystal violet [0.5% in 20% (vol/vol) methanol]. Dye-stained cells were solubilized by the addition of 100 ml of Sorenson's buffer [0.1M sodium citrate, pH 4.2 in 50% (vol/vol) ethanol]. The absorbance was measured at 595 nM.

To determine cytotoxicity on mouse brain-derived endothelial cells bEnd.3, the cells were seeded at a density of 50,000/well in 24-well plates. Twenty-four hours later, $VEGF_{121}$/rGel or rGel alone were added at various concentrations. After 5 days of treatment at 37° C., remaining attached cells were trypsinized and counted. The results are presented as total cell number per well. Two identical experiments were performed in duplicate. Standard error in all experiments was less than 5% of the mean.

To determine cytotoxicity on PAE/KDR and PAE/FLT-1 cells, log-phase PAE/KDR cells and PAE/FLT-1 cells in F-12 medium [10% (vol/vol) FBS] were diluted to 3,000 cells per 200 ml. Aliquots (200 ml) were added to 96-well flat-bottomed tissue culture plates and incubated at 37° C. for 24 h in 5% $CO_2$. Purified $VEGF_{121}$/rGel or rGel were diluted in culture medium, added to the plate, and incubated for 72 h. Adherent cells were quantified by using the crystal violet staining method described above.

Figure 5:
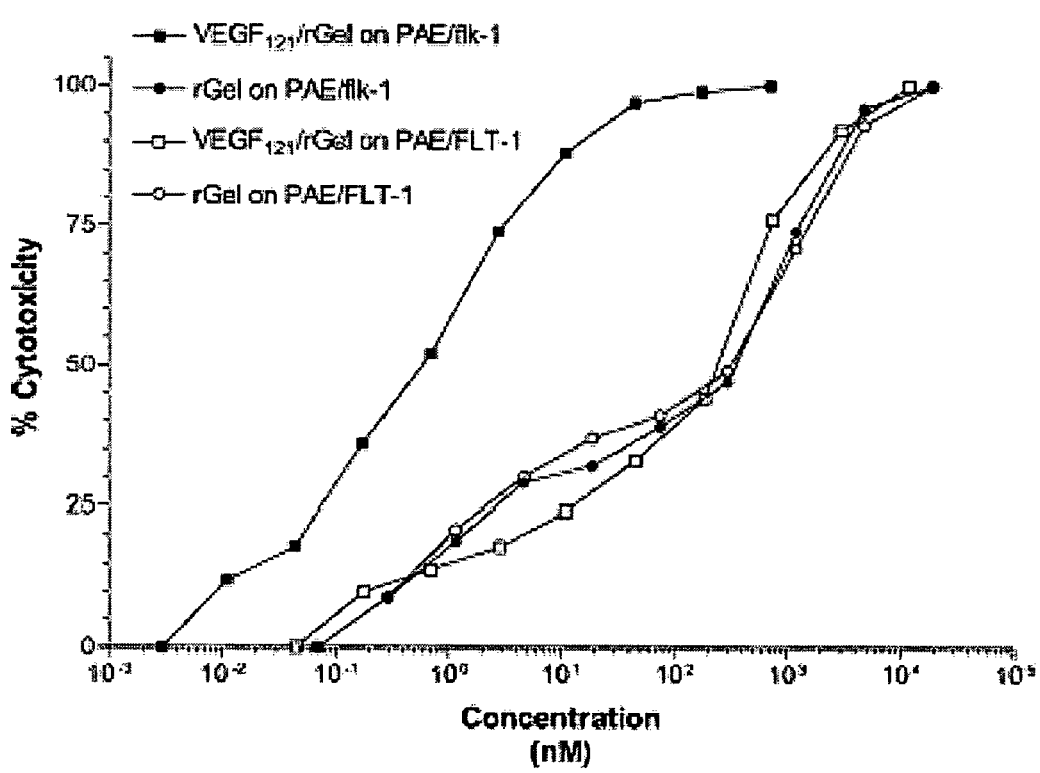
FIG. 5 shows cytotoxicity of $VEGF_{121}$/rGel to KDR-expressing porcine aortic endothelial cells (PAE). Cells transfected with either the FLT-1 or KDR receptor were treated with various doses of $VEGF_{121}$/rGel or rGel for 72 h. Cells expressing the FLT-1 receptor were equally insensitive to $VEGF_{121}$/rGel and rGel ($IC_{50}$/300 nM). In contrast, cells expressing KDR were about 200-fold more sensitive to the fusion construct ($IC_{50}$ of 0.5 nM) than they were to rGel.

$VEGF_{121}$/rGel was specifically toxic to KDR/Flk-1 expressing endothelial cells in vitro (FIG. 5 and Table 1). The $IC_{50}$ values for $VEGF_{121}$/rGel on log-phase PAE/KDR, ABAE, and bEnd.3 cells, which express $1-3\times10^5$ KDR/Flk-1 receptors per cell, was 0.06 to 1 nM. Cells expressing FLT-1 and having low endogenous expression of KDR (PAE/FLT-1, HUVEC) were several hundred-fold more resistant to $VEGF_{121}$/rGel than were the KDR/Flk-1 expressing cells. Thus, FLT-1 appears not to mediate cytotoxicity of $VEGF_{121}$/rGel.

The ratio of $IC_{50}$ values of rGel to $VEGF_{121}$/rGel was calculated for each cell type. This ratio (the targeting index) represents the ability of the VEGF component of the fusion construct to mediate the delivery of the toxin to the endothelial cell surface and into the intracellular ribosomal compartment. As summarized in Table 1, bEnd.3 and adult bovine aortic arch-derived endothelial cells were, respectively, 100-fold and 9-fold more sensitive to the fusion construct than they were to free rGel.

TABLE 1

Number of VEGF Receptors Per Cell And Sensitivity To $VEGF_{121}$/rGelonin

| Cell Type | Number of FLT-1 sites per cell | Number of KDR sites per cell | $IC_{50}$ for $VEGF_{121}$/ rGel (nM) | $IC_{50}$ for rGel (nM) | Targeting index* |
|---|---|---|---|---|---|
| PAE/KDR (log phase) | 0 | $2-3 \times 10^5$ | 0.5 | 300 | 600 |

TABLE 1-continued

Number of VEGF Receptors Per Cell And Sensitivity To VEGF$_{121}$/rGelonin

| Cell Type | Number of FLT-1 sites per cell | Number of KDR sites per cell | IC$_{50}$ for VEGF$_{121}$/ rGel (nM) | IC$_{50}$ for rGel (nM) | Targeting index* |
|---|---|---|---|---|---|
| PAE/KDR (confluent) | 0 | 2-3 × 10$^5$ | 30 | 5000 | 167 |
| bEnd3 (log phase) | Not done | 2 × 10$^5$ | 1 | 100 | 100 |
| ABAE (log phase) | 0 | 0.4 × 10$^5$ | 0.059 | 0.524 | 8.9 |
| HUVEC (hypoxia) | Not done | 0.023 × 10$^5$ | 700 | >1000 | ~1 |
| HUVEC (normoxia) | Not done | 0.017 × 10$^5$ | 800 | >1000 | ~1 |
| PAE/FLT-1 (log phase) | 0.5 × 10$^5$ | Not done | 300 | 300 | 1 |
| PAE/FLT-1 (confluent) | 0.5 × 10$^5$ | Not done | >5000 | 10000 | <2 |
| A-375 (log phase) | Not done | Not done | 330 | 109 | 0.3 |
| PC-3 (log phase) | Not done | Not done | 225 | 100 | 0.4 |

*Targeting index is defined as the ratio of IC$_{50}$ of rGel to VEGF$_{121}$/rGel.

EXAMPLE 9

Selective Cytotoxicity of VEGF$_{121}$/rGelonin for Dividing PAE/KDR Cells

VEGF$_{121}$/rGel was 60-fold more toxic to PAE/KDR cells in log-phase growth than it was to PAE/KDR cells that had been grown to confluence and rested (Table 1). This effect was not caused by differences in KDR expression, because the cells expressed the same number of KDR receptors per cell in both phases of growth. The log-phase PAE/KDR cells also were more sensitive to rGel itself than were the confluent cells, suggesting that the quiescence of confluent cells impacts their sensitivity to both targeted and nontargeted rGel. It is possible that the rate or route of entry of both VEGF$_{121}$/rGel and rGel is different for dividing and nondividing cells.

EXAMPLE 10

VEGF$_{121}$/rGelonin Binds to Both KDR and FLT-1

VEGF$_{121}$, has been shown to bind to the FLT-1 receptor with greater affinity than to KDR. Because cytotoxicity of VEGF$_{121}$/rGel to KDR-expressing cells was found to be nearly 600-fold greating than for FLT-1 expressing cells, the relative binding of VEGF$_{121}$/rGel to PAE cells expressing each of the receptors was investigated.

ELISA analysis was performed to confirm the expression of both receptors on the cell surface using receptor-specific antibodies (data not shown). Expression of VEGFR-1 (FLT-1) and VEGFR-2 (KDR) was confirmed by western blot (FIG. 6A). Whole cell lysates of PAE/KDR and PAE/FLT-1 cells were obtained by lysing cells in Cell Lysis buffer (50 mM Tris, pH 8.0, 0.1 mM EDTA, 1 mM DTT, 12.5 mM MgCl$_2$, 0.1 M KCl, 20% glycerol) supplemented with protease inhibitors (0.5% leupeptin, 0.5% aprotinin and 0.1% PMSF). Protein samples were separated by SDS-PAGE under reducing conditions and electrophoretically transferred to a PVDF memberane overnight at 4$^B$C in transfer buffer (25 mM Tris-HCl, pH 7.6, 190 mM glycine, 20% HPLC-grade methanol). The samples were analyzed for KDR with rabbit anti-flk-1 polyclonal antibody and FLT-1 using an anti-flt-1 polyclonal antibody. The membranes were then incubated with goat-anti-rabbit IgG horseradish peroxidase (HRP), developed using the Amersham ECL detection system and exposed to X-ray film.

In order to confirm that VEGF$_{121}$/rGel bound to human VEGFR-1 and VEGFR-2 and that the presence of recombinant gelonin did not interfere with the binding properties of VEGF$_{121}$, the binding of radiolabeled VEGF$_{121}$/rGel to both KDR and FLT-1 receptors expressed on the surface of PAE cells was investigated. One hundred μg of VEGF$_{121}$/rGel was radiolabeled with 1mCi of NaI$^{125}$ using Chloramine T$^{27}$ for a specific activity of 602 Ci/mMol. Cells were grown overnight in 24-well plates. Non-specific binding sites were blocked for 30 minutes with PBS/0.2% gelatin followed by incubation for 4 hours with $^{125}$I-VEGF$_{121}$/rGel in PBS/0.2% gelatin solution. For competition experiments, cold VEGF$_{121}$/rGel or gelonin were pre-mixed with $^{125}$I-VEGF$_{121}$/rGel. Cells were washed four times with PBS/0.2% gelatin solution, detached and bound cpm was measured.

FIG. 6B shows that the binding of $^{125}$I-VEGF$_{121}$/rGel to both cells was nearly identical. Binding of VEGF$_{121}$/rGel to both PAE/KDR and PAE/FLT-1 cells was competed by unlabeled VEGF$_{121}$/rGel but not by unlabeled gelonin, indicating that binding of VEGF$_{121}$/rGel was mediated by VEGF$_{121}$.

EXAMPLE 11

Internalization of VEGF$_{121}$/rGelonin into PAE/KDR Cells

The internalization of VEGF$_{121}$/rGel into PAE/KDR and PAE/FLT-1 cells was investigated using immunofluorescence staining. PAE/KDR and PAE/FLT-1 cells were incubated with 4 μg/ml VEGF$_{121}$/rGel at various time points. After stripping the cell surface, cells were fixed with 3.7% formaldehyde and permeabilized with 0.2% Triton X-100. Non-specific binding sites were blocked with 5% BSA in PBS. Cells were then incubated with a rabbit anti-gelonin polyclonal antibody (1:200) followed by a TRITC-conjugated anti-rabbit secondary antibody (1:80). Nuclei were stained with propidium iodide (1 μg/ml) in PBS. The slides were fixed with DABCO media, mounted and visualized under fluorescence (Nikon Eclipse TS1000) and confocal (Zeiss LSM 510) microscopes.

VEGF$_{121}$/rGel was detected in PAE/KDR cells within 1 hour of treatment with the immunofluoresence signal progressively increasing to 24 hours (FIG. 7). As expected, cell density also decreased over the 24 hour time period. No VEGF$_{121}$/rGel was detected in PAE/FLT-1 cells up to 24 hours after treatment with the fusion toxin. Treatment of cells with the same concentration of rGelonin showed no internalization, confirming that entry of VEGF$_{121}$/rGel into PAE cells was specifically via the KDR receptor.

EXAMPLE 12

Cytotoxic Effects of VEGF$_{121}$/rGelonin as a Function of Exposure Time on Endothelial Cells The IC$_{50}$ of VEGF$_{121}$/rGel incubated for 72 hours on log-phase PAE/KDR cells has been shown to be about 1 nM. However, VEGF$_{121}$/rGel internalizes into these cells within one hour of incubation. To study the cytototoxic effect of VEGF$_{121}$/rGel as a function of exposure time of this agent on endothelial cells, cells were incubated with VEGF$_{121}$/rGel from 1-72 hours and its cytotoxicity on PAE/KDR cells was assessed at the end of the 72-hour period.

Figure 8:
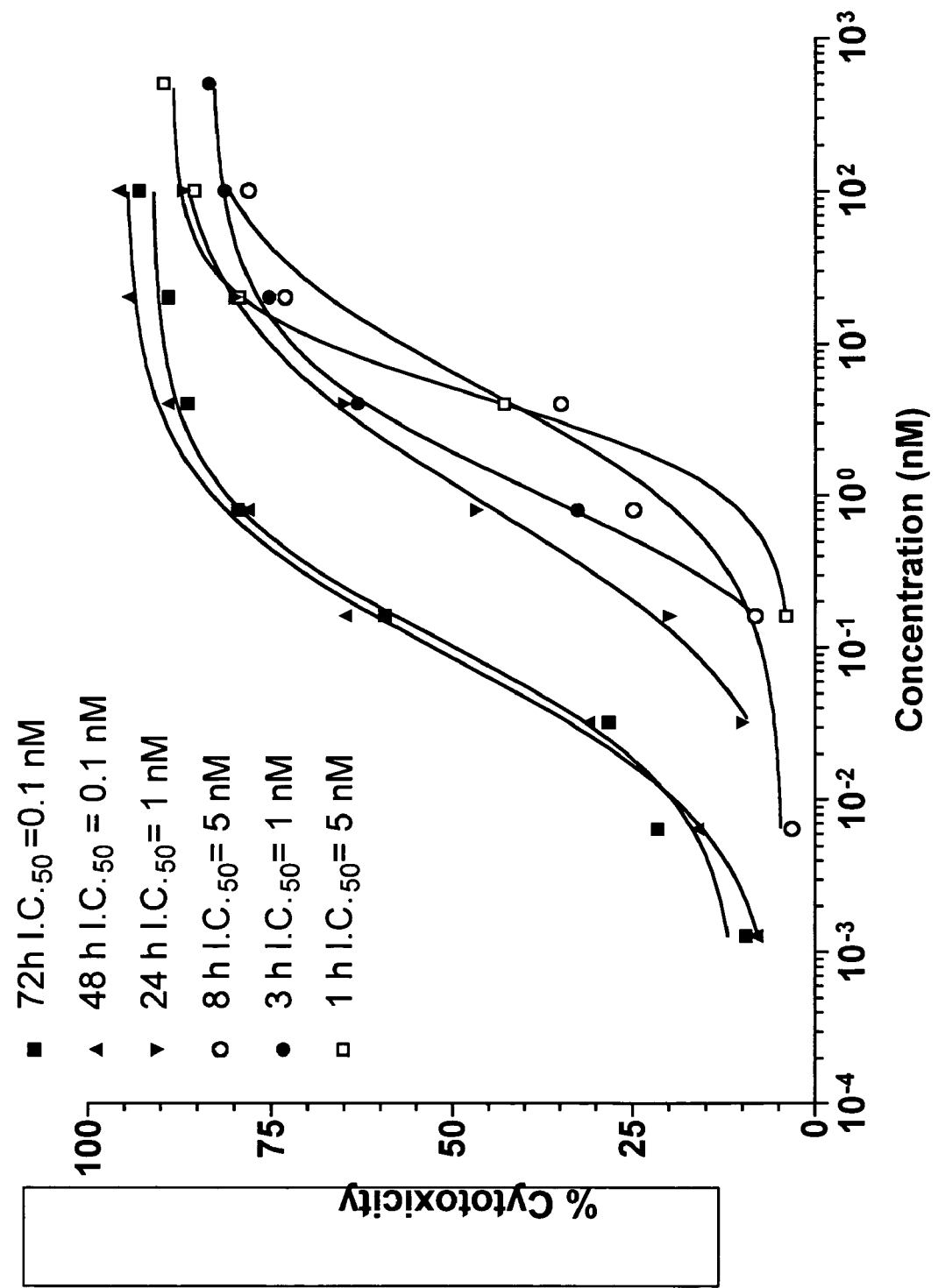
FIG. 8 shows the effect of exposure time of $VEGF_{121}$/rGel on PAE/KDR cells on cytotoxicity. $VEGF_{121}$/rGel was incubated with PAE/KDR cells for varying lengths of time. While $VEGF_{121}$/rGel retained cytotoxicity towards PAE/KDR cells even with a 1 h exposure time, cytotoxicity of this fusion toxin was markedly enhanced by an exposure time of 48 hours.

While VEGF$_{121}$/rGel retained cytotoxicity even after a one hour incubation, appreciable cytotoxicity was observed after 24 hours and maximal cytotoxic effect of VEGF$_{121}$/rGel on PAE/KDR cells was observed after 48 hours (FIG. 8). The cytotoxic effect of VEGF$_{121}$/rGel on PAE/FLT-1 cells was also affected as a function of exposure duration (data not shown).

EXAMPLE 13

Cytotoxic Mechanism of VEGF$_{121}$/rGelonin

In order to investigate the mechanism of cytotoxicity of VEGF$_{121}$/rGel to PAE/KDR cells, a TUNEL assay was performed for 24, 48 and 72 hours. Log phase PAE/KDR and PAE/FLT-1 cells were diluted to 2000 cells/100 µl. Aliquots (100 µl) were added in 16-well chamber slides (Nalge Nunc International) and incubated overnight at 37° C. with 5% CO$_2$. Purified VEGF$_{121}$/rGel was diluted in culture media and added at 72, 48 and 24 hour time points at a final concentration of 1 nM (twice the IC$_{50}$). The cells were then processed and analyzed for TUNEL as described by the manufacturer of the reagent. Positive control cells were incubated with 1 mg/ml DNAse for 10 minutes at 37° C.

No TUNEL staining was observed with PAE/KDR cells exposed to VEGF$_{121}$/rGel up to 72 hours (FIG. 9). In contrast nuclei of positive control cells showed intense staining, indicating that the mechanism of cytotoxicity of VEGF$_{121}$/rGel is not apoptotic.

Figure 10:
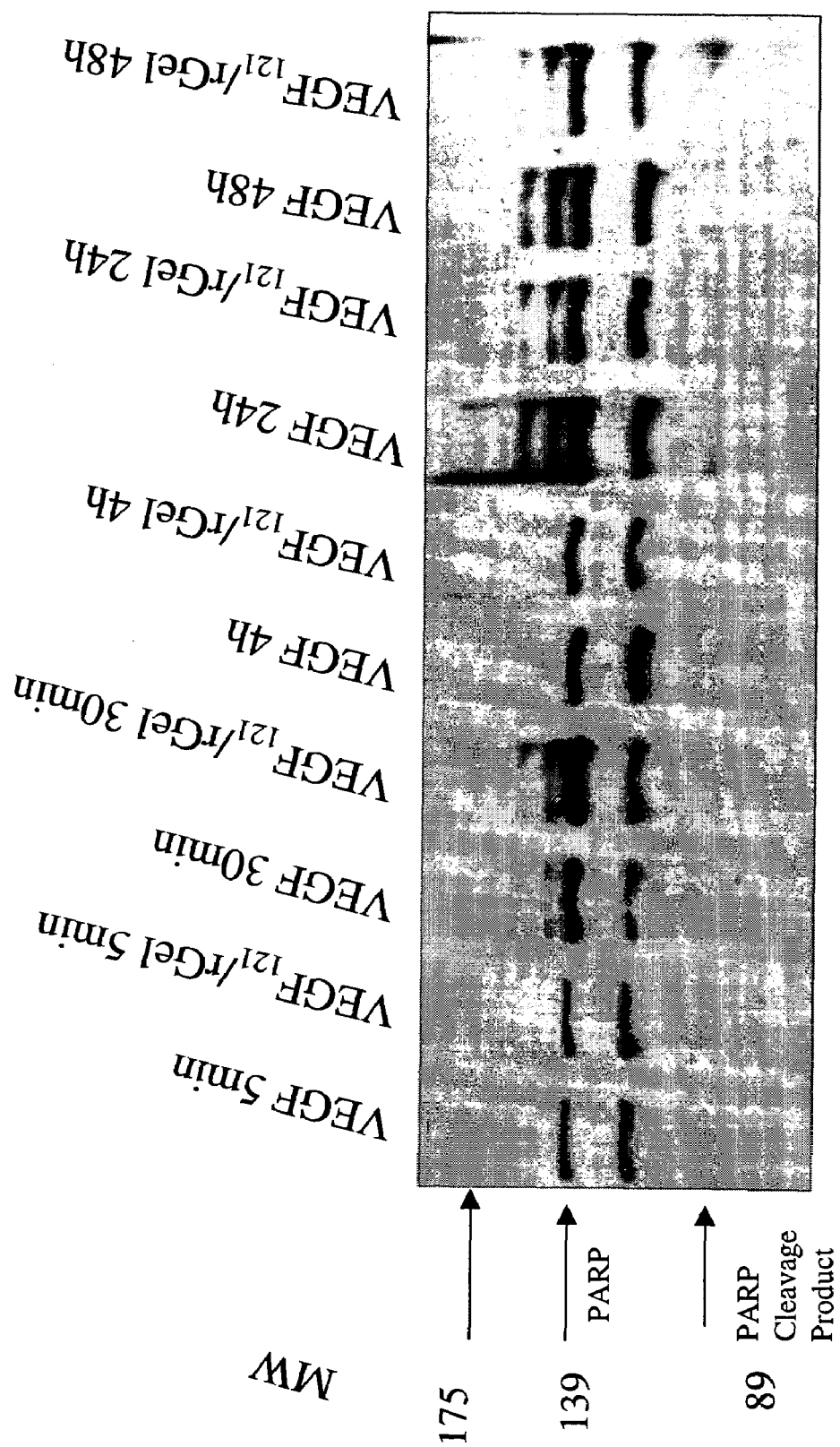
FIG. 10 shows that treatment of PAE/KDR cells with $VEGF_{121}$/rGel does not result in PARP cleavage. PAE/KDR cells were stimulated with $VEGF_{121}$/rGel or $VEGF_{121}$ for the times indicated. Cells were washed and lysed and the cell lysate was analyzed by Western using an anti-PARP antibody. No PARP cleavage was observed.

Effects of VEGF$_{121}$/rGel on PARP-mediated apoptosis were investigated by pre-incubating PAE/KDR cells with 100 mM Na$_2$VO$_4$ for 5 minutes at 37° C. followed by stimulation with VEGF$_{121}$/rGel or VEGF$_{121}$ for 5 minutes, 30 minutes, 4 h, 24 h and 48 h. Cells were washed and lysed. Cell lysate was analyzed by Western using an anti-PARP antibody. Western blot analysis of these cells showed that VEGF$_{121}$/rGel did not activate PARP-mediated apoptosis (FIG. 10).

EXAMPLE 14

Inhibition of Tumor Growth in vivo by VEGF$_{121}$/rGelonin

Human melanoma xenograft model was established as follows. Female nu/nu mice were divided into groups of five mice each. Log-phase A-375M human melanoma cells were injected s.c. (5×10$^6$ cells per mouse) into the right flank. After the tumors had become established (~50 mm$^3$), the mice were injected with VEGF$_{121}$/rGel through a tail vein five times over an 11 day period. The total dose of VEGF$_{121}$/rGel was 17 or 25 mg/kg. Other mice received rGel alone at a dose totaling 10 mg/kg. Mice were killed by cervical dislocation after the 40th day of tumor measurement.

Human prostate cancer xenograft model was established as follows. Male nude mice weighing ~20 g were divided into groups of five mice each. Log-phase PC-3 human prostate tumor cells were injected s.c. (5×10$^6$ cells per mouse) in the right flank. The mice were injected with VEGF$_{121}$/rGel through a tail vein every 2-3 days for 11 days. The total dose of VEGF$_{121}$/rGel was 20 mg/kg. Other mice received rGel alone at a dose totaling 10 mg/kg. Tumor volume was calculated according to the formula: volume=L×W×H, where L=length, W=width, H=height.

Figure 11:
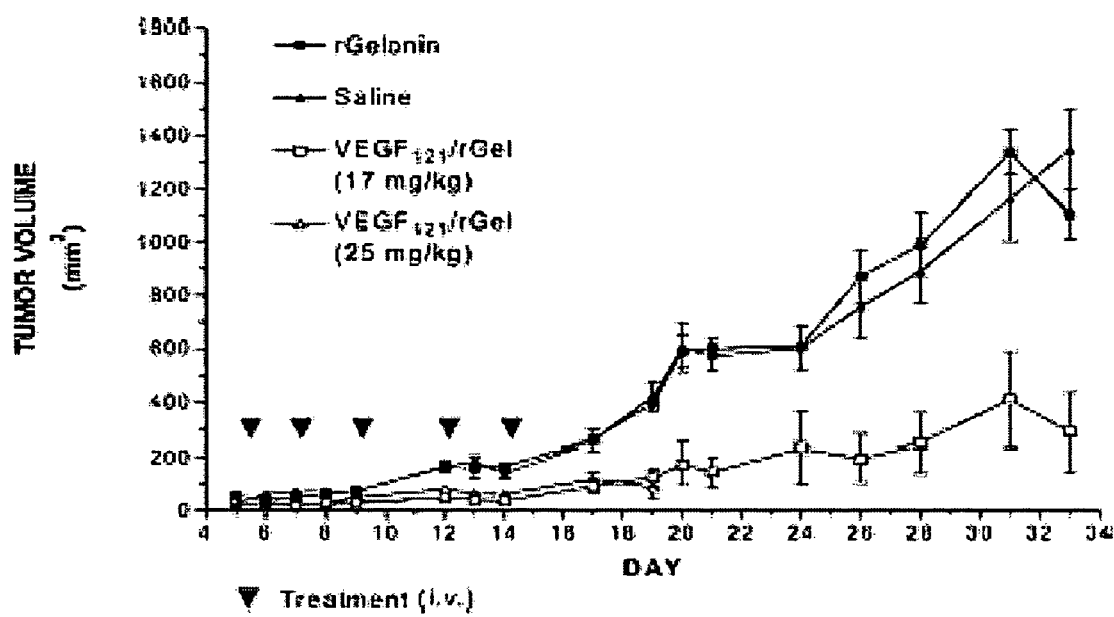
FIG. 11 shows inhibition of human melanoma growth in mice by VEGF/rGel. Groups of nude mice bearing A-375M tumors were treated intravenously with saline, rGel, or fusion construct every 2-3 days for 11 days. Administration of rGel did not affect tumor growth. Treatment with $VEGF_{121}$/rGel at a total dose of either 17 mg/kg or 25 mg/kg significantly suppressed tumor growth. However, treatment at the 25 mg/kg dose level resulted in mortality by day 19. None of the animals dosed at 17 mg/kg showed gross evidence of toxicity.

As shown in FIG. 11, saline-treated human melanoma A-375M tumors showed an increase in tumor volume 24-fold (from 50 mm$^3$ to 1200 mm$^3$) over the 30-day observation period. Treatment of the mice with VEGF$_{121}$/rGel strongly retarded tumor growth. At high doses of VEGF$_{121}$/rGel totaling 25 mg/kg, tumor growth was completely prevented, but all mice died from drug toxicity on day 19. At lower doses totaling 17 mg/kg, all mice survived. Tumor growth was completely prevented throughout the 14-day course of treatment, but thereafter, tumor regrowth slowly recurred. Compared with controls, mice treated with VEGF$_{121}$/rGel at doses totaling 17 mg/kg showed a 6-fold decrease in tumor volume (1,200 mm$^3$ vs. 200 mm$^3$).

Figure 12:
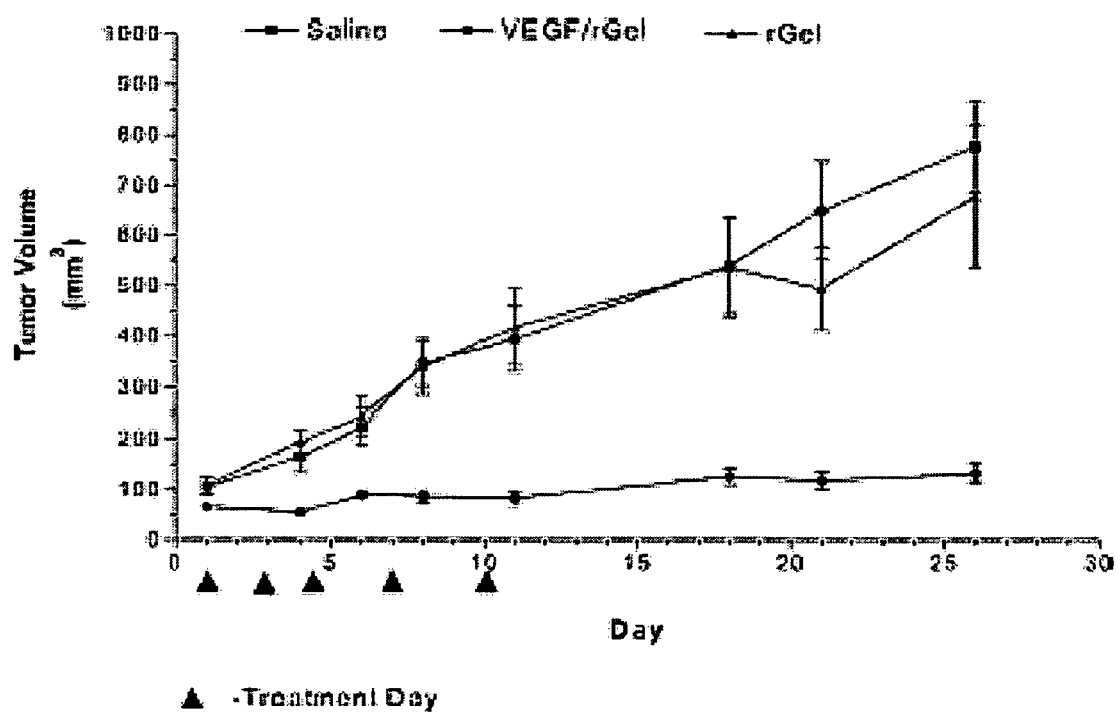
FIG. 12 shows inhibition of human prostate carcinoma growth in mice by VEGF/rGel. Groups of nude mice bearing PC-3 tumors were treated. intravenously with saline, rGel, or the $VEGF_{121}$/rGel fusion construct (20 mg/kg total dose) every 2-3 days for 11 days. Administration of rGel (10 mg/kg) had no effect on tumor growth. In contrast, treatment with the fusion construct completely inhibited tumor growth for 26 days and resulted in a 7-fold reduction in tumor volume compared with saline-treated or rGel-treated controls.

Human prostatic carcinoma (PC-3) tumors increased 12-fold in volume during the 26-day observation period (FIG. 12). Treatment of the mice with five doses of VEGF$_{121}$/rGel totaling 20 mg/kg virtually abolished tumor growth, even after cessation of treatment. Tumor volume in the treated group only increased from 100 to 200 mm$^3$ over the course of the experiment. Compared with controls, treatment with VEGF$_{121}$/rGel resulted in a 7-fold decrease in tumor volume (1,400 mm$^3$ vs. 200 mm$^3$).

EXAMPLE 15

Localization of VEGF$_{121}$/rGelonin to Vascular Endothelium in Prostate Tumor Xenografts Mice (three mice per group) bearing PC-3 human prostate tumors were injected intravenously with 50 ug of the fusion protein gelonin (2.5 mg/kg) or free gelonin (1 mg/kg). The mean tumor volume per group was 260 mm$^3$. Thirty minutes later, mice were killed, exsanguinated, and all major tissues were snap frozen. Frozen sections were cut and double stained with pan-endothelial marker MECA-32 (5 mg/ml) followed by detection of the localized fusion protein using rabbit anti-gelonin antibody (10 mg/ml). MECA-32 rat IgG was visualized with goat anti-rat IgG conjugated to FITC (red fluorescence). Anti-gelonin antibody was detected with goat anti-rabbit IgG conjugated to Cy-3 (green fluorescence). Colocalization of both markers was indicated by a yellow color. Anti-gelonin antibody had no reactivity with tissue sections from mice injected with saline or VEGF$_{121}$. To determine the percentage of vessels with localized fusion protein, the number of vessels stained with MECA-32 (red), gelonin (green), or both (yellow) were counted at a magnification of ×200 in at least 10 fields per section. Two slides from each mouse were analyzed, and the average percentage of positive vessels was calculated.

Figure 13:
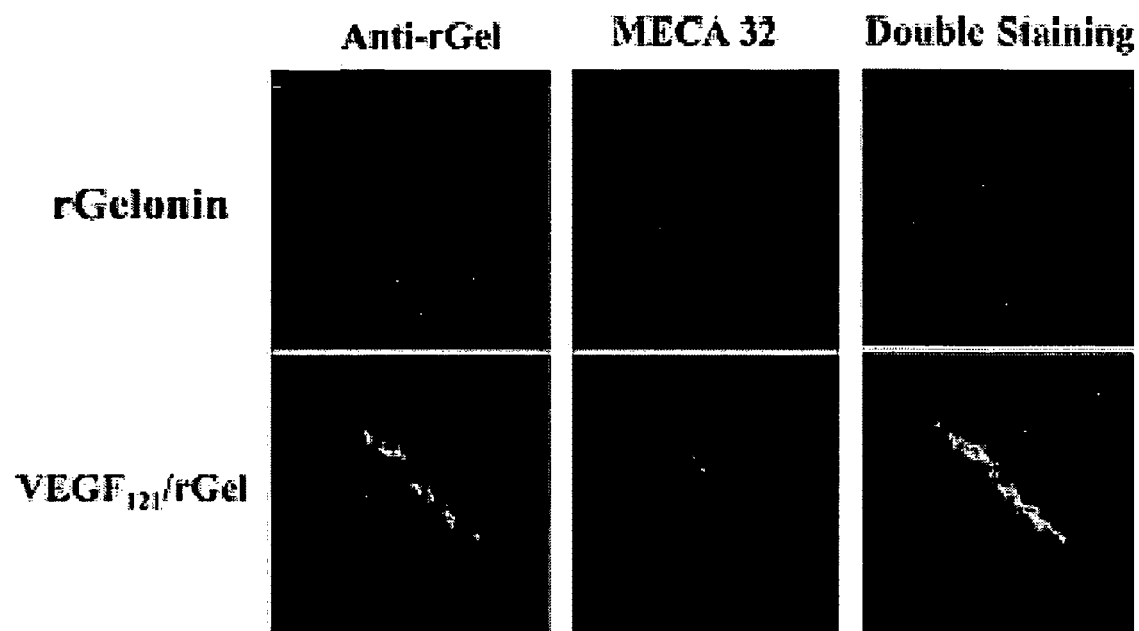
FIG. 13 shows the specific localization of VEGF/rGel to tumor vasculature in PC3 tumors. Nude mice bearing human prostate PC-3 tumors were injected i.v. with $VEGF_{121}$/rGel or rGel (2.5 mg/kg). Thirty minutes after administration, tissues were removed and snap frozen. Sections were stained with immunofluorescent reagents to detect murine blood vessels (MECA-32, red) and with antirGel (green). Vessels stained with both reagents appear yellow. VEGF/rGel localized to tumor vessels, whereas rGel did not. Vessels in all normal organs other than the kidney (glomerulus) were unstained by VEGF/rGel.

As shown in FIG. 13, VEGF$_{121}$/rGel was detected primarily on vascular endothelium of PC-3 tumors (FIG. 13). On average, 62% of vessels positive for MECA 32 were also positive for VEGF$_{121}$/rGel, as detected by using anti-gelonin antibody. In tumor regions of increased vascularity ("hot spots"), approximately 90% of tumor vessels had bound VEGF$_{121}$/rGel. Vessels in normal organs were unstained, with the exception of the kidney, where weak and diffuse staining was detected in the glomeruli. Free gelonin did not localize to tumor or normal vessels in any of the mice. These results indicate that VEGF$_{121}$/rGel localized specifically to tumor vessels after i.v. injection.

EXAMPLE 16

Destruction and Thrombosis of Tumor Vessels by VEGF$_{121}$/rGelonin

Figure 14:
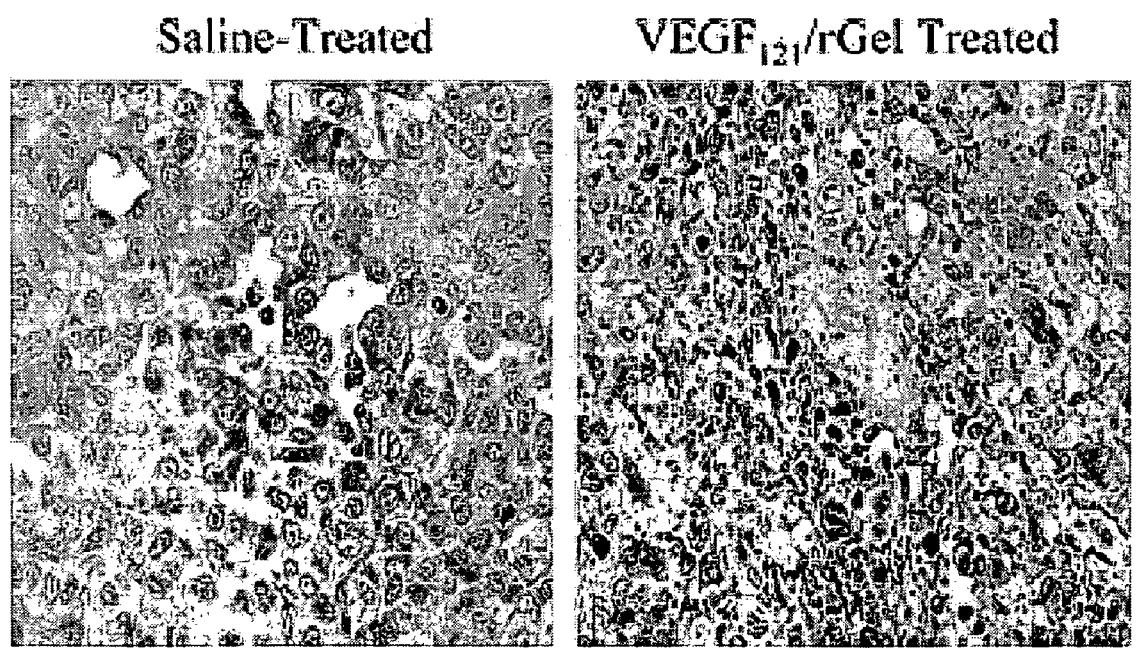
FIG. 14 shows the destruction and thrombosis of tumor blood vessels by VEGF/rGel. Nude mice bearing human prostate PC-3 tumors were treated i.v. with one dose of $VEGF_{121}$/rGel (2.5 mg/kg). Forty-eight hours after administration, tissues were snap-frozen, sectioned, and stained with hematoxylin and eosin. As shown in this representative image, tumors from mice treated with the fusion construct had damaged vascular endothelium. Clots were visible in the larger vessels of the tumors, and erythrocytes were visible in the tumor interstitium, indicating a loss of vascular integrity. In contrast, histological damage was not visible in any normal organs, including the kidneys, of treated mice.

Mice bearing s.c. PC-3 tumors were given one i.v. dose of VEGF$_{121}$/rGel (2.5 mg/kg) or saline. The mice were killed 48 h later, and the tumors and various organs were removed. Paraffin sections were prepared and stained with hematoxylin and eosin. The tumors from VEGF$_{121}$/rGel recipients (FIG. 14) displayed damaged vascular endothelium, thrombosis of vessels, and extravasation of RBC components into the tumor interstitium. Normal tissues had un-damaged vasculature. Treatment of mice with saline had no effect on tumor or normal tissues. As assessed by image analysis, necrotic areas of the tumor increased from ~4% in saline-treated mice to ~12% after treatment with the fusion construct.

EXAMPLE 17

Cytotoxicity of $VEGF_{121}$/rGelonin to MDA-MB-231 Breast Tumor Cells

As assessed by Western blot, MDA-MB-231 breast cancer cells do not appear to express VEGFR-1 or VEGFR-2, the receptors which bind $VEGF_{121}$ (FIG. 15A). Cytotoxicity of $VEGF_{121}$/rGel and rGel against log phase MDA-MB-231 cells was determined as follows. Cells were grown in 96-well flat-bottom tissue culture plates. Purified $VEGF_{121}$/rGel and rGel were diluted in culture media and added to the wells in 5-fold serial dilutions. Cells were incubated for 72 hours. The remaining adherent cells were stained with crystal violet (0.5% in 20% methanol) and solubilized with Sorenson's buffer (0.1 M sodium citrate, pH 4.2 in 50% ethanol). Absorbance was measured at 630 nm. As shown in FIG. 15B, the cytotoxicity of $VEGF_{121}$/rGel on MDA-MB-231cells showed an $IC_{50}$ slightly higher than that observed for recombinant gelonin, indicating that $VEGF_{121}$/rGel does not have a specific target on MBA-MB-231 cells.

EXAMPLE 18

Localization of $VEGF_{121}$/rGelonin to Vascular Endothelium in Breast Tumor Xenografts SCID mice (3 mice per group) bearing orthotopic MDA-MB-231 tumors were intravenously injected with 50 ug of the fusion protein or equivalent amount of free gelonin. The mean tumor volume per group was 260 mm³. Four hours later the mice were sacrificed and exsanguinated. All major organs and tumor were harvested and snap-frozen for preparation of cryosections.

Frozen sections were double stained with a pan-endothelial marker MECA 32 (5 ug/ml) followed by detection of the localized fusion protein using rabbit anti-gelonin antibody (10 ug/ml). MECA 32 rat IgG (provided by Dr. E. Butcher of Stanford University, Calif.) was visualized by goat anti-rat IgG conjugated to FITC (green fluorescence). Rabbit anti-gelonin antibody was detected by goat anti-rabbit IgG conjugated to Cy-3 (red fluorescence).

Co-localization of both markers was indicated by yellow color. Anti-gelonin antibody had no reactivity with tissues sections derived from mice injected with saline or with $VEGF_{121}$. To determine % of vessels with localized fusion protein, MECA 32 positive, gelonin-positive and vessels with combined color were counted at magnification of ×200 in at least 10 fields per section. Two slides from each mouse were analyzed and percent of positive vessels was averaged.

Figure 16:
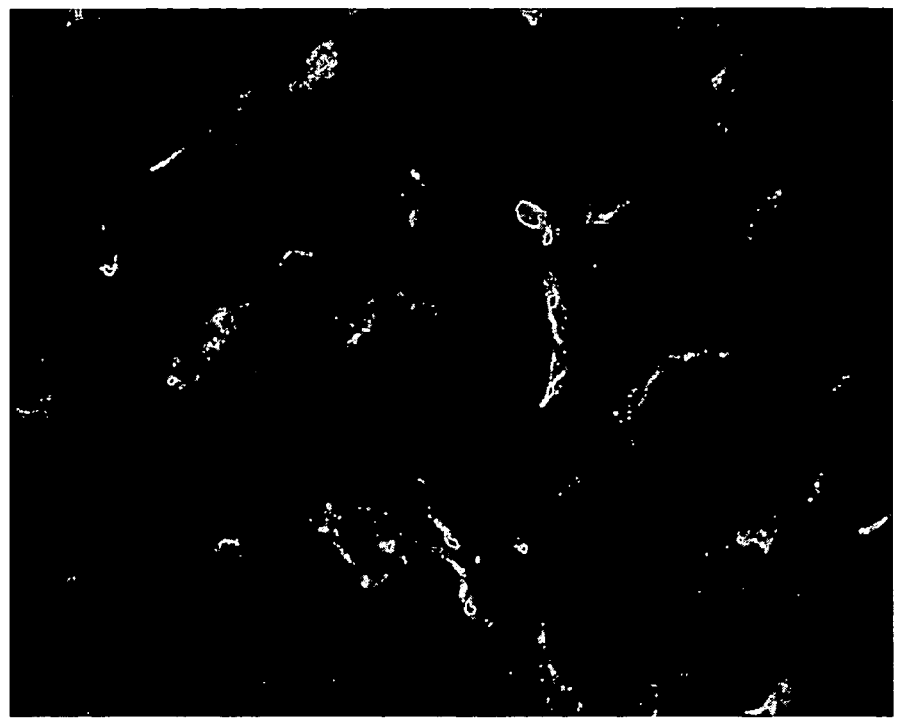
FIG. 16 shows VEGF$_{121}$/rGel localizes to blood vessels of MDA-MB-231 tumor. Mice bearing orthotopically-placed MDA-MB-31 tumors were administered one dose (i.v., tail vein) of VEGF$_{121}$/rGel. Four hours later, the mice were sacrificed and tumors excised and fixed. Tissue sections were stained for blood vessels using the Meca 32 antibody (red) and the section was counter-stained using an anti-gelonin antibody (green). Co-localization of the stains (yellow) demonstrate the presence of the VEGF$_{121}$/rGel fusion construct specifically in blood vessels and not on tumor cells.

As shown in FIG. 16, $VEGF_{121}$/rGel was primarily detected on endothelium of tumor. In average, sixty percent of vessels positive for MECA 32 were also positive for gelonin in the group of $VEGF_{121}$/rGel -injected mice. In the tumor regions of increased vascularity (hot spots), up to 90% of tumor vessels were labeled by anti-gelonin IgG. Vessels with bound $VEGF_{121}$/rGel were homogeneously distributed within the tumor vasculature. Vessels in normal organs were unstained with the exception of the kidney where weak and diffuse staining was detected in the glomeruli. Free gelonin did not localize to tumor or normal vessels in any of the mice, indicating that only targeted gelonin was able to bind to the tumor endothelium. These results indicate that $VEGF_{121}$/rGel specifically localizes to tumor vessels that demonstrate high density and favorable distribution of $VEGF_{121}$/rGel-binding sites.

EXAMPLE 19

Metastatic Model of MDA-MB-231 Tumors

The following examples utilize a breast cancer pulmonary metastatic model to establish $VEGF_{121}$/rGel fusion toxin can inhibit metastatic spread and vascularization of metastases.

Human breast carcinoma MDA-MB-231 cells consistently lodge in lungs following intravenous injection into the tail vein of athymic or SCID mice. Micrometastases are first detected 3 to 7 days after injection of $5\times10^5$ cells and macroscopic colonies develop in 100% of the injected mice within 4 to 7 weeks. Mortality occurs in all mice within 10-15 weeks. This model of experimental breast cancer metastasis examines the ability of tumor cells to survive in the blood circulation, extravasate through the pulmonary vasculature and establish growing colonies in the lung parenchyma.

Female SCID mice, aged 4-5 weeks, were injected in a tail vein with 0.1 ml of MDA-MB-231 cell suspension ($5\times10^5$ cells). The mice were randomly separated into two groups (6 mice per group) and were treated with either $VEGF_{121}$/rGel or gelonin alone (100 μg intraperitoneally, 6 times total with an interval of 3 days) starting the $8^{th}$ day after the injection of cells. Treatment with $VEGF_{121}$/rGel for 2 weeks allow the mice to receive the maximal tolerated accumulative dose of the drug (600 μg per mouse). Prior studies established that $VEGF_{121}$/rGel given at such dose did not cause histopathological changes in normal organs. The accumulative dose of 640-800 μg of total $VEGF_{121}$/rGel fusion protein, given i.p. over period of 4 weeks, did not induce significant toxicity as judged by morphological evaluation of normal organs. Transient loss of weight (~10%) was observed 24 hours after most of the treatments with complete weight recovery thereafter.

Metastatic colonies were allowed to expand for three weeks after treatment with $VEGF_{121}$/rGel in order to evaluate long-term effect of $VEGF_{121}$/rGel on the size of the colonies, proliferation index of tumor cells and their ability to induce new blood vessel formation. Three weeks after termination of the treatment, the animals were sacrificed and their lungs were removed. One lobe was fixed in Bouin's fixative and the other lobe was snap-frozen. After fixation in Bouin's fixative, the tumor colonies on the lung surface appear white, whereas the normal lung tissue appears brown. The number of tumor colonies on the surface of each lung was counted and the weight of each lung was measured. The values obtained from individual mice in the $VEGF_{121}$/rGel and rGel groups were averaged per group.

EXAMPLE 20

Effects of $VEGF_{121}$/rGelonin on the Number, Size and Vascular Density of MDA-MB-231 Pulmonary Metastatic Foci Frozen samples of lung tissue was cut to produce sections of 6 μm. Blood vessels were visualized by MECA 32 antibody and metastatic lesions were identified by morphology and by 6w/32 antibody directed against human HLA antigens. Hybridoma producing the mouse monoclonal 6w/32 antibody was purchased from ATCC. The 6w/32 antibody was purified from hybridoma supernatant using Protein A resin.

Each section was double stained by MECA 32 and 6w/32 antibodies to ensure that the analyzed blood vessels are located within a metastatic lesion. Slides were first viewed at low magnification (×2 objective) to determine total number of foci per a cross-section. Six slides derived from individual mice in each group were analyzed and the number was averaged. Images of each colony were taken using digital camera (CoolSnap) at magnifications of ×40 and ×100 and analyzed using Metaview software that allows measurements of smallest and largest diameter, perimeter (µm) and area (mm$^2$).

The vascular endothelial structures identified within a lesion were counted and number of vessels per each lesion was determined and normalized per mm$^2$. The mean number of vessels per mm$^2$ was calculated per each slide and averaged per VEGF$_{121}$/rGel and rGel groups (6 slides per group). The results are expressed±SEM. The same method applied to determine the mean number of vessels in non-malignant tissues.

Figure 17:
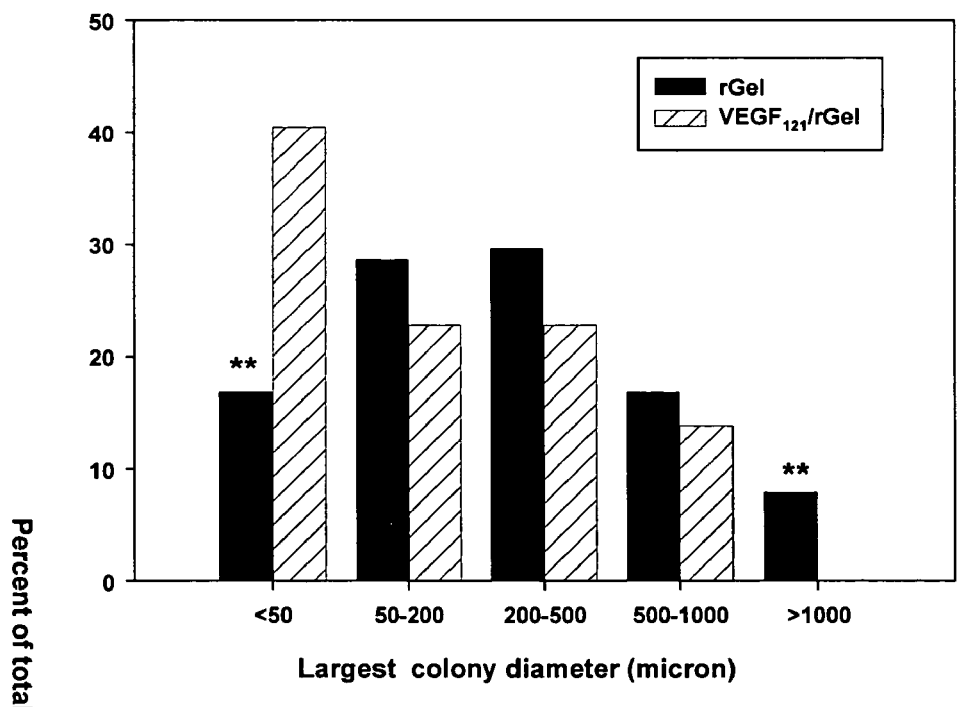
FIG. 17 shows VEGF$_{121}$/rGel reduces number of large metastatic colonies in lungs. The size of tumor colonies was analyzed on slides stained with 6w/32 antibody that specifically recognizes human HLA antigens. The antibody delineates colonies of human tumor cells and defines borders between metastatic lesions and mouse lung parenchyma. The largest size differences between VEGF$_{121}$/rGel and control groups were found in groups of colonies having diameter either less than 50 µm or more than 1000 µm. In the VEGF$_{121}$/rGel-treated mice more than 40% of total foci were extremely small (<50 micron) as compared to 18% in the control group. The control mice had approximately 8% of extremely large colonies (>1000 µm) whereas VEGF$_{121}$/rGel-treated mice did not have colonies of this size.

Treatment with VEGF$_{121}$/rGel but not with free gelonin significantly reduced both the number of colonies per lung and the size of the metastatic foci present in lung by 42-58% as shown in FIG. 17 and Table 2.

Figure 18A:
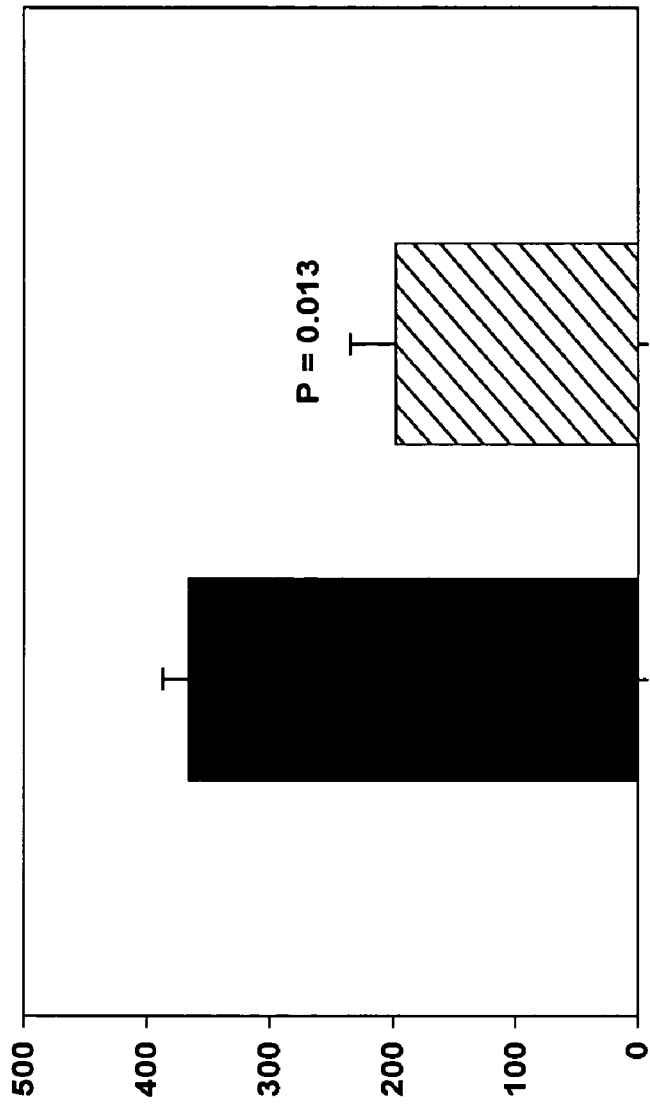
FIGS. 18A-B show VEGF$_{121}$/rGel inhibits vascularization of MDA-MB-231 pulmonary metastases. Lungs derived from VEGF$_{121}$/rGel and rGel-treated mice were stained with MECA 32 antibody and the number of vessels per mm$^2$ within the metastatic foci was determined (FIG. 18A). The mean number of vessels per mm$^2$ in lung metastases of VEGF$_{121}$/rGel-treated mice was reduced by approximately 50% as compared to those in rGel-treated mice.
Figure 18B:
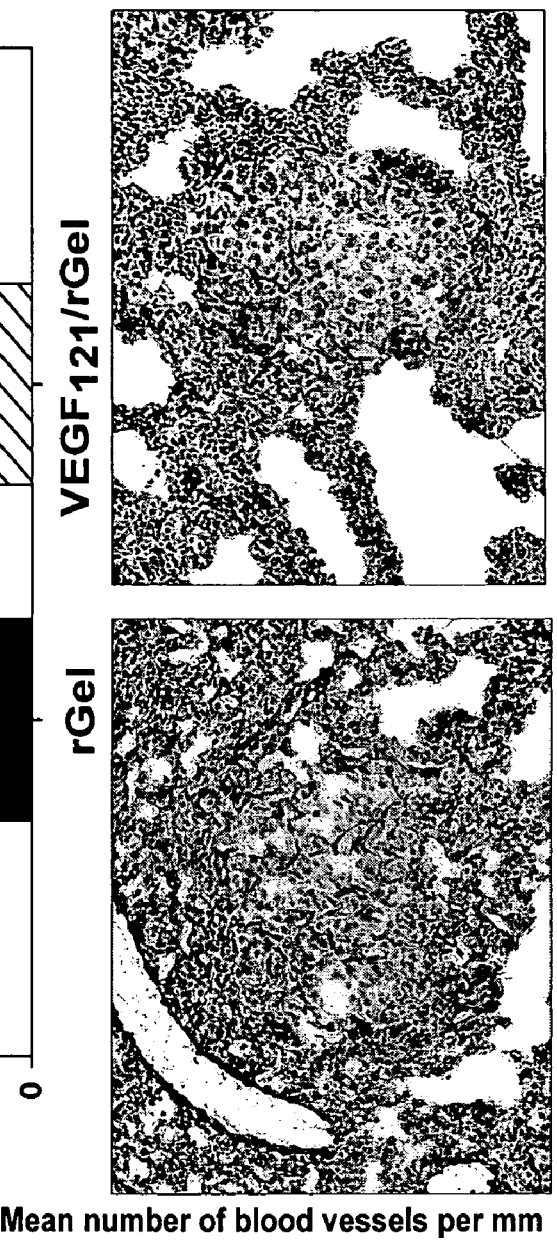

The overall mean vascular density of lung colonies was reduced by 51% compared to the rGel treated controls (Table 3 and FIG. 18). The observed effect, however, was non-uniformly distributed among different tumor colony sizes. The greatest impact on vascularization was observed on mid-size and extremely small tumors (62 and 69% inhibition respectively) while large tumors demonstrated the lease effect (10% inhibition). The majority of lesions in the VEGF$_{121}$/rGel-treated mice (~70%) were avascular whereas only 40% of lesions from the control group did not have vessels within the metastatic lung foci.

TABLE 2

Effect of VEGF$_{121}$/rGelonin on Number And Size of Pulmonary Metastases of MDA-MB-231 Human Breast Carcinoma Cells

| Parameter | Treatment[a] | | % inhibition vs. rGelonin treatment | P value[b] |
|---|---|---|---|---|
| | rGelonin | VEGF$_{121}$/rGel | | |
| No. surface colonies per lung (range)[c] | 53.3 ± 22 (33-80) | 22.4 ± 9.2 (11-41) | 58.0% | 0.03 |
| No. intraparenchymal colonies per cross-section (range)[d] | 22 ± 7.5 (18-28) | 12.8 ± 5.5 (5-18) | 42.0% | 0.02 |
| Mean area of colonies (µm)[e] | 415 ± 10 | 201 ± 37 | 51.9% | 0.01 |
| Mean % of colonies-occupied area per lung section[f] | 57.3 ± 19 | 25.6 ± 10.5 | 55.4% | 0.01 |

[a]Mice with MDA-MB-231 pulmonary micrometastases were treated i.p. with VEGF$_{121}$/rGel or free gelonin as described.
[b]P value was calculated using t-Student test.
[c]Lungs were fixed with Bouin's fixative for 24 hours. Number of surface white colonies was determined for each sample and averaged among 6 mice from VEGF$_{121}$/rGel or rGel control group. Mean number per group ± SEM is shown. Numbers in parentheses represent range of colonies in each group.
[d]Frozen sections were prepared from metastatic lungs. Sections were stained with 6w/32 antibody recognizing human tumor cells. Number of intraparenchymal colonies identified by brown color was determined for each cross-section and averaged among 6 samples of individual mice from VEGF$_{121}$/rGel or rGel control group. Mean number per group ± SEM is shown. Numbers in parentheses represent range of colonies in each group.
[e]Area of foci identified by 6w/32 antibody was measured by using Metaview software. Total number of evaluated colonies was 101 and 79 for rGel and VEGF$_{121}$/rGel group, respectively. Six individual slides per each group were analyzed. The mean area of colony in each group ± SEM is shown.
[f]The sum of all regions occupied by tumor cells and the total area of each lung cross-section was determined and % of metastatic regions from total was calculated. The values obtained from each slide were averaged among 6 samples from VEGF$_{121}$/rGel or rGel control group. The mean % area occupied by metastases from total area per group ± SEM is shown.

TABLE 3

Effect of VEGF$_{121}$/rGelonin On Vascularity of Pulmonary Metastases of MDA-MB-231 Human Breast Carcinoma Cells

| Size of colonies[a] | Largest diameter range (µm) | No. vascularized colonies from total analyzed (%)[b] | | % Inhibition vs. radiation treatment |
|---|---|---|---|---|
| | | rGel | VEGF$_{121}$/rGel | |
| Extremely small | <50 | 7/24 (29%) | 3/32 (9.3%) | 69 |
| Small | 50-200 | 19/48 (39.5%) | 6/24 (25%) | 37 |
| Mid-size | 200-500 | 25/30 (83.3%) | 8/25 (32%) | 62 |
| Large | 500-1000 | 17/17 (100%) | 10/11 (90.0%) | 10 |
| Extremely large | >1000 | 8/8 (100%) | N/A | N/A |
| No. vascular foci/total analyzed (%)[c] | | 76/127 (59.8%) | 27/92 (29.3%) | 51 |

[a]Colonies identified on each slide of a metastatic lung were subdivided into 5 groups according to their largest diameter.
[b]Frozen lung sections from VEGF$_{121}$/rGel or rGel treated mice were stained with MECA 32 antibody. A colony was defined as vascularized if at least one blood vessel branched out from the periphery and reached a center of the lesion. Six slides per each group derived from individual mice were analyzed and data were combined.
[c]Total number of the analyzed colonies was 127 and 92 for rGel and VEGF$_{121}$/rGel treated groups, respectively. Seventy percent of foci in the VEGF$_{121}$/rGel-treated group were avascular whereas only 40% of lesions from the control group did not have vessels within the metastatic foci.

EXAMPLE 21

Effect of VEGF$_{121}$/rGelonin on the Number of Cycling Cells in the MDA-MB-231 Pulmonary Metastatic Foci Frozen sections of normal mouse organs and metastatic lungs were fixed with acetone for 5 min and rehydrated with PBST for 10 min. All dilutions of antibodies were prepared in PBST containing 0.2% BSA. Primary antibodies were detected by appropriate anti-mouse, anti-rat or anti-rabbit HRP conjugates (Daco, Carpinteria, Calif.). HRP activity was detected by developing with DAB substrate (Research Genetics).

To determine the number of cycling cells, tissue sections were stained with the ki-67 antibody (Abcam, Inc., Cambridge, UK) followed by anti-mouse IgG HRP conjugate. Sections were analyzed at magnification of ×100. Number of cells positive for ki-67 was normalized per mm$^2$. The mean number±SD per VEGF$_{121}$/rGel or control group is presented. The average numbers derived from analysis of each slide were combined per either VEGF$_{121}$/rGel or rGel group and analyzed for statistical differences.

Figure 19:
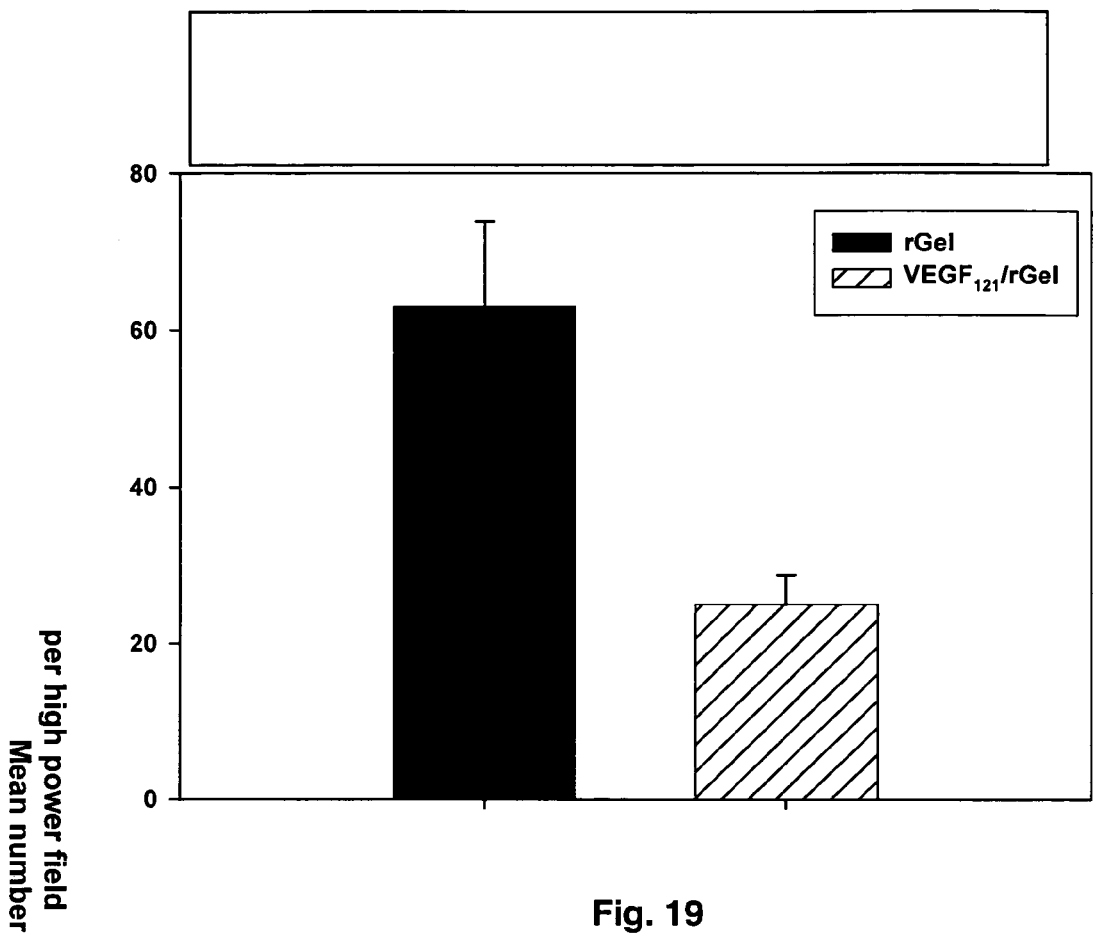
FIG. 19 shows VEGF$_{121}$/rGel inhibits proliferation of metastatic MDA-MB-231 cells in the lungs. Frozen sections of lungs derived from VEGF$_{121}$/rGel or rGel-treated mice were stained with Ki-67 antibody. Stained sections were examined under ×40 objective to determine the number of tumor cells with positive nuclei (cycling cells). Positive cells were enumerated in 10 colonies per slide on six sections derived from individual mice per each treatment group. The mean number per group±SEM is presented. VEGF$_{121}$/rGel treatment reduced the average number of cycling cells within the metastatic foci by approximately 60%.

The number of cycling tumor cells in lesions from the VEGF$_{121}$/rGel group was reduced by ~60% as compared to controls (FIG. 19). The overall mean vascular density of lung colonies was reduced by 51% (Table 3 and FIG. 18). These findings suggest that vascularity of metastases directly affects tumor cell proliferation.

EXAMPLE 22

Figure 20:
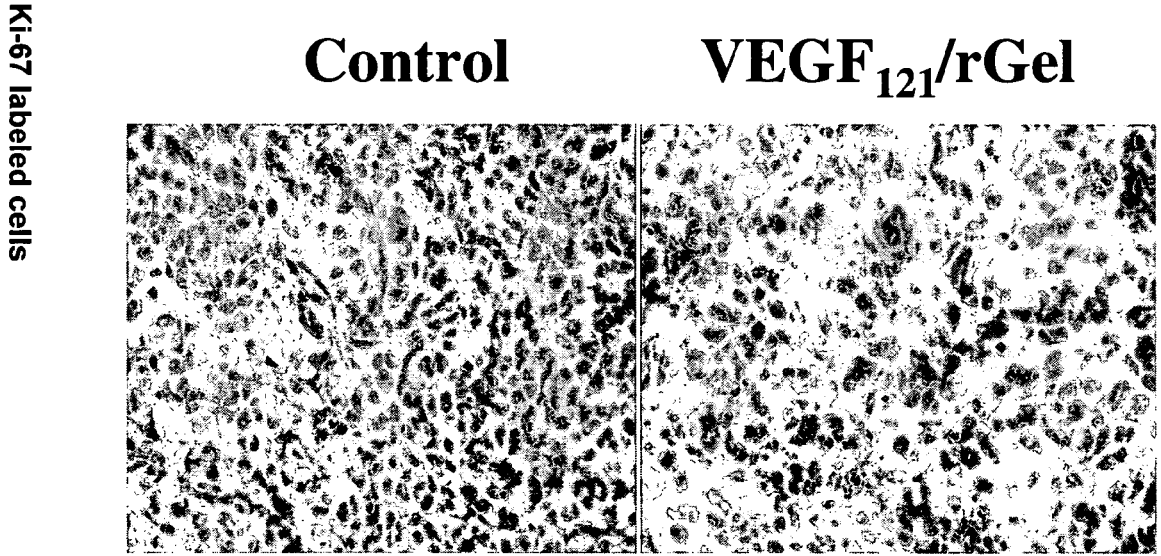
FIG. 20 shows detection of VEGFR-2 on vasculature of metastatic lesions by anti-VEGFR-2 antibody RAFL-1. Frozen sections of lungs from mice treated with VEGF$_{121}$/rGel or free gelonin were stained with monoclonal rat anti-mouse VEGFR-2 antibody RAFL-1 (10 µg/ml). RAFL-1 antibody was detected by goat anti-rat IgG-HRP. Sections were developed with DAB and counterstained with hematoxylin. Representative images of lung metastases of comparable size (700-800 µm in the largest diameter) from each treatment group are shown. Images were taken with an objective of ×20. Note that the pulmonary metastases from the VEGF$_{121}$/rGel treated group show both reduced vessel density and decreased intensity of anti-VEGFR-2 staining compared to control lesions.

Effect of $VEGF_{121}$/rGelonin on flk-1 Expression in Tumor Vessel Endotheluim of MDA-MB-231 Pulmonary Metastatic Foci The expression of VEGF receptor-2 on the vasculature of breast tumors metastatic to lung was assessed using the RAF-1 antibody. Frozen sections of lungs from mice treated with $VEGF_{121}$/rGel or free gelonin were stained with monoclonal rat anti-mouse VEGFR-2 antibody RAFL-1 (10 μg/ml). RAFL-1 antibody was detected by goat anti-rat IgG-HRP. The expression of KDR on the remaining few vessels present in lung metastatic foci demonstrated a significant decline compared to that of lung foci present in control tumors (FIG. 20). This suggests that the $VEGF_{121}$/rGel agent is able to significantly down-regulate the receptor or prevent the outgrowth of highly receptor-positive endothelial cells.

EXAMPLE 23

Summary of the Biological Properties of $VEGF_{121}$/rGelonin $VEGF_{121}$/rGel was found to be selectively toxic to dividing endothelial cells overexpressing the KDR/Flk-1 receptor. Nondividing (confluent) endothelial cells were almost 60-fold more resistant than were dividing cells to the fusion construct and also were more resistant to free gelonin (Table 1). These findings accord with those of previous studies that showed conjugates of vascular endothelial growth factor and diphtheria toxin were highly toxic to log-phase cells but were not toxic to confluent endothelial cells. The greater sensitivity of dividing endothelial cells to VEGF-toxin constructs may be because of differences in intracellular routing or catabolism of the construct as observed with other targeted therapeutic agents.

Cytotoxicity studies demonstrated that expression of the KDR/Flk-1 receptor is needed for $VEGF_{121}$/rGel to be cytotoxic. Cells overexpressing KDR/Flk-1 ($>1\times10^5$ sites per cell) were highly sensitive to the $VEGF_{121}$/rGel fusion construct, whereas cells expressing fewer than $0.4\times10^5$ sites per cell were no more sensitive to the fusion toxin than they were to free gelonin. Again, the requirement to surpass a threshold level of KDR/Flk-1 for cytotoxicity may contribute to the safety of $VEGF_{121}$/rGel. In normal organs, including the kidney glomerulus and pulmonary vascular endothelium, the level of KDR/Flk-1 may be below that needed to cause toxicity. The number of receptors for vascular endothelial growth factor on endothelial cells in the vasculature of normal organs has been reported to be significantly lower than on tumor vasculature. Indeed, one could not detect binding of $VEGF_{121}$/rGel to normal vascular endothelium in organs other than the kidney, where weak binding was observed. Furthermore, no damage to vascular endothelium was observed in normal organs, including the kidney.

Other gelonin-based-targeted therapeutics also have been observed to become toxic to cells only when a certain threshold level of binding is surpassed. In a recent study of immunotoxins directed against the c-erb-2/HER2/neu oncogene product, immunotoxins were not cytotoxic to tumor cells expressing less than about $1\times10^6$ HER2/neu sites per cell. The lack of sensitivity of cells having low levels of receptors is presumably because the cells internalize too little of the toxin or traffic it to compartments that do not permit translocation of the toxin to the ribosomal compartment.

Although VEGF/rGel fusion can bind to both the KDR and FLT-1 receptors, only cells expressing KDR were able to internalize the construct thereby delivering the toxin component to the cytoplasmic compartment. It has been suggested that it is the interaction of vascular endothelial growth factor with the KDR receptor but not the FLT-1 receptor that is responsible for the growth proliferative signal on endothelial cells. Other studies suggest that the KDR receptor is primarily responsible for mediating the vascular permeability effects of VEGF-A. Although FLT-1 receptor may modulate signaling of the KDR receptor and impact monocyte response to vascular endothelial growth factor, its role in neovascularization has not been well-defined.

The presence of FLT-1, even at high levels, does not seem to mediate cellular toxicity of the $VEGF_{121}$/rGel fusion toxin. Although VEGF binds to the FLT-1 receptor, the current study has been unable to demonstrate receptor phosphorylation as a result of ligand binding. It has been suggested that receptor phosphorylation may be required for KDR signaling and internalization. If so, the receptor-fusion-toxin complex may not internalize efficiently after binding to FLT-1 for the fusion protein to be routed to an intracellular compartment from which the toxin can escape to the cytosol. The relative contributions of the FLT-1 and KDR receptors to the biological effects of vascular endothelial growth factor examined by using a monoclonal antibody that blocks the interaction of vascular endothelial growth factor with KDR/Flk-1 but not FLT-1 demonstrate that KDR/Flk-1 is the major receptor determining the vascular permeability-inducing and angiogenic effects of vascular endothelial growth factor in tumors.

Another important observation was that the cytotoxic effects of the $VEGF_{121}$/rGel construct on vascular endothelial cells did not involve an apoptotic mechanism. This is in sharp contrast to studies of other toxins such as ricin A chain (RTA) and *Pseudomonas* exotoxin (PE) which demonstrate generation of apoptotic effects that are mediated, at least in part, by caspase activation. It has been suggested that PE toxins may generate cytotoxic effects through both caspase-dependant and protein synthesis inhibitory mechanisms. Despite the sequence homology of ricin A chain and rGel and the known similarities in their mechanism of action, it appears that these two toxins differ in their proapoptotic effects. One possible explanation for the observed differences in apoptotic effects between ricin A chain and the rGel toxin could be in the cell types examined. The cells targeted in the current study of rGel are non-transformed endothelial cells while those in the ricin A chain study were tumor cells.

The exposure duration studies for the $VEGF_{121}$/rGel fusion toxin demonstrate that as little as 1 hr exposure to target cells is required to develop a cytotoxic effect 72 hrs later. However, continual exposure for up to 48 hrs was shown to improve the cytotoxic effect by almost 10 fold. Should pharmacokinetic studies demonstrate a relatively short plasma half-life for this agent, this may suggest that optimal therapeutic effect could be achieved by maintaining blood concentrations of drug at therapeutic concentrations for at least 48 hrs. This could be achieved by frequent interval dosing or continuous infusion but may be important in the development of pre-clinical and clinical dosing strategies.

The antitumor effects of the $VEGF_{121}$/rGel fusion construct against both melanoma and human prostate carcinoma xenografts was impressive in magnitude and prolonged. A-375M and PC-3 cells in culture were resistant to the fusion construct in vitro, despite the reported presence of KDR on the melanoma (but not on PC-3) cells. Therefore, the antitumor effects observed in vivo appear not to be caused by direct cytotoxic effects of VEGF$_{121}$/rGel on the tumor cells themselves. The antitumor effect seems to be exerted indirectly on the tumor cells through specific damage to tumor vasculature. The VEGF$_{121}$ fusion toxin localized to tumor blood vessels after i.v. administration. Vascular damage and thrombosis of tumor blood vessels were observed within 48 h of administration of VEGF$_{121}$/rGel to PC-3 mice, consistent with the primary action of the construct being exerted on tumor vascular endothelium.

VEGF$_{121}$/rGel also has an impressive inhibitory effect on tumor metastases. Administration of the VEGF$_{121}$/rGel construct to mice previously injected (i.v.) with the MDA-MB-231 human breast tumor cells dramatically reduced the number of tumor colonies found in lung, their size and their vascularity. In addition, the number of cycling breast tumor cells within lung metastatic foci was found to be reduced by an average of 60%. In addition to the reduced number of blood vessels present in lung metastases of treated mice, the few vessels present had a greatly reduced expression of VEGFR-2. Therefore, VEGF$_{121}$/rGel demonstrated an impressive, long-term impact on the growth and development of breast tumor metastatic foci found in lung.

The salient finding of the effects of VEGF$_{121}$/rGel construct is that this fusion toxin is specifically cytotoxic to cells over-expressing the KDR receptor for VEGF. However, the human breast MDA-MB-231 cancer cells employed for the metastatic studies described above do not express this receptor and, therefore, were not directly affected by this agent. The antitumor effects of VEGF$_{121}$/rGel observed on the MDA-MB-231 metastases thus appear to be solely the result of targeting tumor vasculature.

Neovascularization is a particularly important hallmark of breast tumor growth and metastatic spread. The growth factor VEGF-A and the receptor KDR have both been implicated in highly metastatic breast cancer. It is of interest to note that administration of VEGF$_{121}$/rGel resulted in a 3-fold decrease in the number of Ki-67 labeled (cycling) cells in the metastatic foci present in lung (FIG. 19). Clinical studies have suggested that tumor cell cycling may be an important prognostic marker for disease-free survival in metastatic breast cancer, but that Ki-67 labeling index, tumor microvessel density (MVD) and neovascularization appear to be independently regulated processes (Honkoop et al., 1998; Vartanian and Weidner, 1994). This is the first report of a significant reduction in tumor labeling index produced by a vascular targeting agent.

The vascular-ablative effects of the VEGF$_{121}$/rGel fusion construct alone were able to partially eradicate lung metastases. Although development of small, avascular, metastatic foci within lung tissue was observed, the growth of larger pulmonary metastases was completely inhibited by treatment with the VEGF$_{121}$/rGel fusion toxin. It is conceivable that combination of VEGF$_{121}$/rGel fusion construct with chemotherapeutic agents or with radiotherapeutic agents that directly damage tumor cells themselves may provide for greater therapeutic effect. Studies of several vascular targeting agents in combination with chemotherapeutic agents have already demonstrated a distinct in vivo anti-tumor advantage of this combination modality against experimental tumors in mice (Siemann et al., 2002). Studies by Pedley et al. (2002) have also suggested that combination of vascular targeting and radioimmunotherapy may also present a potent antitumor combination. Finally, studies combining hyperthermia and radiotherapy with vascular targeting agents have demonstrated enhanced activity against mammary carcinoma tumors in mice (Murata et al., 2001).

EXAMPLE 24

Treatment of Orthotopic Bladder Tumors with VEGF$_{121}$/rGelonin

Figure 21:
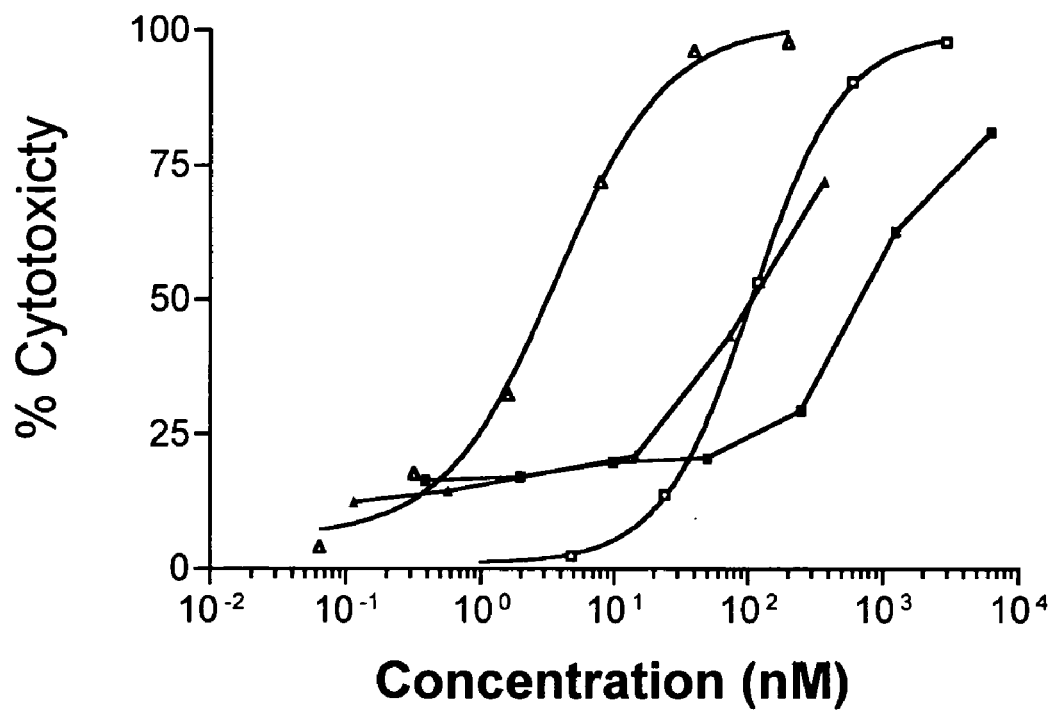
FIG. 21 shows in vitro cytotoxicity of VEGF$_{121}$/rGel on 253J B-V bladder tumor cells. Log-phase cells were plated in 96-well plates and incubated with serial dilutions of VEGF$_{121}$/rGel or rGel for 72 h. Cytotoxicity experiment was performed in triplicate, and data points are represented as the mean. VEGF$_{121}$/rGel is far more toxic than rGel on PAE/KDR cells (IC$_{50}$ of 1 nM versus 100 nM). In contrast, the cytotoxic effects of both agents are substantially reduced towards 253J B-V cells (IC$_{50}$ of 100 nM with VEGF$_{121}$/rGel versus 700 nM with rGel), demonstrating less specific cytotoxicity of the fusion construct compared to free toxin on these cells.

Direct cytotoxic effect of VEGF$_{121}$/rGel and rGel on the highly tumorigenic and metastatic human bladder tumor cell line 253J B-V was initially evaluated in vitro and compared to the cytotoxic effect on PAE/KDR cells. Treatment of log-phase cells with VEGF$_{121}$/rGel for 72 h showed the greatest cytotoxic effect against PAE/KDR cells, with an IC$_{50}$ of 1 nM (FIG. 21). In contrast, the IC$_{50}$ of rGel on these cells was approximately 100 nM, similar to the IC$_{50}$ of VEGF$_{121}$/rGel on 253J B-V cells. However, 253J B-V cells were approximately 7-fold more sensitive to the cytotoxic effects of VEGF$_{121}$/rGel compared to that of untargeted rGel toxin (100 nM vs. 700 nM respectively). These values are similar to those for other tumor cells. Thus, VEGF$_{121}$/rGel is far more potent towards endothelial cells that over-express the KDR receptor than to 253J B-V cells in vitro.

The therapeutic and anti-angiogenic effect of the fusion protein VEGF$_{121}$/rGel was evaluated against human bladder cancer xenografts growing in athymic nude mice. Each mouse was anesthetized with sodium pentobarbital (25 mg/kg) i.p. and placed in the supine position. A lower midline incision was performed, and the bladder was exposed. The highly tumorigenic and metastatic 253J B-V human transitional cell carcinoma cells ($3.5 \times 10^5$ cells in 50 µl of HBSS) were implanted into the wall of the bladder in the area of the bladder dome using 30-gauge needles on disposable 1 ml syringes. A successful implantation was indicated by a bleb in the bladder wall serosa. The abdominal wound was closed in one layer with metal wound clips.

Thirty mice were randomized into three treatment groups, and treatment began on the third day after tumor injection into the bladder. The animals were treated with the following protocol: Group 1, 200 µl saline every other day for ten days (5 treatments); Group 2, 29 µg recombinant gelonin in 200 µl saline every other day for ten days (5 treatments); Group 3, 80 µg VEGF$_{121}$/rGel in 200 µl saline every other day for ten days (5 treatments). Twenty-one days after tumor injection, the animals were sacrificed and the bladders were harvested, weighed and processed.

As shown in FIG. 21, no difference was observed in tumor weight from mice treated with saline or rGel (p<0.05). In contrast, tumors from mice treated with VEGF$_{121}$/rGel weighed about 40% that of the control (p<0.05).

Figure 22:
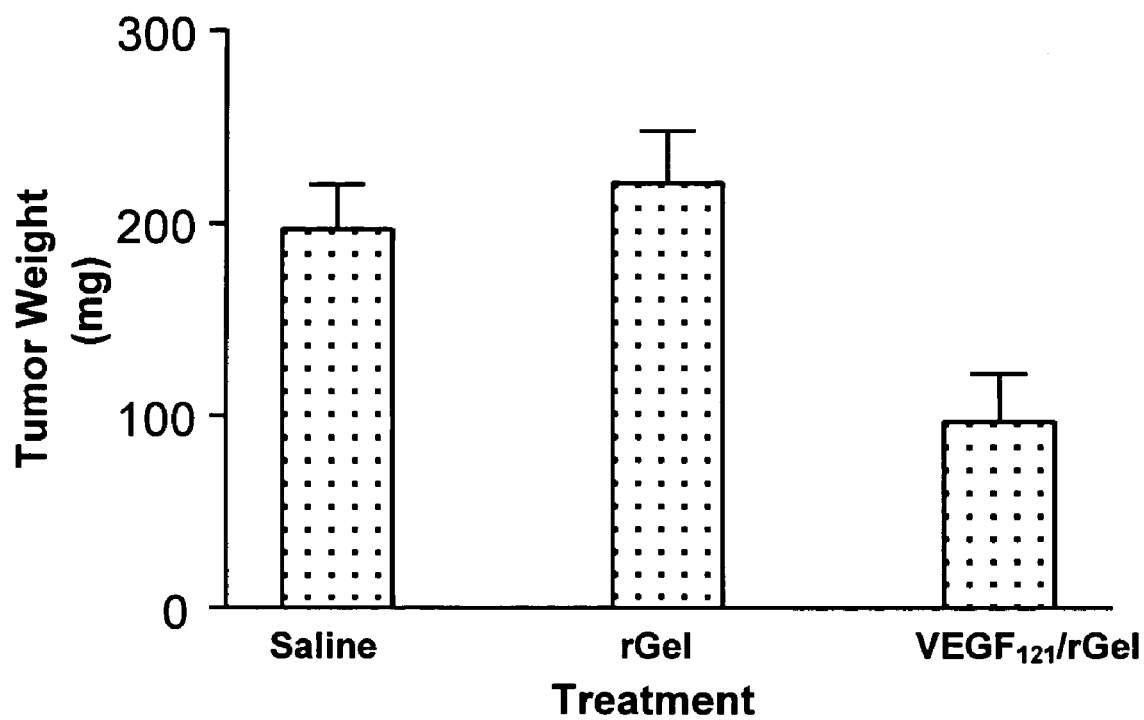
FIG. 22 shows the effects of VEGF$_{121}$/rGel treatment on in vivo growth of orthotopic 253J B-V bladder tumor cells. Tumor bearing mice were treated intravenously with saline, rGel or VEGF$_{121}$/rGel. Mice were necropsied 21 days after tumor implantation and bladder tumors were harvested. Treatment with VEGF$_{121}$/rGel results in significant suppression of bladder tumor growth, roughly 60%, compared to controls (p<0.05).

Bladder tumors from treated mice were processed for histology and immunohistochemical analysis. Immunofluorescence of tumor tissue sections with anti-CD-31 and anti-gelonin antibodies showed dramatic co-localization of VEGF$_{121}$/rGel with CD-31 on tumor neovasculature (FIG. 22), indicating that VEGF$_{121}$/rGel targets the tumor endothelium. In some instances, VEGF$_{121}$/rGel did not co-localize with CD-31. VEGF$_{121}$/rGel was not detected in other tissues. Immunostaining with anti-gelonin antibody of tumors from animals treated with rGel were negative, indicating the specificity of VEGF$_{121}$ as a targeting moiety for the tumor vasculature.

Figure 23:
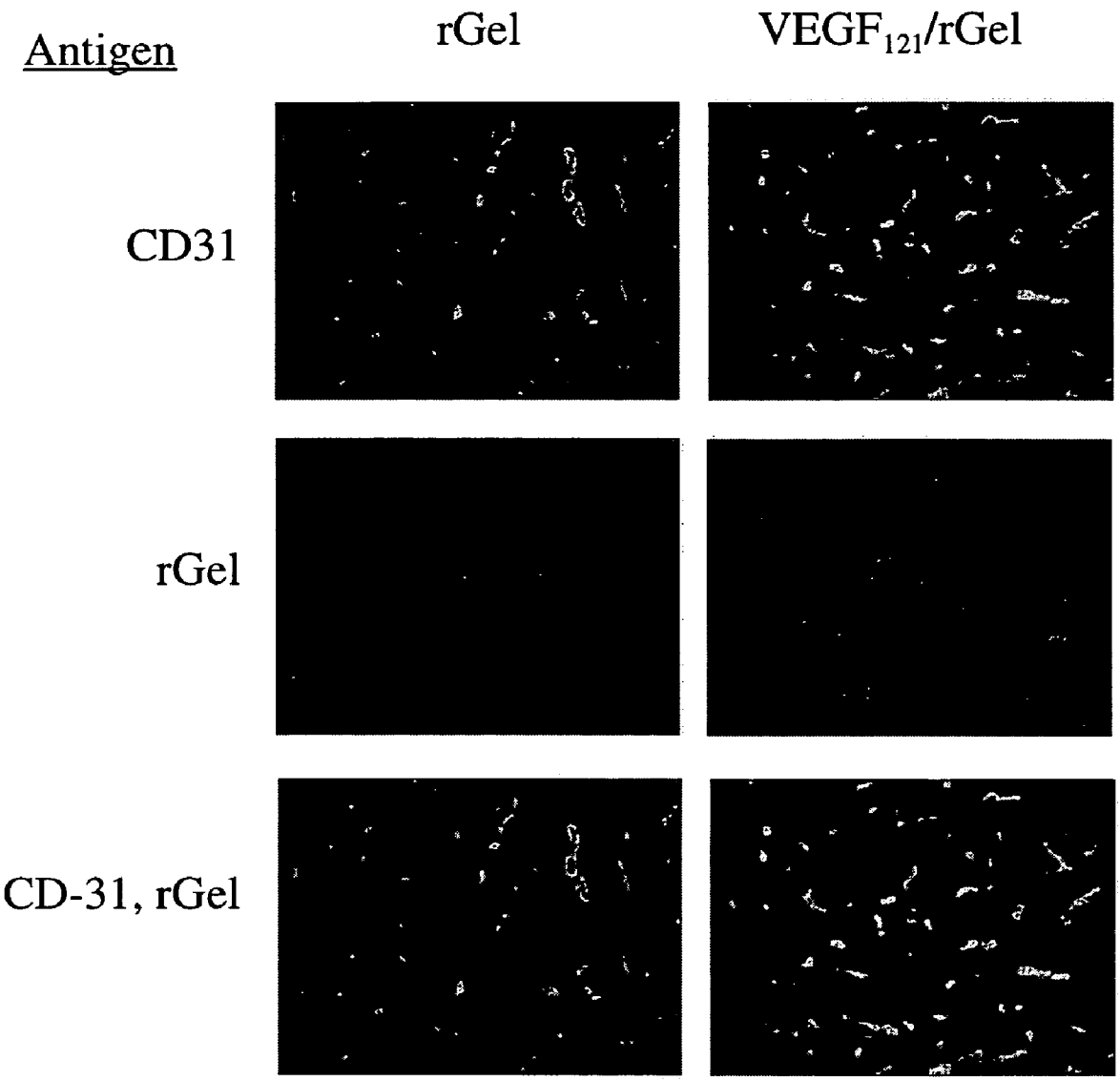
FIG. 23 shows immunofluorescence of bladder tumor tissue sections from mice treated with rGel or VEGF$_{121}$/rGel. CD-31 (green) was seen in tissue sections from mice treated with both VEGF$_{121}$/rGel and rGel (panel A). However, the presence of gelonin (red) was only seen in tumor tissues of mice treated with VEGF$_{121}$/rGel (panel B). Overlay of anti-CD-31 and anti-rGel antibody fluorescence shows co-localization of rGel and CD-31, indicating that VEGF$_{121}$/rGel targets the tumor neovasculature (panel C). No such co-localization of rGel and CD-31 was seen in tumors from animals treated only with rGel.
Figure 24:
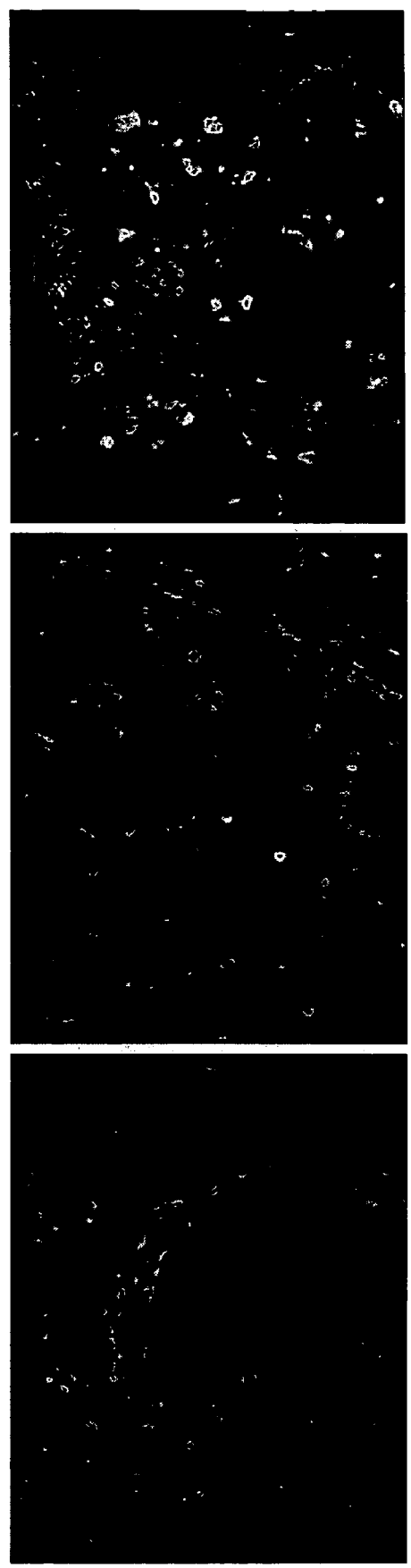
FIG. 24 shows TUNEL analysis of orthotopic bladder tumors. Tumors treated with VEGF$_{121}$/rGel showed a much higher TUNEL staining compared to controls. Negative control denotes cells analyzed for TUNEL without addition of terminal deoxynucleotidyl transferase, Control is a bladder tumor that was treated with rGel.

To study the in vivo effect on tumor cells as a result of VEGF$_{121}$/rGel cytotoxicity on endothelial cells, bladder tumors from mice treated with VEGF$_{121}$/rGel, rGel or saline were stained for apoptotic effects. Both necrotic as well as non-necrotic regions were examined by immunofluorescent terminal deoxynucleotidyl-dUTP nick-end labeling (TUNEL) assay. As shown in FIG. 23, tumors treated with either saline or rGel showed virtually no apoptotic regions. In contrast, treatment with VEGF$_{121}$/rGel resulted in an increase in necrotic areas. VEGF$_{121}$/rGel-treated tumors showed significantly higher TUNEL staining than rGel- or saline-treated tumor-bearing mice.

Laser Scanning Cytometry (LSC)-mediated quantitative analysis was used to determine the number of TUNEL positive cells in each tissue section. Negative control slides were used to set the gates on the scattergram, and each bladder tumor section was scanned by LSC to determine the percentage of apoptotic cells in 1×10$^4$ total cells per tumor. Tumor sections from rGel-treated mice had 2.73±0.72% (n=3) TUNEL positive cells, whereas tumor sections from VEGF$_{121}$/rGel-treated mice had 6.3±1.67% (n=3) TUNEL positive cells (p=0.027). Thus, VEGF$_{121}$/rGel is a cytotoxic agent that targets the neovasculature of bladder carcinoma and a useful combination therapy for the treatment of bladder cancer.

EXAMPLE 25

VEGF$_{121}$/rGelonin Inhibits Intrafemoral PC3 Tumor Growth and Reduces the Number of Osteoclasts The anti-tumor effect of the fusion protein VEGF$_{121}$/rGel was evaluated in a prostate cancer bone model by injecting PC3 tumor cells into the distal epiphysis of the right femur of athymic nude mice. The animals were anesthetized with intramuscular injections of ketamine (100 mg/kg) plus acepromazine (2.5 mg/kg). Aliquots of 5×10$^4$ of PC3 cells were diluted in 5 μl of growth medium and then injected into the distal epiphysis of the right femur of each mouse using a 28-gauge Hamilton needle. The contralateral femur was used as an internal control. Twenty mice were randomized into two treatment groups. Treatment began one week after tumor placement. The animals were treated (i.v.) with the following protocol: Group 1, 200 μl saline every other day for nine days (5 treatments); Group 2, 180 μg VEGF$_{121}$/rGel in 200 μl saline every other day for nine days (5 treatments). Mice were monitored weekly for tumor bulk and bone loss. Tumor growth was monitored by X-ray analysis and animals with large osteolytic lesions or bone lysis were sacrificed.

Figure 25:
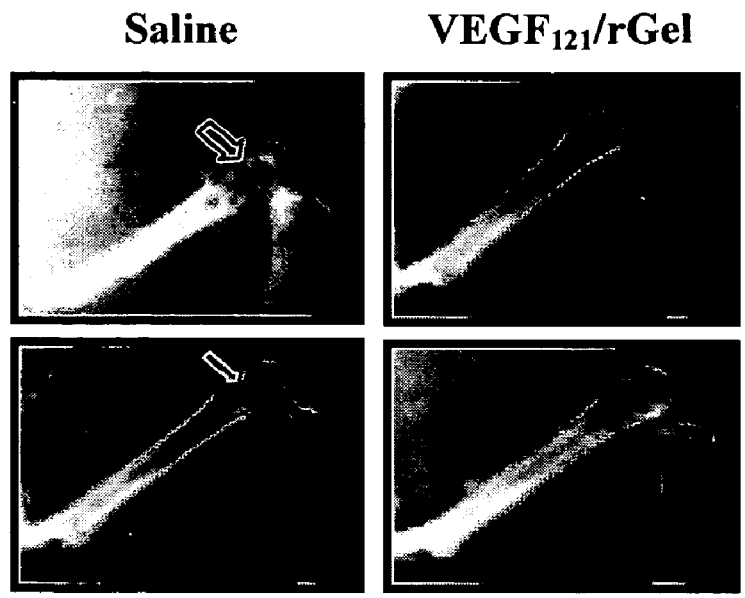
FIG. 25 shows the effect of VEGF$_{121}$/rGel in nude mice with PC-3 tumors in bone. Mice treated with either saline or VEGF$_{121}$/rGel were analyzed by X-ray. Arrows indicate location of osteolytic lesion only in the saline-treated animals.
Figure 26:
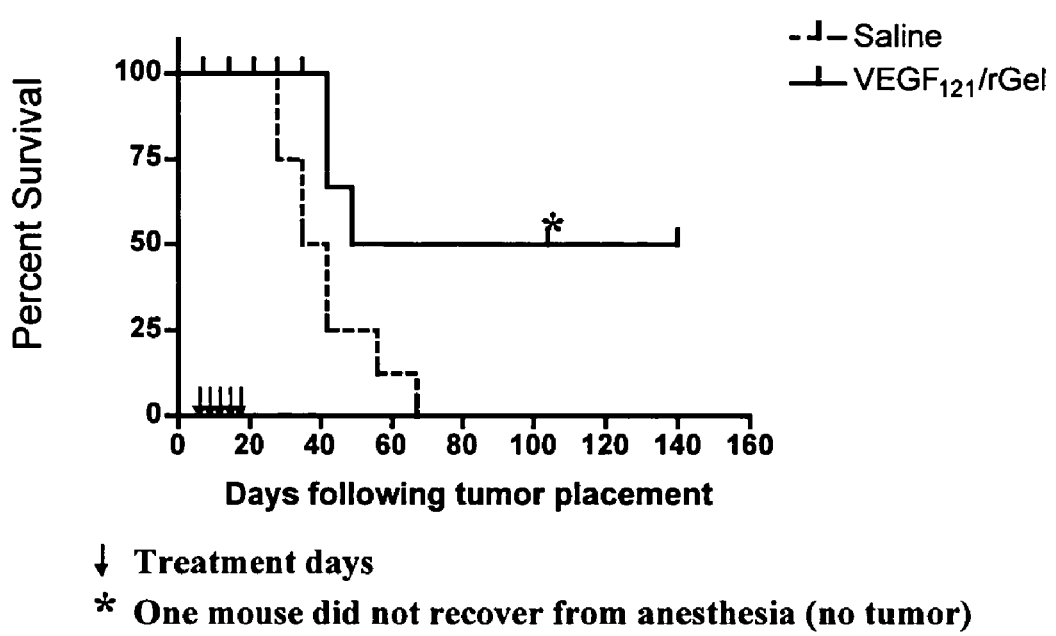
FIG. 26 shows VEGF$_{121}$/rGel strongly inhibits the growth of prostate cancer cells PC-3 placed in the bone micro-environment in mice. Animals were anesthesized prior to injection of 50,000 PC-3 cells into the distal epipysis of the right femur. Treatment with VEGF$_{121}$/rGel or saline (control) began one week after tumor placement. Maximum tolerated dose of VEGF$_{121}$/rGel was utilized and administered i.v. as shown. Tumor growth was monitored by X-ray and animals with large osteolytic lesions or bone lysis were sacrificed. All control mice were sacrificed by day 67. In contrast, 50% of the VEGF$_{121}$/rGel-treated mice survived past day 140 without sign of osteolysis. Asterisk indicates one mouse (without tumor) did not recover from anesthesia.

Prostate cancer-bearing mice treated with saline developed osteolytic lesions (FIG. 25) and 50% survival occurred 40 days after tumor placement (FIG. 26). In contrast, treatment with VEGF$_{121}$/rGel resulted in suppression of intrafemoral tumor growth as assessed radiologically (FIG. 25) and 50% of the VEGF$_{121}$/rGel-treated mice survived past 140 days without sign of osteolysis (FIG. 26).

Figure 27:
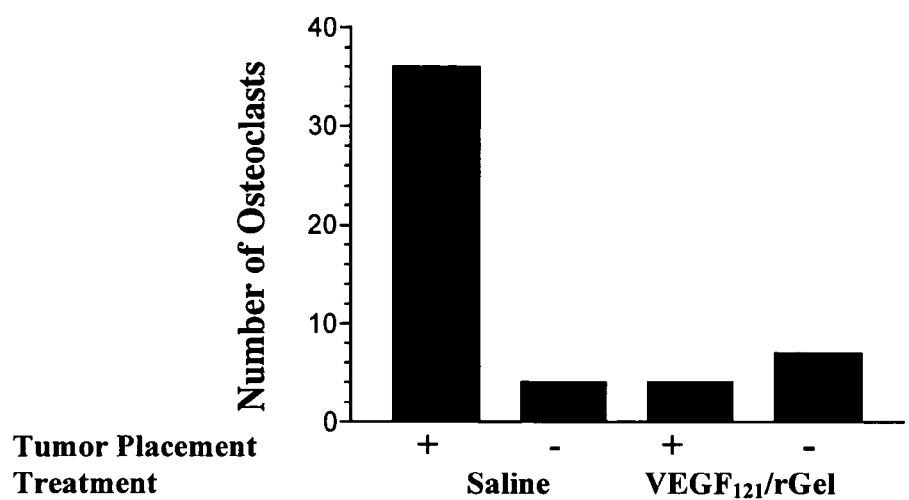
FIG. 27 shows the effect of VEGF$_{121}$/rGel on the number of osteoclasts in bone sections of nude mice with PC-3 tumor cells.
Figure 28:
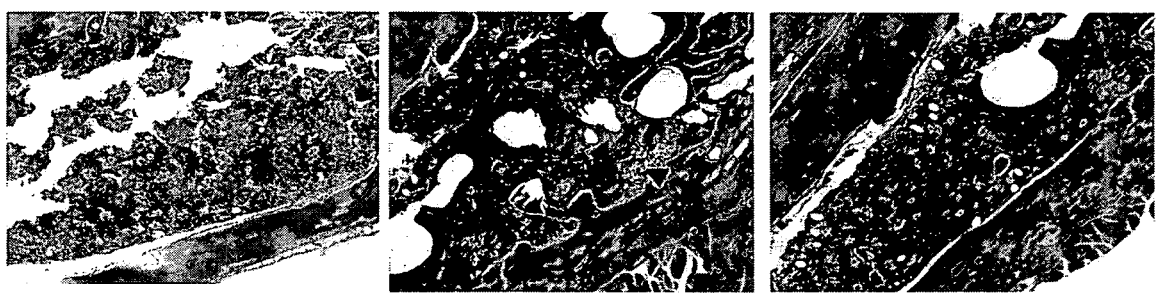
FIG. 28 shows H&E staining of bone tissue two weeks after injection of PC-3 tumor cells. Mice treated with saline show proliferation of PC-3 tumor cells (left panel). In contrast, mice treated with VEGF$_{121}$/rGel show isolated pockets of PC-3 tumor cells (middle panel). Shown on the right is a representative bone section from a VEGF$_{121}$/rGel-treated mouse.

TRAP staining of bone sections revealed a dramatic increase in the number of osteoclasts in the tumor-bearing leg of mice treated with saline (FIG. 27). In contrast, bone sections of VEGF$_{121}$/rGel-treated mice showed a normalized number of osteoclasts, suggesting that VEGF$_{121}$/rGel may play a role in inhibiting osteoclast proliferation and/or differentiation. H&E staining showed PC3 cells proliferating in bone sections of mice treated with saline (FIG. 28, left panel) and in isolated pockets in some bone sections from VEGF$_{121}$/rGel-treated mice (FIG. 28, arrows, middle panel). FIG. 28, right panel, showed bone sections without any tumor cells from mice treated with VEGF$_{121}$/rGel.

EXAMPLE 26

VEGF$_{121}$/rGelonin Is Cytotoxic to Osteoclast Precursor Cells and Inhibits Differentiation to Mature Osteoclasts To examine the effect of VEGF$_{121}$/rGel in the bone microenvironment and test if VEGF$_{121}$/rGel may be targeting osteoclast precursor cells in vivo, the effect of VEGF$_{121}$/rGel fusion toxin on RANKL-induced osteoclast differentiation of osteoclast precursor RAW cells was examined in vitro. The effect of VEGF$_{121}$/rGel and rGel on M-CSF and RANKL-dependent osteoclast differentiation of primary bone marrow monocytes was also examined.

M-CSF dependent, non-adherent bone marrow cells representing cells of the monocyte lineage were isolated from tibiae and femora of mice. Tibiae and femora were aseptically dissected from mice. Bone ends were cut off, and marrow was forced out in MEM supplemented with 10% FBS and penicillin. The marrow suspension was filtered through a fine meshed sieve to remove bone particles and gentle pipetting was used to obtain a single cell suspension. The bone marrow cells were washed and plated at 1.5-2×10$^7$ cells/10 cm dish with 10 ml of MEM and cultured for 24 h in the presence of M-CSF (10 ng/ml). On the following day, non-adherent cells were re-suspended in MEM, plated at 2.5×10$^4$ cells per well in a 96 well dish for cytotoxicity assays or 5×10$^3$ per well in a 96 well plate for osteoclast assays. The cells were then cultured for 3 days in the presence of 10 ng/ml M-CSF before they were used for further experiments.

For in vitro osteoclast differentiation assay, primary bone marrow monocytes or RAW 264.7 cells were cultured in 96-well dishes at a density of 5×10$^3$ cells per well and 3×10$^3$ cells per well, respectively. RAW 264.7 cells were cultured with 100 ng/ml RANKL. Primary bone marrow monocytes were cultured with 10 ng/ml M-CSF and 100 ng/ml RANKL and culture medium was changed on day 3. Osteoclast differentiation was determined by counting the total number of multinucleated (3 nuclei), tartrate-resistant acid phosphatase (TRAP)-positive cells per well on day 5 using Leucocyte Acid phosphatase kit (Sigma-Aldrich, St. Louis, Mo.).

Figure 29:
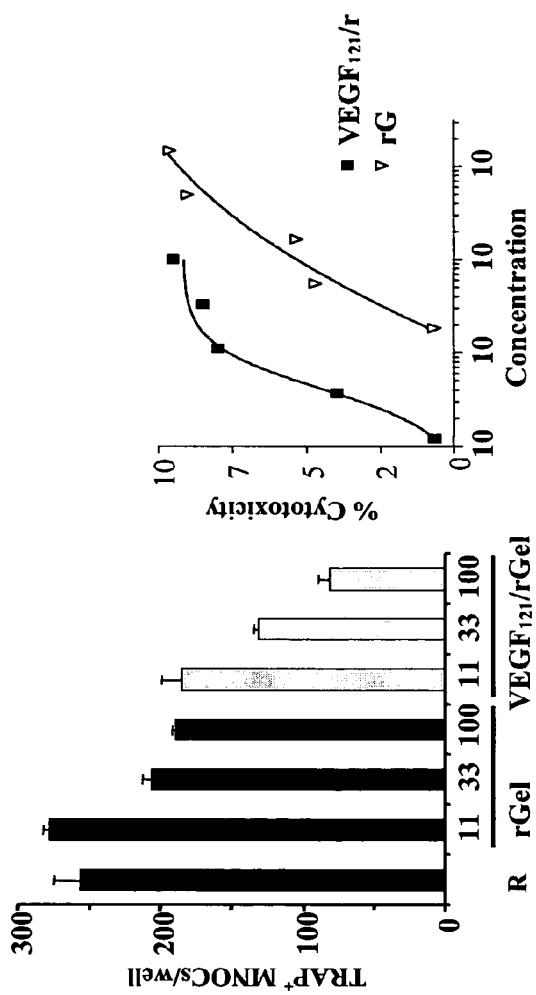
FIG. 29 shows the effects of VEGF$_{121}$/rGel and rGel on RANKL-mediated osteoclast formation. Each experiment was performed in triplicate. The data shown is representative of three separate experiments. RAW cells (1×10$^4$/well) were cultured overnight in 24-well plates. The cells were treated with RANKL (100 ng/ml) in the absence or presence of increasing concentrations of VEGF$_{121}$/rGel or rGel. After 4 days, the cells were fixed, TRAP stained, and the total number of TRAP$^+$ osteoclasts was counted. Cytotoxicity of VEGF$_{121}$/rGel and rGel was assessed in 96-well plates as described above.

As shown in FIG. 29, increasing concentrations of VEGF$_{121}$/rGel, but not rGel, caused a dramatic decrease of TRAP$^+$ multi-nucleated osteoclasts in the RAW 264.7 cell culture. The observed effect was not mediated by either VEGF$_{121}$ or gelonin alone but was a characteristic unique to the VEGF$_{121}$/rGel fusion protein. The IC$_{50}$ of VEGF$_{121}$/rGel on dividing RAW cells was 40 nM as compared with 900 nM for rGel itself, indicating the presence of a receptor for VEGF$_{121}$.

Figure 30:
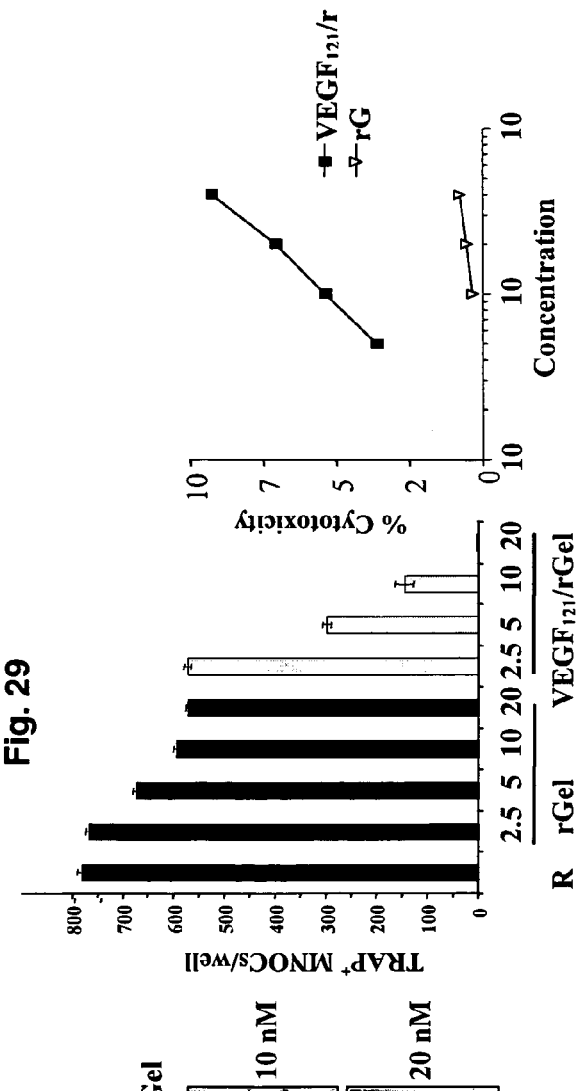
FIG. 30 shows the effects of VEGF$_{121}$/rGel and rGel on M-CSF and RANKL-mediated differentiation of primary bone marrow monocytes. Each experiment was performed in triplicate. The data shown is representative of three separate experiments. Non-adherent mouse bone marrow-derived monocytes were isolated from the tibia and femur of mice and plated in 24-well plates (5×10$^4$/well) and incubated with M-CSF (10 ng/ml). After 3 days, the cells were washed and stimulated with M-CSF (10 ng/ml) in the absence or presence of increasing concentrations of VEGF$_{121}$/rGel or rGel and RANKL (100 ng/ml). Medium was changed on day 3. On day 5 the cells were fixed, stained for TRAP, and the total number of TRAP$^+$ osteoclasts was counted. Cytotoxicity of VEGF$_{121}$/rGel and rGel was assessed in 96-well plates as described above.

Similar to the effects on RAW cells, VEGF$_{121}$/rGel inhibited M-CSF and RANKL-mediated osteoclast differentiation of primary mouse bone marrow-derived osteoclast progenitors in a dose-dependent manner (FIG. 30). rGel had little effect. While RAW cells do not require M-CSF for their survival or differentiation into osteoclasts, primary bone marrow-derived monocytes require exogenous M-CSF for their survival. VEGF$_{121}$/rGel, but not rGel, inhibited the M-CSF-dependent survival of the monocytes. As with RAW cells, the IC$_{50}$ of VEGF$_{121}$/rGel (10 nM) was lower than the IC$_{50}$ of rGel (FIG. 30, exact IC$_{50}$ not determined) on bone marrow-derived monocytes. Furthermore, VEGF$_{121}$/rGel exhibited a greater inhibitory effect on the primary monocytes as compared to RAW cells. Thus VEGF$_{121}$/rGel not only inhibited RANKL-mediated differentiation of osteoclast precursors, it also exhibited cytotoxicity towards undifferentiated cells in a targeted manner.

EXAMPLE 27

Localization of VEGF$_{121}$/rGelonin into Osteoclast Precursor Cells is Mediated by Flt-1

Figure 31A:
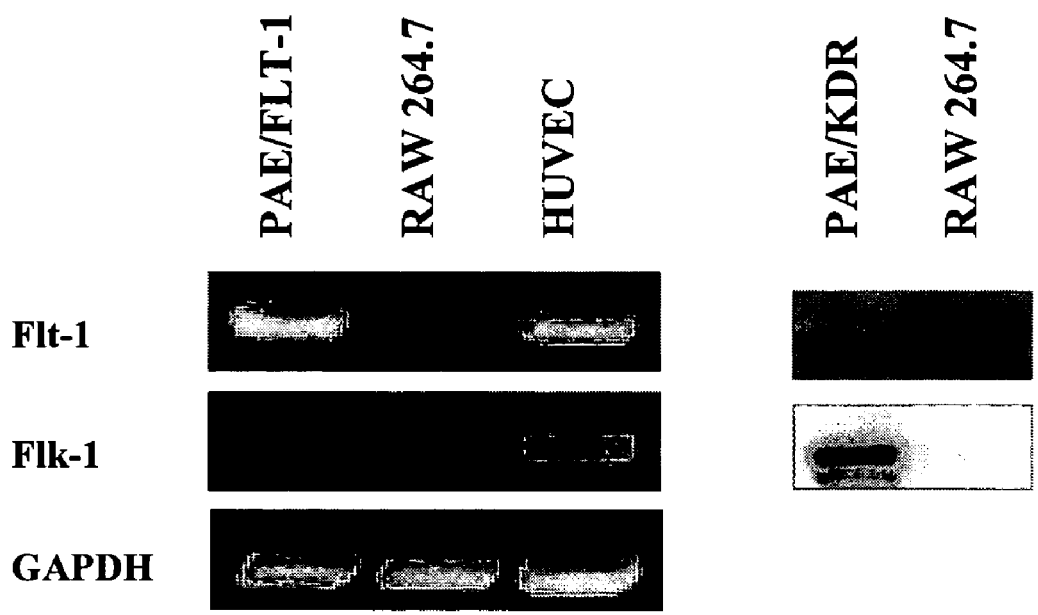
FIGS. 31A-C show PCR and Western blot analysis of osteoclast precursor cells. RAW 264.7 cells express Flt-1 but not Flk-1. Endothelial cells that express Flt-1 (PAE/Flt-1), KDR (PAE/KDR) or both (HUVEC) were used as controls (FIG. 31A). Bone marrow-derived cells of monocyte/macrophage lineage express Flt-1 but not Flk-1/KDR. Bone marrow-derived monocyte stimulated to differentiate by RANKL were harvested at the time points indicated and analyzed by PCR (FIG. 31B). PCR analysis showed that Flt-1 mRNA is down-regulated during RANKL-mediated osteoclasts differentiation of bone marrow-derived monocyte (FIG. 31C).
Figure 31B:
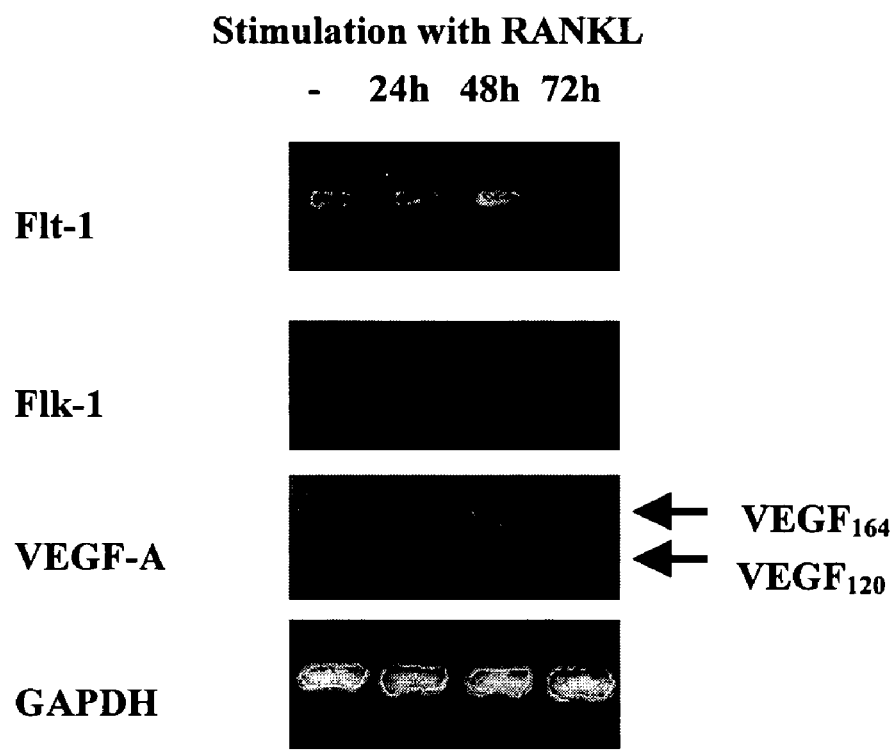

Because VEGF$_{121}$/rGel exhibited targeted cytotoxicity on RAW and bone marrow-derived monocytes, the levels of expression of VEGF$_{121}$ receptors Flk-1/KDR and Flt-1 were examined in these cells. PCR analysis indicated low levels of Flt-1, but no Flk-1/KDR transcript, in RAW cells (FIG. 31A). Western blot analysis of RAW cells validated this observation. PCR analysis of unstimulated bone marrow-derived monocytes showed a higher level of the Flt-1 transcript as compared to RAW cells (FIG. 31B). No Flk-1/KDR was detected in bone marrow-derived monocytes.

Figure 31C:
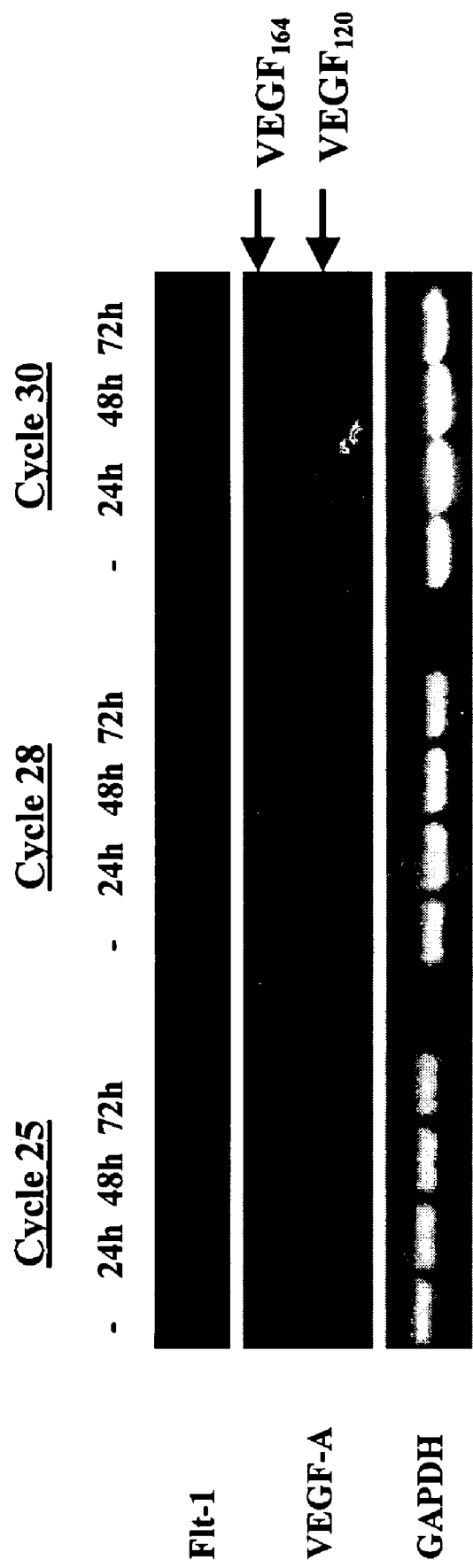

PCR analysis of VEGF-A isoforms indicated the presence of low levels of VEGF164 and VEGF120. VEGF189 and VEGFx were not detected. Stimulation of RANKL-mediated osteoclastogenesis did not change the levels of Flk-1/KDR or VEGF-A isoforms, but downregulated Flt-1 transcript by 72 h after addition of RANKL (FIG. 31B). The downregulation of Flt-1 mRNA in bone marrow-derived monocytes following stimulation of osteoclastogenesis by RANKL was confirmed by RT-PCR analysis (FIG. 31C).

Based on the observation that the cytotoxicity of VEGF$_{121}$/rGel on endothelial cells is mediated through Flk-1/KDR and not Flt-1, it is hypothesized that Flk-1/KDR plays an important but as yet unknown role in RANKL-mediated osteoclastogenesis. However, it is also possible that the biology of VEGF receptors is different in osteoclasts compared to endothelial cells, and VEGF$_{121}$/rGel is able to inhibit formation of osteoclasts via Flt-1. To this end, whether VEGF$_{121}$/rGel was delivered into the cytoplasm of the cells was examined by immunostaining.

To study internalization of VEGF$_{121}$/rGel into RAW cells, the cells were incubated with various concentrations of VEGF$_{121}$/rGel or rGel for various periods of time. To demonstrate receptor specificity, the cells were pre-treated with Flt-1 or Flk-1 neutralizing antibodies for one hour prior to treatment with VEGF$_{121}$/rGel or rGel. Glycine buffer (500 mM NaCl, 0.1 glycine, pH 2.5) was used to strip the cell surface of non-internalized VEGF$_{121}$/rGel. Cells were fixed with 3.7% formaldehyde and permeabilized with 0.2% Triton X-100. Non-specific binding sites were blocked with 5% BSA in PBS. The cells were then incubated with a rabbit anti-gelonin polyclonal antibody (1:200) followed by a TRITC-conjugated anti-rabbit secondary antibody (1:80). Nuclei were stained with propidium iodide (1 μg/ml) in PBS. The slides were fixed with DABCO media, mounted and visualized under fluorescence (Nikon Eclipse TS1000) and confocal (Zeiss LSM 510) microscopes.

As shown in FIG. 32, only RAW cells treated with VEGF$_{121}$/rGel, but not rGel, showed VEGF$_{121}$/rGel localization in the cytoplasm and this appears to account for the cytotoxic effect of this agent. The internalization of VEGF$_{121}$/rGel was tempered by addition of VEGF$_{121}$ as a competitor. Pretreatment of RAW cells with neutralizing antibodies to Flt-1, but not anti-Flk-1/KDR, inhibited the localization of VEGF$_{121}$/rGel into these cells.

To determine the role of VEGF$_{121}$ receptors in VEGF$_{121}$/rGel-mediated cytotoxicity of osteoclast precursor cells, bone marrow-derived monocytes were preincubated with neutralizing antibodies to Flt-1 or Flk-1/KDR for one hour prior to addition of VEGF$_{121}$/rGel for 72 h. Cell viability was not affected by the addition of up to 20 μg/ml anti-Flk-1 antibody (FIG. 33). However, neutralizing antibody to Flt-1 blocked the cytotoxic effects of VEGF$_{121}$/rGel in a dose-dependent manner (FIG. 33). Less than 2 μg/ml of antibody was sufficient to restore cell viability to 100% in the presence of 40 nM VEGF$_{121}$/rGel. Thus Flt-1, but not Flk-1/KDR, mediates VEGF$_{121}$/rGel cytotoxicity in osteoclast precursors. In addition, Flt-1, but not Flk-1/KDR mediates VEGF-A signaling in osteoclast precursor cells.

Figure 34:
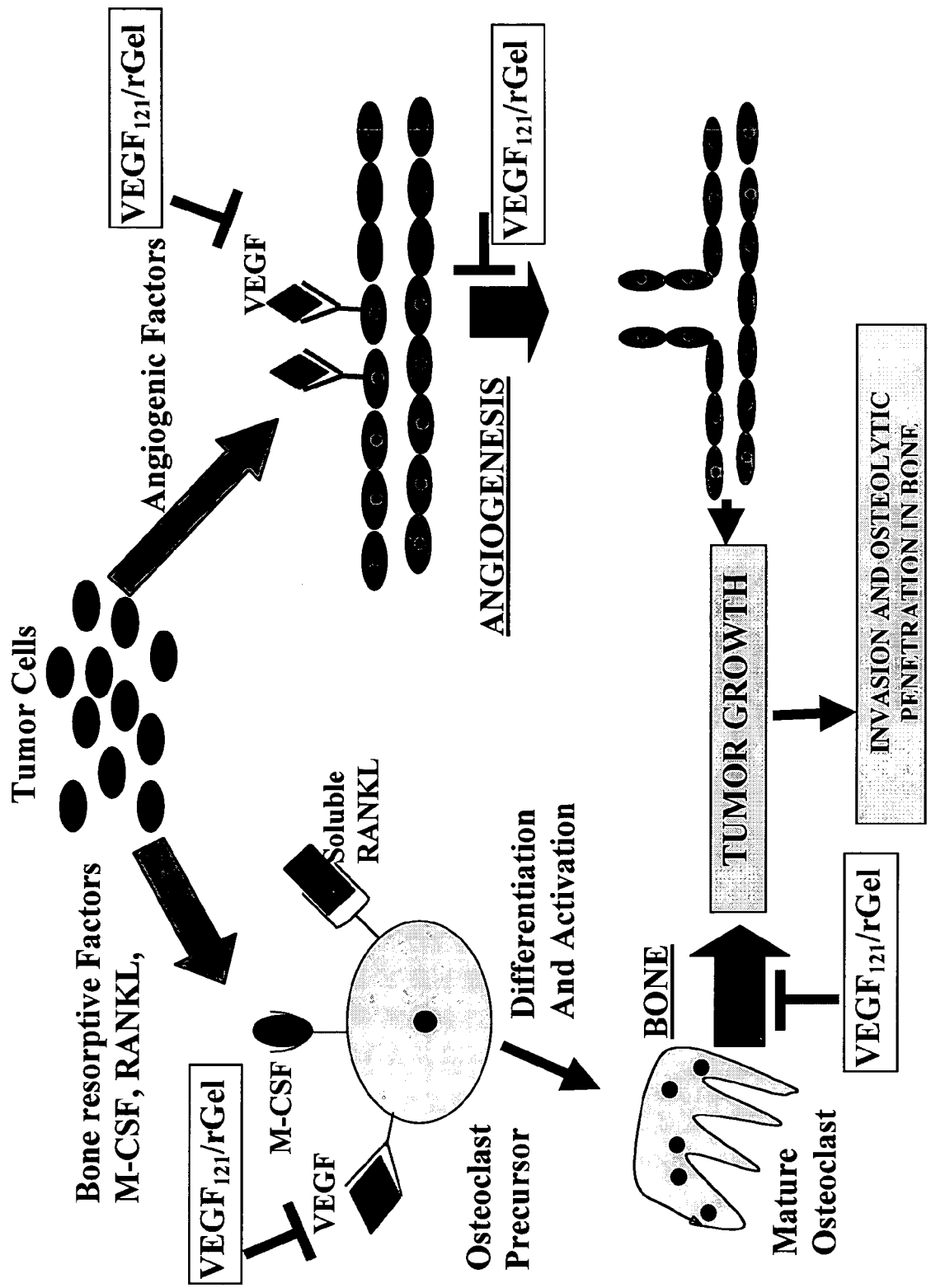
FIG. 34 proposes a role for VEGF in tumor invasion and osteolytic penetration in bone.
Figure 36:
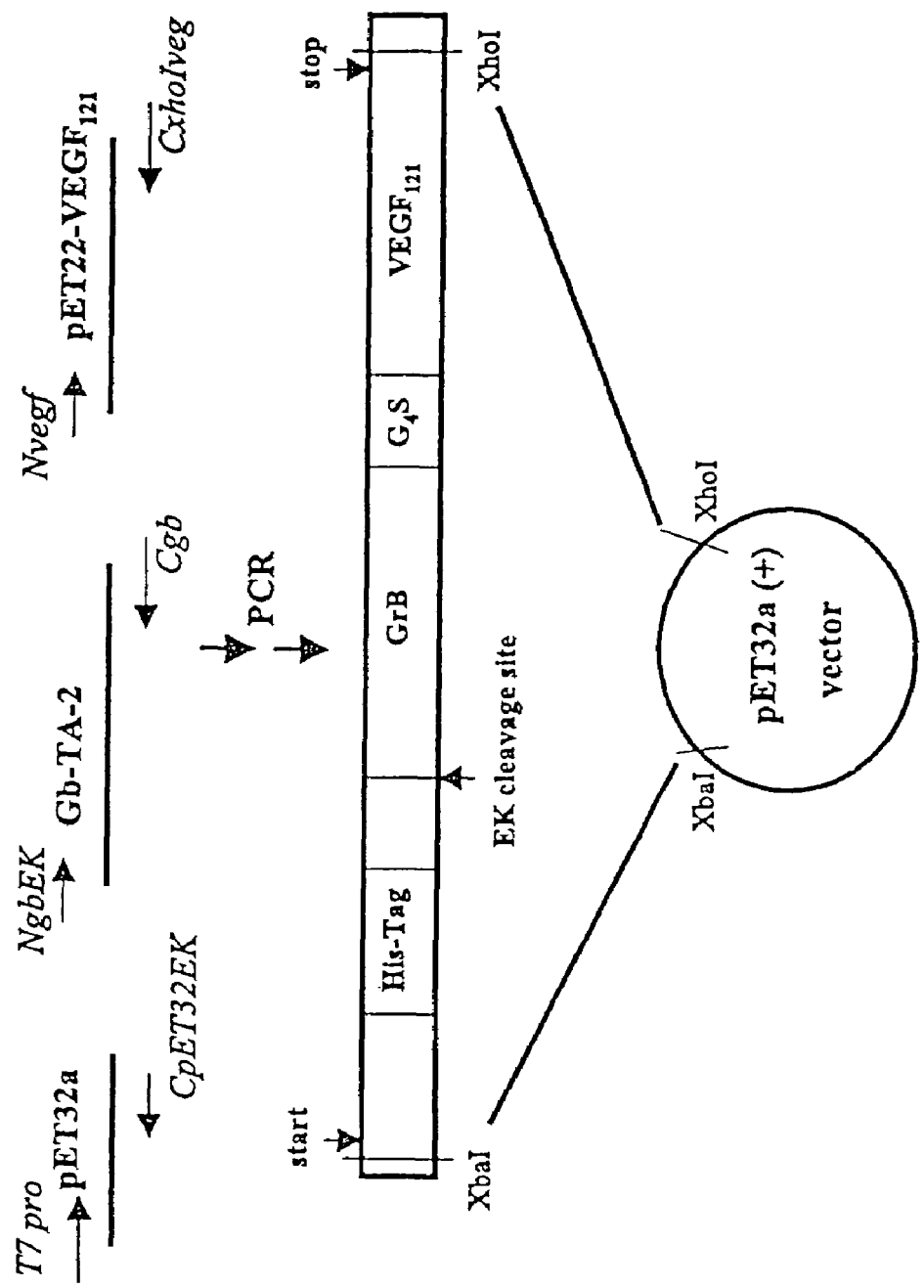
FIG. 36 shows the construction of GrB/VEGF$_{121}$ fusion toxin by PCR and insertion into the pET32a(+) vector. Mature granzyme B was attached to the recombinant VEGF$_{121}$ carrier via a flexible tether (G4S). A cleavage site for EK (DDDDK) was inserted upstream and adjacent to the first amino acid isoleucine of granzyme B. The fused gene fragment was then introduced into XbaI and XhoI sites of the pET32a(+) vector to form the expression vector pET32GrB/VEGF$_{121}$.

FIG. 34 proposes a role for VEGF in tumor invasion and osteolytic penetration in bone. Tumor growth following skeletal metastases requires proliferation of new blood vessels as well as resorption of bone. VEGF and its receptors play a critical role in both pathways and in the development of skeletal metastases. The fusion protein VEGF$_{121}$/rGel is a useful molecule to probe the roles of VEGF and its receptors, as it can prevent both angiogenesis and bone resorption by competing with VEGF as well as exerting cytotoxic effects.

EXAMPLE 28

Cloning of Human Granzyme B Gene and Construction of Granzyme B/VEGF$_{121}$ Fusion Gene The following examples describe a fusion construct of $VEGF_{121}$ and proapoptotic enzyme granzyme B (GrB) designed for specific delivery to tumor neovasculature. Human granzyme B gene was cloned from human cutaneous T-cell lymphoma (HuT-78) cells and then fused to $VEGF_{121}$ via a short, flexible tether using a PCR-based construction method. The fusion protein was expressed in *Escherichia coli* and purified by nickel-NTA metal affinity chromatography. The fusion protein GrB/$VEGF_{121}$ was characterized and the biological activities and mechanism were determined.

RNA from HuT-78 cells was isolated and target premature human granzyme B cDNA was amplified by reverse transcription-PCR using the following primers: NcoIgb, 5'-GGTGGCGGTGGCTCCATGGAACCAATC-CTGCTTCTG-3' (SEQ ID NO:5) and CxhoIgb, 5'-GCCAC-CGCCTCCCTCGAGCTATTAGTAGCGTTTCATGGT-3' (SEQ ID NO:6). The human granzyme B sequence with signal sequence was designated as premature granzyme B (~800 bp) (FIG. 35). The PCR product was then cloned into the PCR 2.1 TA vector designated as gbTA. The gbTA was transformed into INVaF' competent cells, and positive clones were screened by PCR. The DNA from positive clones was isolated and then sequenced. The correct clone was designated gbTA-2.

In cytotoxic cells, active granzyme B was generated from a zymogen by dipeptidyl peptidase I-mediated proteolysis, which removes the two residue (Gly-Glu) propeptide and exposes $Ile^{21}$. The amino-terminal Ile-Ile-Gly-Gly sequence of granzyme B is necessary for the mature, active granzyme B.

To construct GrB/$VEGF_{121}$ fusion gene, the coding sequence of granzyme B was amplified by PCR from $Ile^{21}$, effectively deleting the signal sequence and Gly-Glu domain. At the same time, a cleavage site for EK (DDDDK, SEQ ID NO:7) was inserted upstream and adjacent to $Ile^{21}$. Mature granzyme B was attached to the recombinant $VEGF_{121}$ carrier via flexible tether ($G_4S$). The fused gene fragment was then introduced into the XbaI and XhoI sites of the pET32a(+) to form the expression vector pET32GrB/$VEGF_{121}$ (FIG. 36). This vector contains a T7 promoter for high-level expression followed by a Trx.tag, a His.tag, a thrombin cleavage site, and an EK cleavage site for final removal of the protein purification tag. Once protein tag is removed by rEK digestion, the first residue (isoleucine) of mature granzyme B is exposed, thereby activating the granzyme B moiety of GrB/$VEGF_{121}$ construct.

The GrB/$VEGF_{121}$ fusion gene was constructed by an overlap PCR method. Briefly, granzyme B coding sequence was amplified from gbTA-2 using the following primers: NgbEK, 5'-GGTACCGACGACGACGACAAGAT-CATCGGGGGACATG AG-3' (SEQ ID NO:8) and Cgb, 5'-GGAGCCACCGCCACCGTAGCGTTTCATGGT-3'

(SEQ ID NO:9). These were designed to delete the signal sequence of premature granzyme B, insert an EK cleavage site at the amino terminus, and add a G4S linker sequence to the carboxyl terminus to serve as a link to the VEGF$_{121}$ gene. VEGF$_{121}$ sequence was amplified from a plasmid pET22-VEGF$_{121}$ (from. Dr. Philip Thorpe, University of Texas Southwestern Medical Center, Dallas, Tex.) using the following primers: Nvegf, 5'-GGTGGCGGTGGCTCCGCAC-CCATGGCAGAA-3' (SEQ ID NO:10) and CxhoI veg, 5'-AAGGCTCGTGTCGACCTCGAGTCATTACCG CCTCGGCTTGTC-3' (SEQ ID NO:11). To clone the fused genes into pET32a(+) vector with an EK site at the amino terminus of granzyme B, the fragment from pET32a(+) was amplified using the following primers: T7 promoter, 5'-TAATACGACTCACTATAG (SEQ ID NO:12) and CpET32EK, 5'-CTTGTCGTCGTCGTCGGTACCCA-GATCTGG-3' (SEQ ID NO:13). The primer has an EK site at carboxyl terminus overlapping with the amino terminus of the fused gene. Using overlap PCR, the fusion genes (EK-GrB/VEGF$_{121}$) were constructed using as primers the T7 promoter and CxhoI veg. Amplified fragments were purified, digested with XbaI and XhoI, and cloned into pET32a(+) vector, designed as pET32GrB/VEGF$_{121}$. A correct clone was chosen for transformation into AD$_{494}$ (DE$_3$) pLysS-competent cells for further induction and expression.

EXAMPLE 29

Expression and Purification of Granzyme B/VEGF$_{121}$ Fusion Protein

Bacterial colonies transformed with the constructed plasmid were grown in Luria broth medium (containing 400 mg/ml carbenicillin, 70 mg/ml chloramphenicol, and 15 mg/ml kanamycin) at 37° C. overnight at 240 rpm in a shaking incubator. The cultures were then diluted 1:100 in fresh Luria broth+antibiotics (200 mg/ml ampicillin, 70 mg/ml chloramphenicol, and 15 mg/ml kanamycin) and grown to $A_{600\ nm}$=0.6 at 37° C.; thereafter, isopropyl-1-thio-b-D-galactopyranoside was added to a final concentration of 100 mM and the cells were incubated at 37° C. for 2 h to induce fusion protein expression. The cells were harvested, resuspended in 10 mM Tris (pH 8.0), and stored frozen at −80° C. for later purification.

Thawed, resuspended cells were lysed by addition of lysozyme to a final concentration of 100 mg/ml with agitation for 30 min at 4° C. followed by sonication. Extracts were centrifuged at 186,000×g for 1 h. The supernatant containing only soluble protein was adjusted to 40 mM Tris, 300 mM NaCl, and 5 mM imidazole (pH 8.0) and applied to nickel-NTA agarose resin equilibrated with the same buffer. The nickel-NTA agarose was washed with 300 mM NaCl and 20 mM imidazole and the bound proteins were eluted with 500 mM NaCl and 500 mM imidazole. Absorbance (280 nm) and SDS-PAGE analyses were performed to determine the presence of the polyhistidine-tagged protein, designated as Pro-GrB/VEGF$_{121}$. The eluted Pro-GrB/VEGF$_{121}$ was dialyzed against 20 mM Tris-HCl (pH 7.4) and 150 mM NaCl. The GrB moiety of Pro-GrB/VEGF$_{121}$ was activated by the addition of bovine rEK to remove the polyhistidine tag according to the manufacturer's instructions (1 unit of rEK for cleavage of 50 mg protein incubated at room temperature for 16 h). The rEK was removed by EK capture agarose. The protein solution was then passed through a column containing Q-Sepharose to remove non-rEK-digested construct and non-specific proteins. The product was analyzed by SDS-PAGE to determine purity, and Bio-Rad protein assay was used to determine protein concentration. Samples were then aliquoted and stored at 4° C.

Figure 37B:
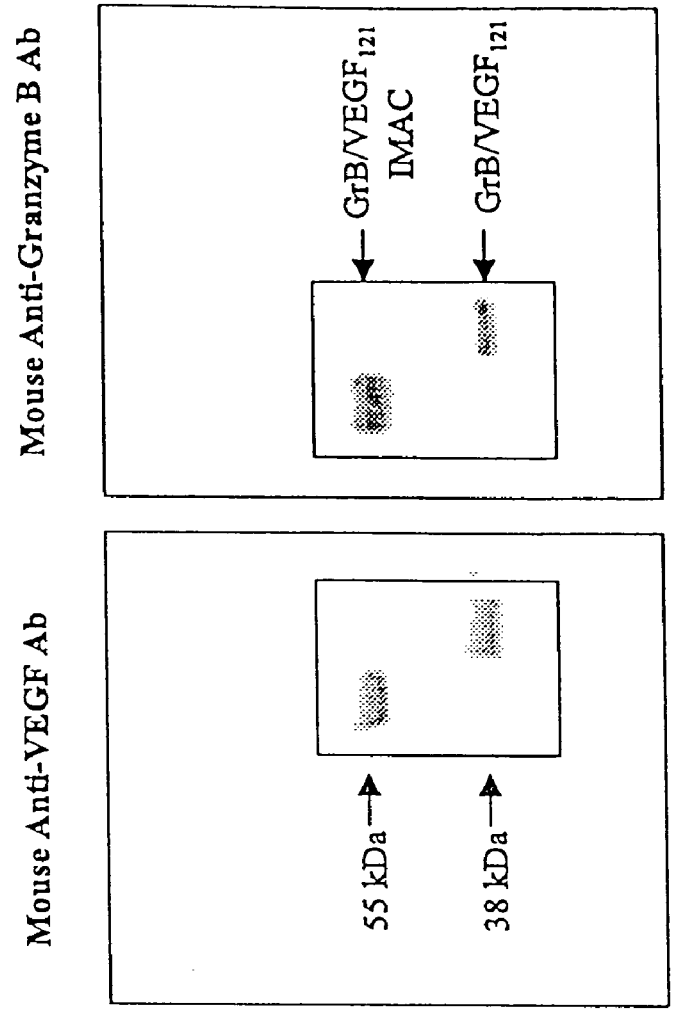
FIGS. 37A-B show bacterial expression, purification, and Western blot analysis of the GrB/VEGF$_{121}$ fusion toxin. 8.5% SDS-PAGE and Coomassie blue staining under reducing conditions showed that GrB/VEGF$_{121}$ was expressed as a 55-kDa molecule with tags and the size of the final purified GrB/VEGF$_{121}$ was ~38 kDa (FIG. 37A). Western blotting confirmed that the fusion protein reacted with either mouse anti-VEGF or mouse anti-GrB antibody (FIG. 37B).
Figure 37A:
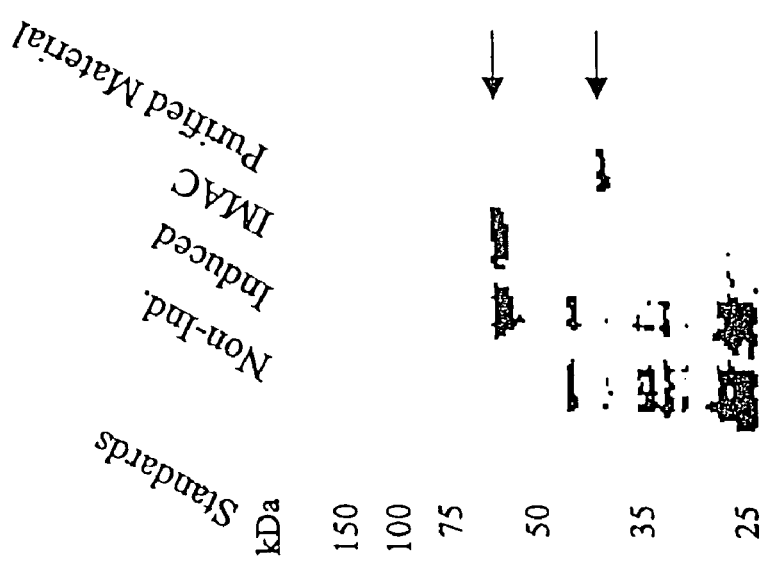

One liter of the culture typically yielded ~100 mg of the final purified GrB/VEGF$_{121}$ product. SDS-PAGE analysis showed that the final purified GrB/VEGF$_{121}$ fusion construct migrated under reducing conditions as a band at the expected molecular mass of 38 kDa (FIG. 37A). Specificity of the cleaved fusion protein was confirmed by Western blot using either VEGF121 mouse monoclonal antibody or GrB mouse monoclonal antibody (FIG. 37B).

EXAMPLE 30

Binding Activity of Granzyme B/VEGF$_{121}$ Fusion Protein

Binding activity of GrB/VEGF$_{121}$ was determined by ELISA. Ninety six-well plates coated with 50,000 cells/well of PAE/FLK-1, PAE/FLT-1, human melanoma A375M or human breast cancer SKBR3-HP cells were blocked by 5% BSA and then treated with purified GrB/VEGF$_{121}$ at various concentrations. After washing, the plates were incubated with either GrB antibody or VEGF$_{121}$ antibody followed by HRP-goat anti-mouse IgG. Then, the substrate 2,2'-azino-bis-3-ethylbenzthiazoline-6-sulfonic acid (ABTS) solution with 1 ml/ml of 30% H$_2$O$_2$ was added to the wells. Absorbance at 405 nm was measured after 30 min.

Figure 38A:
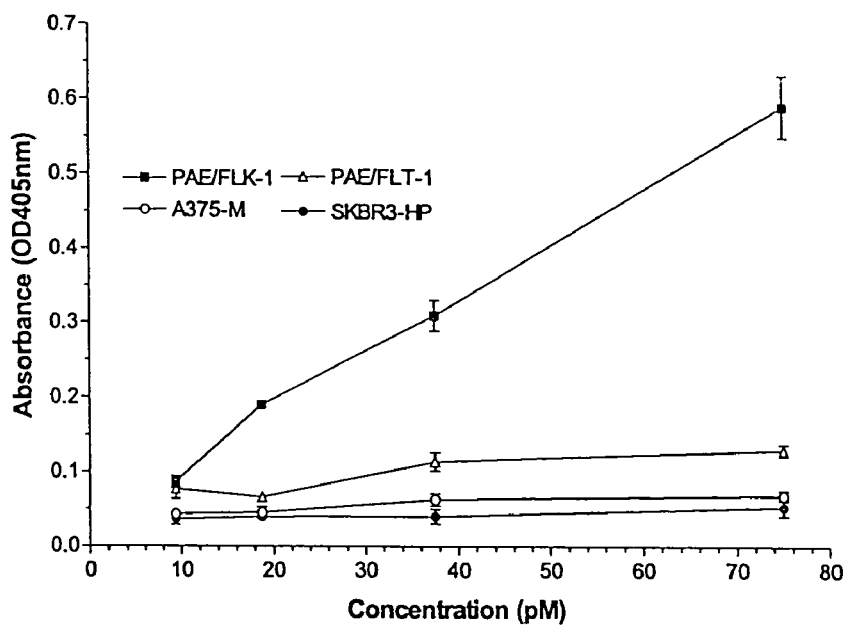
FIGS. 38A-B show GrB/VEGF$_{121}$ bound to PAE/FLK-1 cells but not to PAE/FLT-1 cells, A375M or SKBR3 cells. Binding of GrB/VEGF$_{121}$ to cells was assessed by 96-well ELISA plates coated with 50,000 cells/well of PAE/FLK-1, PAE/FLT-1, A375M or SKBR3 cells. The wells were blocked with 5% BSA and then treated with purified GrB/VEGF$_{121}$ at various concentrations. The wells were then incubated with either anti-GrB antibody (FIG. 38A) or anti-VEGF antibody (FIG. 38B) followed by HRP-goat anti-mouse IgG. ABTS solution with 1 ml/ml of 30% H$_2$O$_2$ were added to the wells, and absorbance at 405 nm was measured after 30 min.
Figure 38B:
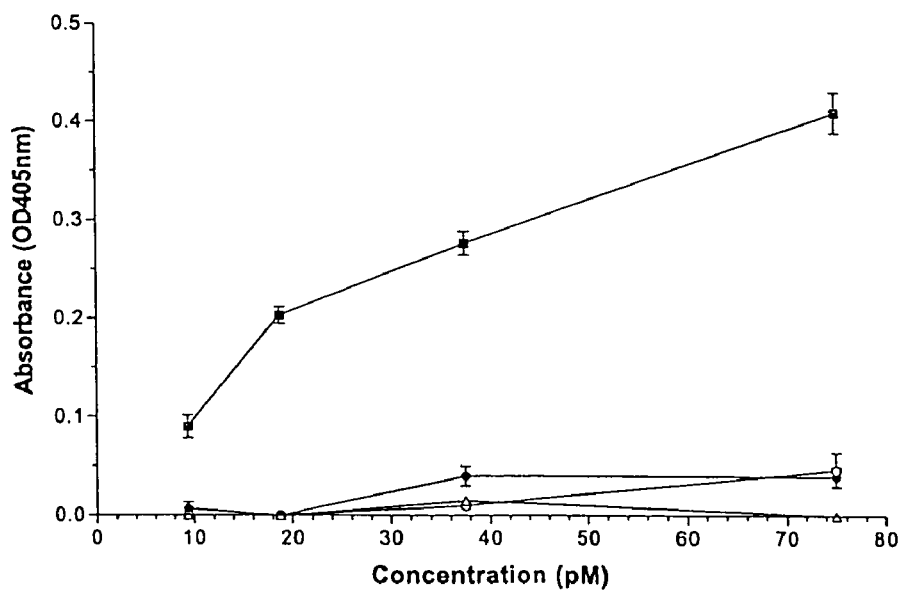

GrB/VEGF$_{121}$ specifically bound to PAE/FLK-1 cells. However, the protein did not bind to PAE/FLT-1 cells or to melanoma A375M or human breast cancer SKBR3-HP cells, as detected by either an anti-GrB mouse monoclonal antibody (FIG. 38A) or an anti-VEGF$_{121}$ mouse monoclonal antibody (FIG. 38B).

EXAMPLE 31

Internalization of Granzyme B/VEGF$_{121}$ Fusion Protein Assessed by Immunofluorescence Microscopy Cells were plated in 16-well chamber slides (Nunc, Nalge Nunc International, Naperville, Ill.) at 1×10$^4$ cells/well and incubated overnight at 37° C. in a 5% CO$_2$ air atmosphere. Cells were treated with 100 nM of GrB/VEGF$_{121}$ for 4 h and then washed briefly with PBS. The cell surface was stripped by incubation with glycine buffer (500 mM NaCl, 0.1 M glycine [pH 2.5]) and neutralized for 2 min with 0.5 M Tris (pH 7.4) followed by wash with PBS. Cells were fixed in 3.7% formaldehyde for 15 min at room temperature, permeabilized for 10 min in PBS containing 0.2% Triton X-100 and washed thrice with PBS. Samples were incubated with 3% BSA for 1 h at room temperature to block nonspecific binding sites before incubating with anti-GrB mouse monoclonal antibody (1:100 dilution) at room temperature for 1 h followed by incubation with FITC-coupled anti-mouse IgG (1:100 dilution) at room temperature for 1 h. The walls and gaskets of the chamber slide were then removed carefully. After air drying, the slide was mounted and analyzed under a Nikon Eclipse TS-100 fluorescence microscope. Photographs were taken with a scope-mounted camera.

Immunofluorescent staining clearly showed that the GrB moiety of GrB/VEGF$_{121}$ was delivered into the cytosol of PAE/FLK-1 but not into that of PAE/FLT-1 cells after treatment with GrB/VEGF$_{121}$ for 4 h (FIG. 39). Analysis of PAE/

FLK-1 cells treated for 24 and 48 h demonstrated no further increase in immunofluorescent staining over that observed at 4 h.

EXAMPLE 32

Cytotoxicity of Granzyme B/VEGF$_{121}$ Fusion Protein

The cytotoxicity of GrB/VEGF$_{121}$ was assessed against log-phase PAE/FLK-1 and PAE/FLT-1 cells in culture. PAE cells in Ham's F-12 medium with 10% fetal bovine serum were plated into 96-well plates at a density of $2.5 \times 10^3$ cells/ well and allowed to adhere for 24 h at 37° C. in 5% $CO_2$. After 24 h, the medium was replaced with medium containing different concentrations of GrB/VEGF$_{121}$ or VEGF$_{121}$/rGel. After 72 h, the effect of GrB/VEGF$_{121}$ or VEGF$_{121}$/rGel on the growth of cells in culture was determined using 2,3-bis [2-methoxy-4-nitro-5-sulfophenyl]-2H-tetrazolium-5-carboxanilide inner salt (XTT). Plates were read on a microplate ELISA reader at 540 nm.

Figure 40A:
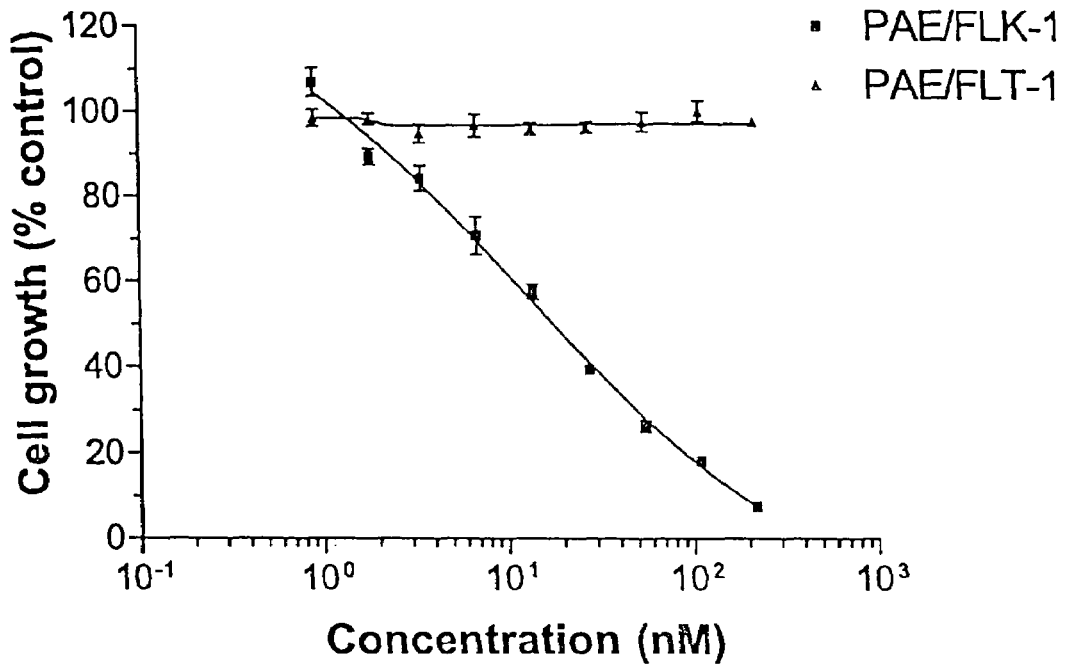
FIG. 40A shows cytotoxicity of the GrB/VEGF$_{121}$ fusion toxin on transfected endothelial cells. Log-phase PAE cells were plated into 96-well plates at a density of 2.5×10$^3$ cells/well and allowed to attach for 24 h. The medium was replaced with medium containing different concentrations of GrB/VEGF$_{121}$. After 72 h, the effect of fusiontoxin on the growth of cells in culture was determined using XTT. Plates were read on a microplate ELISA reader at 540 nm. IC$_{50}$ of GrB/VEGF$_{121}$ was ~10 nM on PAE/FLK-1 cells; it was not cytotoxic on PAE/FLT-1 cells.

An IC$_{50}$ effect was found at a concentration of ~10 nM on PAE/FLK-1 cells. However, no cytotoxic effects were found on PAE/FLT-1 cells at doses up to 200 nM (FIG. 40A). By comparison, the cytotoxic effects of another fusion toxin, VEGF$_{121}$/rGel, were relatively greater (on a molar basis) against target cells in culture and demonstrated specific cytotoxicity against PAE/FLK-1 cells at an IC$_{50}$ of ~1 nM.

The growth inhibitory effects of GrB/VEGF$_{121}$ on the proliferation of PAE cells were evaluated by clonogenic assay. Briefly, $5 \times 10^5$ PAE cells/ml were incubated at 37° C. and 5% $CO_2$ for 72 h with different concentrations of either GrB/ VEGF$_{121}$ or 100 nM of irrelevant fusion protein GrB/ scFvMEL. Cells were then washed with PBS, trypsinized, counted by hemacytometer, and diluted serially. The serial cell suspensions were then plated in triplicate and cultured in six-well plates for 5-7 days. Cells were stained with crystal violet and colonies consisting of >20 cells were counted using an inverted light microscope. Growth inhibition was defined as the percentage of cell growth/number of colonies in treated samples in relation to that in the nontreated control sample.

Figure 40B:
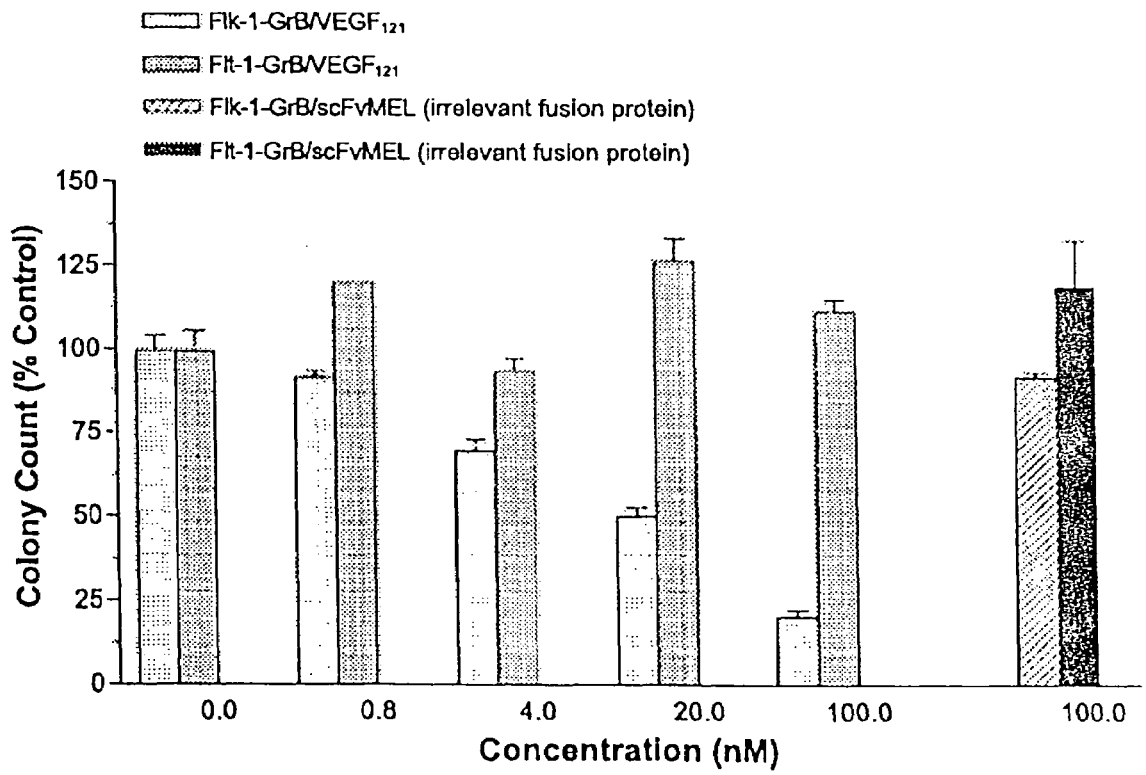
FIG. 40B shows growth inhibitory effects of GrB/VEGF$_{121}$ as determined by colony-forming assay. PAE cells (5×10$^5$ cells/ml) were incubated at 37° C. and 5% CO$_2$ for 72 h with different concentrations of GrB/VEGF$_{121}$ and 100 nM of irrelevant fusion protein GrB/scFvMEL. Cells were then washed with PBS, trypsinized, counted, and diluted serially. The serial cell suspensions were then plated in triplicate and cultured in six-well plates for 5-7 days. Cells were stained with crystal violet and colonies consisting of >20 cells were counted. The results are shown as percentage of colonies in relation to the number of colonies formed by untreated cells.

In the clonogenic assay (FIG. 40B), the concentration of GrB/VEGF$_{121}$ which suppressed cell colony growth by 50% (IC$_{50}$) was determined to be ~20 nM on PAE/FLK-cells. In contrast, there was no effect on colony growth of PAE/FLT-1 cells at concentrations of GrB/VEGF$_{121}$ up to 100 nM. There was also no effect of irrelevant fusion protein GrB/scFvMEL targeting human melanoma cells on colony growth of PAE cells at concentrations of 100 nM.

EXAMPLE 33

GrB/VEGF$_{121}$ Induced Apoptosis as Measured by TUNEL Assay

Cleavage of genomic DNA during apoptosis may yield double-stranded, low molecular mass DNA fragments as well as single-strand breaks (nicks) in high molecular mass DNA. The DNA strand breaks can be identified by labeling free 3' hydroxyl termini with modified nucleotides in an enzymatic reaction. Cells ($1 \times 10^4$ cells/well) were treated with GrB/ VEGF$_{121}$ at the IC$_{50}$ concentration for different times (24 and 48 h) and washed briefly with PBS. Cells were fixed with 3.7% formaldehyde at room temperature for 20 min, rinsed with PBS, permeablized with 0.1% Triton X-100, 0.1% sodium citrate on ice for 2 min, and washed with PBS twice. Cells were incubated with TUNEL reaction mixture at 37° C. for 60 min followed by incubation with Converter-AP at 37° C. for 30 min and finally treated with Fast Red substrate solution at room temperature for 10 min. After the final wash step, the slides were mounted and analyzed for nucleus staining of apoptotic cells under a light microscope with 400× magnification.

Figure 41A:
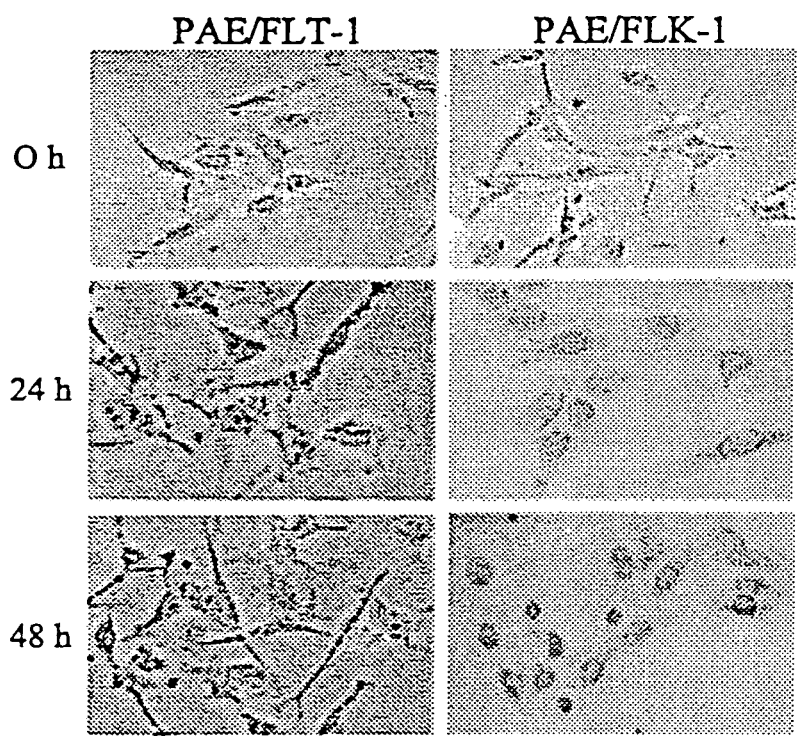
FIGS. 41A-B show GrB/VEGF$_{121}$ induces apoptosis on PAE/FLK-1 cells. Cells (1×10$^4$ cells/well) were treated with GrB/VEGF$_{121}$ at an IC$_{50}$ concentration for different times (0, 24, and 48 h) and washed with PBS. Cells were fixed with 3.7% formaldehyde and permeabilized with 0.1% Triton X-100 and 0.1% sodium citrate. Cells were incubated with TUNEL reaction mixture, incubated with Converter-AP, and finally treated with Fast Red substrate solution. The slides were analyzed under a light microscope. Apoptosis cells were stained red (400×) (FIG. 41A).
Figure 41B:
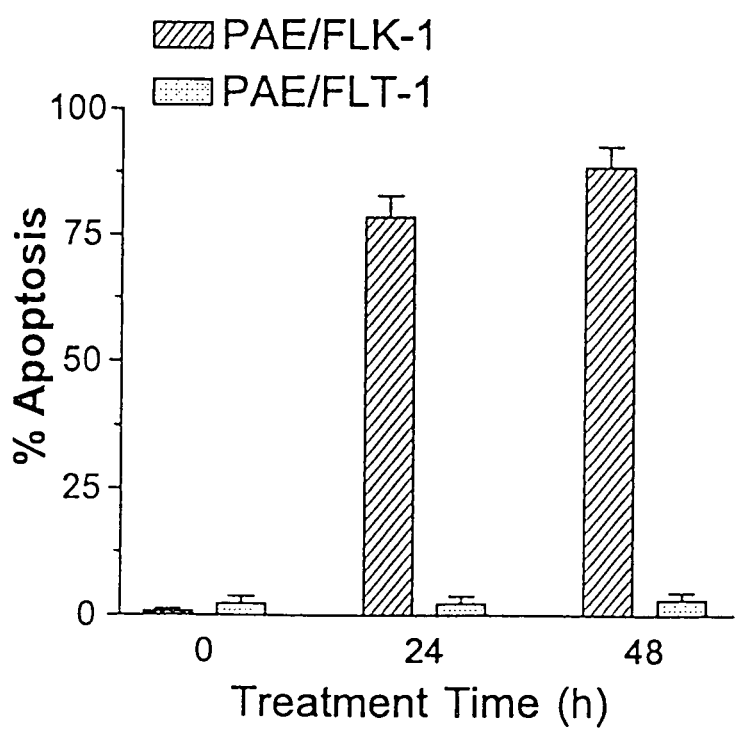

TUNEL assay produced positive results on GrB/VEGF$_{121}$-treated PAE/FLK-1 cells at 24 h (75%) and 48 h (85%) but not on GrB/VEGF$_{121}$-treated PAE/FLT-1 cells (10%) (FIG. 41), indicating that GrB/VEGF$_{121}$ induced apoptosis in PAE/ FLK-1 cells.

EXAMPLE 34

GrB/VEGF$_{121}$ Treatment Results in Cytochrome c Release and Bax Translocation PAE cells ($5 \times 10^7$) were treated with GrB/VEGF$_{121}$ at concentrations of 0.1 and 20 nM for 24 h. After cells were washed with 10 ml of ice-cold PBS, they were resuspended with 0.5 ml of 1× cytosol extraction buffer mix containing DTT and protease inhibitors and incubated on ice for 10 min. Cells were homogenized in an ice-cold glass homogenizer. The homogenate was centrifuged at 700×g for 10 min at 4° C. The supernatant was transferred to a fresh 1.5 ml tube and centrifuged at 10,000×g for 30 min at 4° C. The supernatant was collected and labeled as cytosolic fraction. The pellet was resuspended in 0.1 ml mitochondrial extraction buffer mix containing DTT and protease inhibitors, vortexed for 10 s, and saved as mitochondrial fraction. Protein concentrations were determined by using Bio-Rad Bradford protein assay. Aliquots of 30 mg from each cytosolic and mitochondrial fraction isolated from non-treated and treated cells were loaded on a 15% SDS-PAGE. Standard Western blot procedure was performed, and the blot was probed with mouse anti-cytochrome c antibody (1 mg/ml) or mouse anti-Bax antibody (1 mg/ml).

Figure 42:
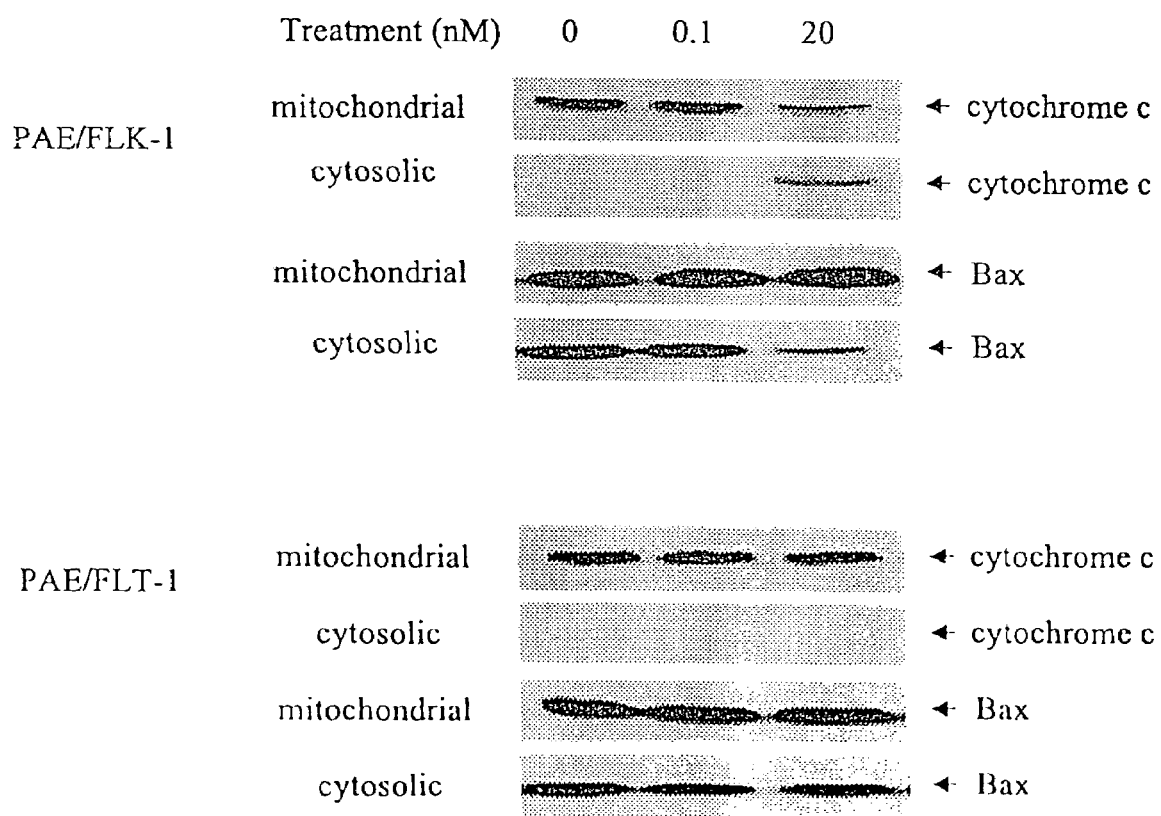
FIG. 42 shows granzyme B/VEGF$_{121}$ induces cytochrome c release from mitochondria to cytosol and Bax translocation from cytosol to mitochondria. PAE cells (5×10$^7$) were treated with granzyme B/VEGF$_{121}$ at concentrations of 0, 0.1, and 20 nM for 24 h. Cells were collected, and the cytosolic and mitochondrial fractions were isolated as described below. Fractions of 30 mg each from non-treated and treated cells were loaded onto 15% SDS-PAGE gels, and standard Western blotting procedure was performed. The blot was probed with anti-cytochrome c antibody or anti-Bax antibody.

Western blot studies demonstrated that cytochrome c was released from mitochondria into the cytosol after treating PAE/FLK-1 cells with 20 nM GrB/VEGF$_{121}$, but this effect was not observed on PAE/FLT-1 cells (FIG. 42). Bax was found to be normally present in both cytosol and mitochondria of untreated PAE cells. However, when PAE/FLK-1 cells were treated with 20 nM of GrB/VEGF$_{121}$, Bax levels decreased in cytosol and increased in mitochondria. This effect was not observed on PAE/FLT-1 cells (FIG. 42).

EXAMPLE 35

Granzyme B/VEGF$_{121}$ Induces DNA Laddering

PAE cells were plated onto six-well plates ($2 \times 10^5$ cells/ well). Twenty-four hours later, cells were shifted to fresh culture medium containing 20 nM of GrB/VEGF$_{121}$ (1.5 ml/well). After 24 h of incubation at 37° C., DNA was extracted and purified with DNA ladder kit (Roche) and fractionated on 1.5% agarose gels.

Figure 43:
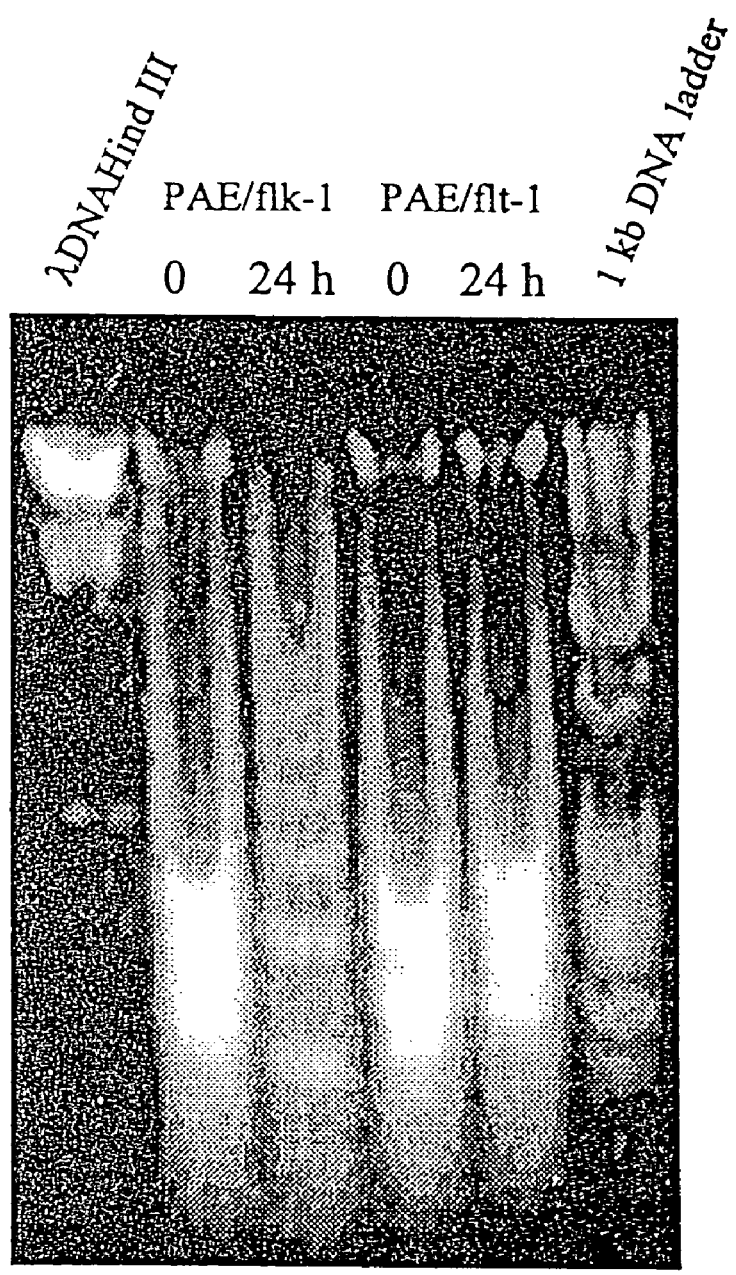
FIG. 43 shows GrB/VEGF$_{121}$ induces DNA laddering in PAE/FLK-1 cells. Cells were plated into six-well plates at a density of 2×10$^5$ cells/well and exposed to 20 nM GrB/VEGF$_{121}$ for 24 h. DNA was isolated from cell lysates and fractionated on 1.5% agarose gel.

DNA laddering indicative of apoptosis was observed after a 24-h exposure with GrB/VEGF$_{121}$ on PAE/FLK-1 cells. As expected, there was no DNA laddering detected on PAE/ FLT-1 cells after treatment with the fusion construct (FIG. 43).

EXAMPLE 36

Granzyme B/VEGF$_{121}$ Activates Caspases on Porcine Aortic Endothelial Cells

Figure 44:
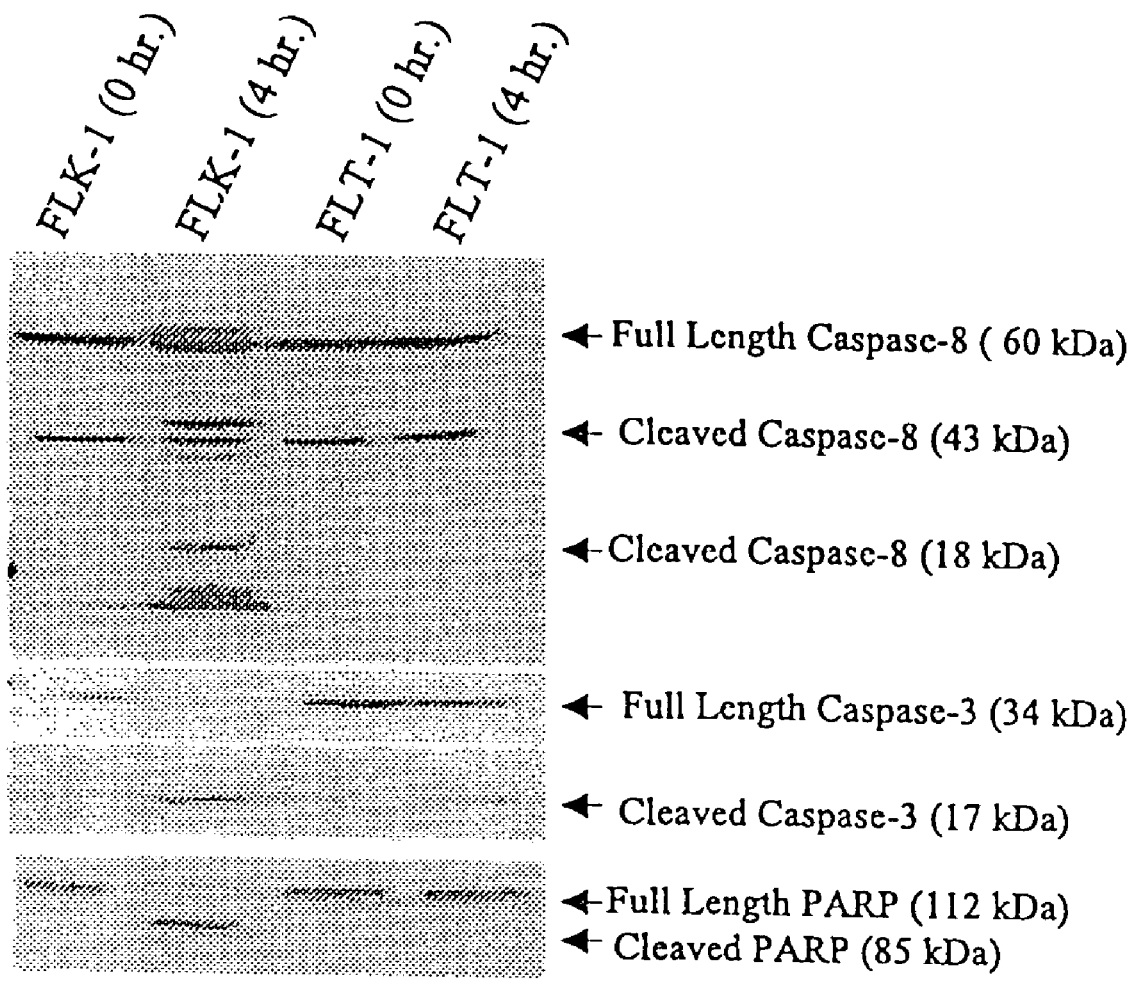
FIG. 44 shows cleavage and activation of caspase-3, caspase-8, and PARP in PAE/FLK-1 cells treated with GrB/VEGF$_{121}$. PAE cells were plated into six-well plates at a density of 2×10$^5$ cells/well and treated with 20 nM GrB/VEGF$_{121}$ for 4 h. The total cell lysates were loaded onto 12% SDS-PAGE and Western blot was performed using appropriate primary antibodies.

PAE cells were treated with GrB/VEGF$_{121}$, total cell lysates were loaded onto 12% SDS-PAGE, and standard Western blotting was performed. The results showed that treatment with GrB/VEGF$_{121}$ cleaved caspase-8, caspase-3, and PARP in PAE/FLK-1 cells but not in PAE/FLT-1 cells (FIG. 44). These data indicate that the GrB/VEGF$_{121}$ construct activated caspases involved in the apoptosis pathway.

EXAMPLE 37

Microarray Analysis of Human Umbilical Vein Endothelial Cells (HUVECs) Treated with VEGF$_{121}$/rGel To further elucidate the biochemical mechanisms that govern the effects of VEGF$_{121}$/rGel on endothelial cells, HUVECs were treated with saline or the IC$_{50}$ dose of VEGF$_{121}$/rGel for 24 h. RNA was then isolated, evaluated for integrity, and subjected to microarray analysis HUVEC RNA was amplified using protocol previously described. Test and control samples (HUVECs treated for 24 h with VEGF$_{121}$/rGel or saline, respectively) were labeled using Cy3- and Cy5-dCTP in reverse transcription reaction. Duplicate experiments were conducted by dye swapping. The labeled samples were hybridized to a cDNA array of 2304 sequence-verified clones in duplicate printed by the Cancer Genomics Core Laboratory of the Department of Pathology at M. D. Anderson Cancer Center. The array included 4800 genes involved in signal transduction, stress response, cell cycle control, hypoxia, and metastatic spread. Hybridization was performed overnight at 60° C. in a humid incubator. After washing, the hybridized slides were scanned using a GEN-ETAC LS IV laser scanner (Genomic Solutions, Ann Arbor, Mich.) and signal intensities were quantified with ARRAYVISION (Imaging Research Inc., St. Catherines, Ontario, Canada). Local background-subtracted spot intensities were used for further analysis. Differentially expressed genes were identified on the basis of a cutoff value of T value. Generally, a cutoff value of |3| is considered statistically significant.

Dye swapping experiments were designed to limit dye bias that raises concern in microarray experiments. The two factors addressed by this design are the differences in dye incorporation and gene-specific effects of the dye. Normalization of the data typically corrects for differences in incorporation of dye that affects all the genes. Dye-specific effects can be insignificant compared with other sources of variation in the experiment. Hence, the dye swapping experiments were treated as duplicates. The signal-to-noise ratio of the images was evaluated to determine the quality of the array. Only those spots with a signal-to-noise ratio of ≧2 were evaluated (80%). Genes that showed values greater than |2| in at least 3 of 4 arrays were identified, and the average fold change was determined.

On this basis, 22 genes (out of the 4800 in the microarray) were upregulated by VEGF$_{121}$/rGel at 24 h (Table 4). In addition to upregulating select genes known to be induced by VEGF alone, treatment with VEGF$_{121}$/rGel upregulated genes involved in inflammation, chemotaxis and transcription regulation.

Microarray data were verified by performing RT-PCR analysis on genes that showed the highest level of induction, namely E-selectin (SELE), cytokine A2 (SCYA2, MCP-1), tumor necrosis factor alpha induced protein 3 (TNFAIP3) and NF-kB inhibitor alpha (NF-kBla). Primers were designed on the basis of the accession numbers from the microarray and confirmation of homology using BLAST (NCBI). Induction of E-selectin in PAE/KDR cells was also verified by RT-PCR. GAPDH primers were used as controls. The primers used were as follows: SELE forward—5'GGTTTGGTGAGGT-GTGCTC (SEQ ID NO:16); SELE reverse—5'TGATCTTTCCCGGAACTGC (SEQ ID NO:17); SCYA2 forward—5' TCTGTGCCTGCTGCTCATAG (SEQ ID NO:18); SCYA2 reverse—5' TGGAATCCTGAAC-CCACTTC (SEQ ID NO:19); TNFAIP3 forward—5'ATG-CACCGATACACACTGGA (SEQ ID NO:20); TNFAIP3 reverse—5' CGCCTTCCTCAGTACCAAGT (SEQ ID NO:21); NF-kBla forward—5' AACCTGCAGCAGACTC-CACT (SEQ ID NO:22); NF-kBla reverse—5'GACACGT-GTGGCCATTGTAG (SEQ ID NO:23); porcine E-selectin (PORESEL) forward—5'GCCAACGTGTAAAGCTGTGA (SEQ ID NO:24); PORESEL reverse—5' TCCTCACAGCT-GAAGGCACA (SEQ ID NO:25); GAPDH forward—5' GTCTTCACCACCATGGAG (SEQ ID NO:26); and GAPDH reverse—5'CCACCCTGTTGCTGTAGC (SEQ ID NO:27). Isolated RNA was subjected to first-strand cDNA synthesis as described by the manufacturer of the Superscript First Strand synthesis system (Invitrogen, Carlsbad, Calif.). RT-PCR was performed using a Minicycler PCR machine (MJ Research, Inc., San Francisco, Calif.).

When normalized for GAPDH, transcripts for E-selectin (SELE), cytokine A2 (SCYA2, MCP-1), tumor necrosis factor alpha induced protein 3 (TNFAIP3) and NF-kB inhibitor alpha (NF-kBla) were all increased after treatment with VEGF$_{121}$/rGel, thus validating the results observed in the original microarray (FIG. 45). However, the induction of E-selectin protein levels did not match the induction of mRNA (FIG. 45).

Because PAE/KDR cells have been used as in vitro models for endothelial cells in tumor neovasculature, the effect of VEGF$_{121}$/rGel on gene induction and protein expression in these cells was investigated. PAE/KDR cells were treated with saline or the IC$_{50}$ dose of VEGF$_{121}$/rGel for up to 48 h. As shown in FIG. 46A, PCR analysis for E-selectin confirmed the increase in message within 2 h after treatment with VEGF$_{121}$/rGel. In addition, western blot analysis demonstrated a slight increase in E-selectin protein expression, although the increase in cellular protein levels was slight compared with the observed increase in message (FIG. 46B). Western blots using anti-MKP-1 and anti-ERK2 antibodies also showed no change in protein expression (data not shown).

The results suggest that treatment of HUVECs with VEGF$_{121}$/rGel increases RNA levels of several genes that are involved in inflammation, chemotaxis, intermediary metabolism, and apoptotic pathways (Table I). A previous report showed that only two of these genes, MKP-1 and CXCR4, were upregulated after treatment with VEGF$_{165}$ for 24 h. Therefore, for most of the genes found to be upregulated in the present study, the upregulation appears to be attributable to the VEGF$_{121}$/rGel construct and not the VEGF component itself. This microarray analysis was the first performed on cells treated with a plant-derived protein toxin such as gelonin.

Of all the molecules we studied, the highest level of mRNA induced was that of the cell adhesion molecule E-selectin. In previous studies, treatment with VEGF induced adhesion molecules (E-selectin, VCAM-1, and ICAM-1) in HUVECs via an NF kB-mediated process. E-selectin has been shown to be upregulated after VEGF treatment or in response to inflammation and plays an important role in both tube formation and angiogenesis. Previous studies have shown that E-selectin also plays a major role in the adhesion of epithelial cancer cells to the endothelium and that the ability of cancer cell clones to bind E-selectin on endothelial cells is directly proportional to their metastatic potential. Moreover, drugs that inhibit the expression of E-selectin, such as cimetidine, block the adhesion of tumor cells to the endothelium and prevent metastasis.

However, E-selectin does not necessarily have a role in the adhesion of all cancer cells, nor do all cancer cells require expression of the same endothelial adhesive molecule. The present study shows that $VEGF_{121}$/rGel is a member of a class of molecules that can prevent E-selectin-mediated metastasis because protein levels barely doubled in both PAE/KDR and HUVECs after treatment with $VEGF_{121}$/rGel. A similar pattern of induction of RNA but not protein levels was observed with other genes as well. For example, although MKP-1 RNA levels were induced in HUVECs after treatment with $VEGF_{121}$/rGel, western blots of PAE/KDR and HUVEC whole cell extract did not show a corresponding increase in protein levels (data not shown). In addition, levels of ERK2, which was previously shown to be upregulated by MKP-1 in HUVECs after endothelial cell injury, did not show a change up to 48 h after $VEGF_{121}$/rGel treatment. Taken together, we conclude $VEGF_{121}$/rGel induces an increase in mRNA levels of genes that are important in cell adhesion, migration, and spread but generally does not induce a concomitant increase in protein expression. Since the rGel component of the fusion construct operates by inhibiting protein synthesis, $VEGF_{121}$/rGel could inhibit synthesis of critical proteins that are important for suppression of these specific genes.

This data also suggest that in addition to exerting a cytotoxic effect, $VEGF_{121}$/rGel may act through cellular mechanisms involved in inflammation and stress. Previous studies have showed that several genes are induced as a result of cellular inflammation. For example, early growth response factor 1 (EGR1), SCYA2, E-selectin and VCAM-1 are all up-regulated in HUVECs, and all of these genes are induced by treatment with $VEGF_{121}$/rGel. In addition, several members of the small inducible cytokine (SCYA) family of proteins are overexpressed after $VEGF_{121}$/rGel treatment. All of these SCYA proteins respond to inflammation stimuli and play a role in chemotaxis: SCYA2 plays a role in inflammation and wound healing; SCYA4 (MIP-1b) is involved in directional migration of cells during normal and inflammatory processes; and SCYA7 (MCP-3) and SCYA11 (eotaxin) share 65% amino acid sequence identity and play major roles in the recruitment and activation of eosinophils in allergic disorders. Another molecule that plays a role in chemotaxis is CXCR4. Although treatment with $VEGF_{121}$/rGel increases the CXCR4 level to less than twice the level without treatment, array spot intensities and reproducibility data indicate that the increase is significant.

Transcription factors represent one of the larger classes of genes to be upregulated by treatment with $VEGF_{121}$/rGel. Interestingly, two of them, NF-kBla (IkB-a) and NF-kB (p105 subunit), are from the NF-kB family. Since NF-kB and IkB-a interact in an autoregulatory mechanism, the upregulation of IkB-a is most likely due to NF-kB's mediating activation of the IkB-a gene, resulting in replenishment of the cytoplasmic pool of its own inhibitor. NF-kB may play a role in the upregulation of several genes, including SCYA2, SCYA7, SCYAL11, and JunB. Another transcription factor, Kruppel-like factor (KLF4), has not been shown to be expressed in endothelial cells. However, this molecule is an important nuclear factor in the up-regulation of histidine decarboxylase, an enzyme that catalyzes the conversion of histidine to histamine, a bioamine that plays an important role in allergic responses, inflammation, neurotransmission, and gastric acid secretion.

Among the molecules governing apoptosis, TNFAIP3, a putative DNA binding protein in the NF-kB signal transduction pathway, functions by inhibiting NF-kB activation and TNF-mediated apoptosis. BIRC3, another gene that is upregulated by treatment with $VEGF_{121}$/rGel, forms a heterodimer with a caspase-9 monomer in vitro and prevents the activation of caspase-9 in apoptosis. Surprisingly, several genes involved in the control of the apoptotic pathway were modulated in response to the fusion toxin even though the overall cytotoxic effect on target cells did not include an observable impact on the apoptotic pathway.

A finding of this study is the identification of several genes that are regulated in response to treatment with the $VEGF_{121}$/rGel fusion construct. Since many of these genes regulate cell adhesion, chemotaxis, and inflammatory responses, the construct may influence tumor development in addition to exerting direct cycotoxic effects on the tumor neovasculature. Therefore, important considerations for future study are the effects of $VEGF_{121}$/rGel cytotoxicity on tumor endothelial cells and the potential bystander effects of the construct on adjacent tumor cells.

TABLE 4

Genes Induced by Treatment With $VEGF_{121}$/rGel

| Gene Classification | Accession Number | Gene Symbol | | Mean Fold Change |
|---|---|---|---|---|
| Cell Adhesion | H39560 | SELE | E-selectin (endothelial adhesion molecule 1)[a] | 94.6 |
| | H07071 | VCAM | Vascular cell adhesion molecule 1 | 4.9 |
| | AA284668 | PLAU | Plasminogen activator, urokinase | 2.3 |
| Apoptosis | AA476272 | TNFAIP3 | Tumor necrosis factor a-induced protein 3[a] | 13.5 |
| | H48706 | BIRC3 | Baculoviral IAP repeat-containing 3 | 3.3 |
| Transcription Factor | T99236 | JUNB | Jun B proto-oncogene | 4.9 |
| | W55872 | NF-kBla | a inhibitor of nuclear factor of kappa light chain gene enhancer in B cell[a] | 4.8 |
| | AA451716 | NF-kB1 | Nuclear factor of kappa light chain gene enhancer in B cell | 2.3 |
| | H45711 | KLF4 | Kruppel-like factor 4 | 2.3 |
| Chemotaxis | AA425102 | SCYA2 | Small inducible cytokine A2 (MCP-1)[a] | 20.2 |
| | H62985 | SCYA4 | Small inducible cytokine A4 (MIP-1b) | 5.8 |
| | AA040170 | SCYA7 | Small inducible cytokine A7 (MCP-3) | 5.5 |
| | T62491 | CXCR4 | Chemokine (C-X-C motif) receptor 4 (fusin) | 1.85 |
| Structural Organization | NM004856 | KNSL5 | Kinesin-like 5 (mitotic kinesin-like protein 1) | 6.4 |
| | AA479199 | NID2 | Nidogen 2 | 3.1 |
| | AA453105 | H2AFL | H2A histone family, member L | 2.5 |
| Inflammation | W69211 | SCYA11 | Small inducible cytokine A11 (Cys-Cys) (eotaxin) | 8.4 |
| | NM001964 | EGR1 | Early growth response 1 | 3.9 |

TABLE 4-continued

Genes Induced by Treatment With VEGF$_{121}$/rGel

| Gene Classification | Accession Number | Gene Symbol | | Mean Fold Change |
|---|---|---|---|---|
| | NM000963 | PTGS2 | Prostaglandin-endoperoxide synthase 2 (COX-2) | 3.3 |
| | AA148736 | SCD4 | Syndecan 4 (amphiglycan, ryudocan) | 3.2 |
| Signalling | W65461 | DUSP5 | Dual specificity phosphatase 5 (MKP-1) | 2.7 |
| Metabolic | AA011215 | SAT | Spermidine/spermine N1-acetyltransferase | 2.1 |

[a] confirmed by RT-PCR at 4 and 24 h post-treatment

EXAMPLE 38

VEGF$_{121}$/rGel Inhibits Tube Formation in KDR-Expressing Endothelial Cells

This example investigates the anti-angiogenic effect of VEGF$_{121}$/rGel in vitro by examining the inhibition of tube formation in receptor-transfected PAE cells.

PAE/KDR and PAE/Flt-1 cells were grown to 80% confluence, detached using Versene, and plated at a concentration of 2×10$^4$ cells per well in a 96-well Matrigel-coated plate under reduced serum (2% FBS) conditions. Cells were treated with 100 nM, 10 nM, 1 nM, 0.1 nM, or 0.01 nM VEGF$_{121}$/rGel or rGel in triplicate for 24 h. Inhibition of tube formation was assessed by counting the number of tubes formed per well under bright field microscopy. The ability of VEGF$_{121}$/rGel to inhibit tube formation as a function of incubation time before plating on Matrigel was studied by incubating PAE/KDR cells at the IC$_{50}$ dose (1 nM) for different periods up to 24 h. Cells were detached and plated in 96-well Matrigel-coated plates under the conditions described above.

As shown in FIG. 47A, the addition of 1 nM VEGF$_{121}$/rGel significantly inhibited tube formation in KDR-transfected cells, whereas rGel alone had little effect at this dose level. Doses of rGel alone caused ~42% inhibition at only the highest concentration tested (100 nM). Endothelial cells expressing VEGFR-1 (PAE/Flt-1) were not as sensitive to VEGF$_{121}$/rGel as were the PAE/KDR cells, requiring 100 nM VEGF$_{121}$/rGel or rGel to inhibit tube formation by 50% (FIG. 47B).

Figure 48:
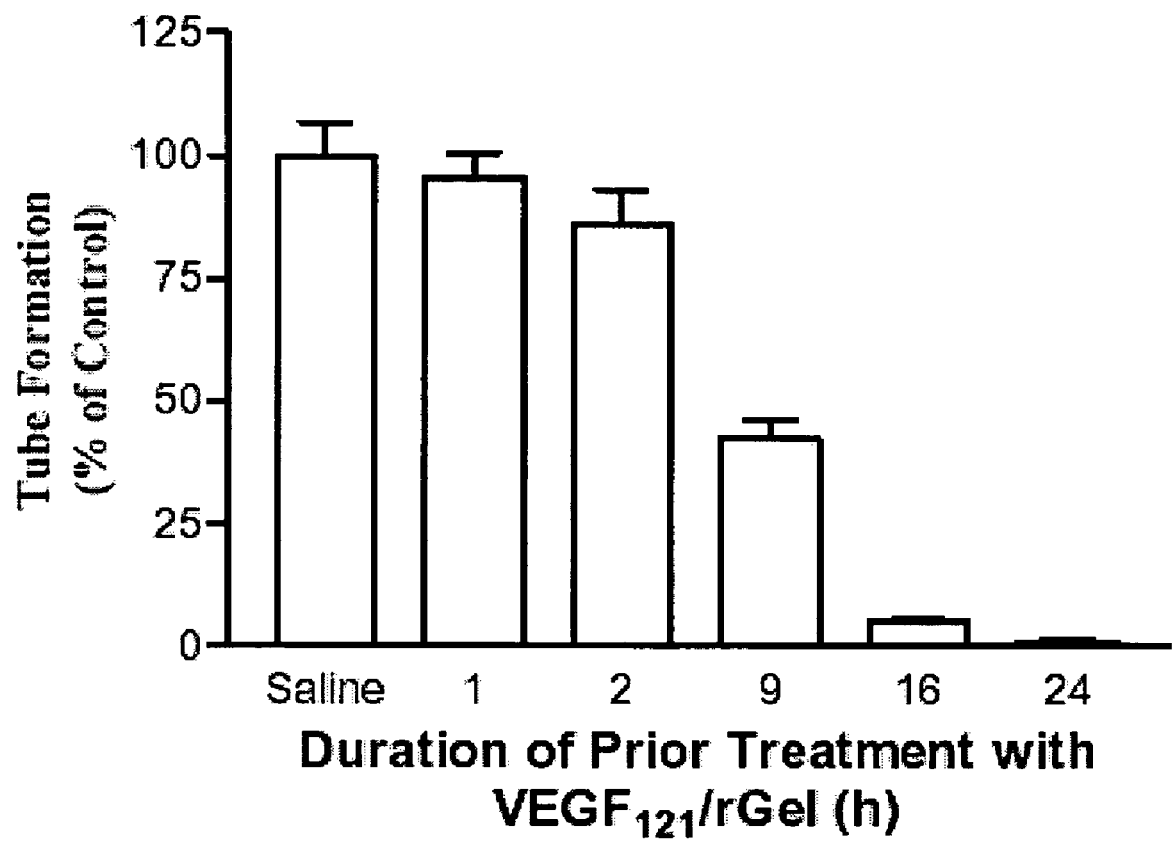
FIG. 48 shows time-dependent inhibition of tube formation of PAE/KDR cells by VEGF$_{121}$/rGel. PAE/KDR cells were treated with 1 nM VEGF$_{121}$/rGel for the periods indicated, detached, incubated on Matrigel-coated plates for 24 h, and assessed for tube formation. Incubation of PAE/KDR cells with VEGF$_{121}$/rGel for as little as 9 h was sufficient to abolish the ability of these cells to form tubes by 50%.

To determine whether pre-treatment of PAE/KDR cells with VEGF$_{121}$/rGel affects tube formation, cells were treated with the IC$_{50}$ dose of VEGF$_{121}$/rGel for 4, 16, and 24 h, washed with PBS, detached, added to Matrigel-coated plates in VEGF$_{121}$/rGel-free medium, and incubated for an additional 24 h. Prior incubation of cells with VEGF$_{121}$/rGel for 16 or 24 h virtually abolished tube formation (FIG. 48).

The effect of VEGF$_{121}$/rGel on tube formation of endothelial cells on Matrigel-coated plates was striking in that cells overexpressing the KDR receptor, but not cells overexpressing the Flt-1 receptor, were affected. This result is consistent with the findings that VEGF$_{121}$/rGel is cytotoxic only to KDR-expressing endothelial cells and that VEGF$_{121}$/rGel is internalized only into endothelial cells that express KDR but not Flt-1. The fact that the IC$_{50}$ dose for cytotoxicity is identical to the IC$_{50}$ dose for preventing tube formation in PAE/KDR cells suggests that VEGF$_{121}$/rGel action in vitro immediately disrupts angiogenic tube formation as a temporal prelude to its eventual cytotoxicity to rapidly dividing endothelial cells. Preliminary results examining in vivo endothelialization of Matrigel plugs appear to support the observation that VEGF$_{121}$/rGel construct can ablate neovascularization at several steps in this complex process.

EXAMPLE 39

VEGF$_{121}$/rGel Inhibits Angiogenesis in the Chorioallantoic Membranes of Chicken Embryos This example investigates the antiangiogenic effects of VEGF$_{121}$/rGel in vivo using a chicken chorioallantoic membranes model. Fertilized chicken eggs (SPAFAS; Charles River Laboratories, Wilmington, Mass.) were incubated at 37° C. at 55% humidity for 9 days. An artificial air sac was created over a region containing small blood vessels in the chorioallantoic membranes as previously described (Brooks et al., 1999). A small "window" was cut in the shell after removal of 3 ml of albumen. Filter disks measuring 6 mm in diameter were coated with cortisone acetate in absolute ethanol (3 mg/ml). Each chorioallantoic membranes was locally treated with filter disks saturated with a solution containing bFGF (50 ng/disk) and VEGF$_{121}$/rGel (1 or 10 nM), rGel (1 or 10 nM), or buffer (PBS). The filter was placed on the chorioallantoic membranes in a region with the lowest density of blood vessels and, as a reference, in the vicinity of a large vessel. Angiogenesis was documented photographically 3 days after treatment. Images were captured using an Olympus stereomicroscope (SZ x12) and Spot Basic software (Diagnostic Instruments, Inc.). The relative vascular density was determined by measuring the area taken up by blood vessels in treated chorioallantoic membranes, normalized to that in chorioallantoic membranes treated with PBS (equal to 100%) (Jiang et al., 2000). This analysis was performed on a Macintosh computer using the public domain NIH Image program. The numbers of blood vessel branch points were quantified by two researchers and compared with the numbers in the treatment controls (Brooks et al., 1999).

Figure 49A:
FIGS. 49A-C show VEGF$_{121}$/rGel-mediated inhibition of angiogenesis in chicken embryo chorioallantoic membranes. Angiogenesis was induced on chorioallantoic membranes from 9-day-old chicken embryos by filter disks saturated with bFGF. Disks were simultaneously treated with VEGF$_{121}$/rGel or rGel. At 72 h, chorioallantoic membranes were harvested and examined using an Olympus stereomicroscope. Experiments were performed twice per treatment, with 6 to 10 embryos per condition in every experiment. Shown are vessels in representative chorioallantoic membranes treated with 50 ng bFGF alone (FIG. 49A), bFGF in combination with 10 nM rGel (×0.5 objective) (FIG. 49B), or bFGF in combination with 1 nM VEGF$_{121}$/rGel (FIG. 49C).
Figure 49B:
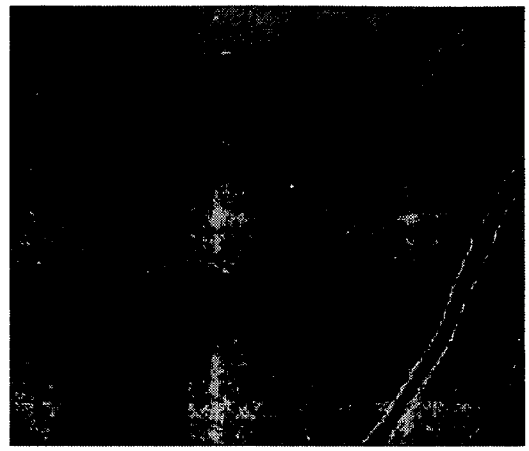
Figure 49C:
Figures 50A, 50B:
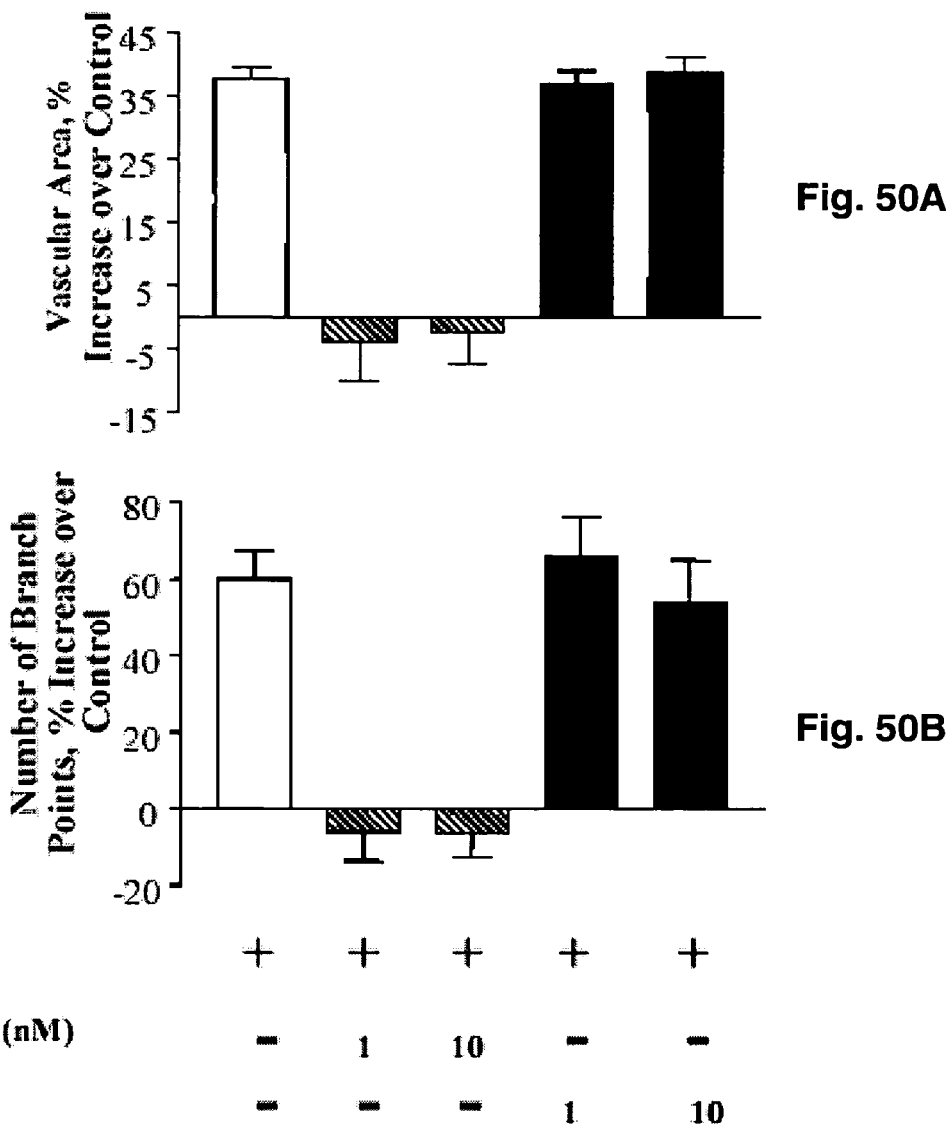
FIGS. 50A-B show VEGF$_{121}$/rGel-mediated reduction of vascular area and number of vascular branches in the chorioallantoic membranes assay. Quantitative evaluation of VEGF$_{121}$/rGel-mediated inhibition of angiogenesis in the chorioallantoic membranes model was determined after the indicated treatments by image analyses, and the results were normalized to chorioallantoic membranes treated with buffer (PBS; equal to 100%). VEGF$_{121}$/rGel at both 1 and 10 nM decreased the vascular area (FIG. 50A). As expected, rGel alone had no effect. Data represent the means±standard deviations from replicated experiments. *, P<0.001; t-test, double-sided.

As shown in FIGS. 49A and 50A, vascularized area was about 35% higher in the chorioallantoic membranes treated with bFGF than in those treated with PBS, and the difference was significant (P<0.001; t-test, double-sided). This observation was consistent with the finding of more than a 60% increase in the number of newly sprouted vessels in the bFGF-treated chorioallantoic membranes compared to the PBS-treated chorioallantoic membranes (P<0.001; t-test, double-sided; FIG. 50B). Incubation of chorioallantoic membranes with bFGF without or with 10 nM rGel resulted in angiogenic activity and formation of an ordered neovasculature (FIGS. 49A and 49B). In contrast, treatment with 1 or 10 nM VEGF$_{121}$/rGel resulted in considerable destruction of the neovasculature (FIG. 49C). Treatment with VEGF$_{121}$/rGel also completely inhibited bFGF-stimulated angiogenesis (P<0.001; t-test, double sided; FIG. 50). Many of the treated chorioallantoic membranes also appeared to be devoid of vessel infiltration. Interestingly, the number of branching points in the VEGF$_{121}$/rGel-treated chorioallantoic membranes was similar to that in the PBS-treated chorioallantoic membranes (P>0.5; t-test, double-sided; FIG. 50B), suggesting that VEGF$_{121}$/rGel mainly inhibits bFGF-mediated formation of newly sprouting branches from preexisiting vessels. As expected, the disks treated with bFGF in combination with rGel (at 1 or 10 nM) consistently showed extensive vascularization that was comparable to that found in those treated with bFGF alone (P>0.5; t-test, double-sided). This critical finding suggests that VEGF$_{121}$/rGel does not affect mature vessels in either normal tissues or tumors. Therefore, small, newly vascularizing tumors and metastases may be the lesions most responsive to therapy with this agent.

The following references were cited herein:

Binetruy-Tournaire et al., *EMBO* 19:1525-33 (2000).
Brekken, et al., *Cancer Res.* 58:1952-1959 (1998).
Brooks et al., *Methods Mol. Biol.* 129:257-269 (1999).
Honkoop et al., *Br. J. Cancer* 77:621-26 (1998).
Jiang et al., *Proc. Nat. Acad. Sci. U.S.A.* 97:1749-1753 (2000).
Leenders et al., *Lab. Invest.* 82:473-81 (2002).
Lu et al., *J. Biol. Chem.* 278:43496-507 (2003).
Murata et al., *Int. J. Radiat. Oncol. Biol. Phys.* 51:1018-24 (2001).
Pedley et al., *Int. J. Radiat. Oncol. Biol. Phys.* 54:1524-31 (2002).
Siemann et al., *Int. J. Cancer* 99:1-6 (2002).
Vartanian and Weidner, *Am. J. Pathol.* 144:1188-94 (1994).
Veenendaal et al., *Proc Natl Acad Sci U.S.A.* 99:7866-71 (2002).
Wu et al., *Zhonghua Zhong Liu Za Zhi* 24:540-543 (2002).

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. A method of inhibiting the differentiation of an osteoclast precursor cell into a mature osteoclast, comprising contacting said osteoclast precursor cell with a biologically effective amount of a conjugate comprising a cytotoxic polypeptide and a VEGF polypeptide that binds to both vascular endothelial growth factor (VEGF) receptor type 1 (Flt-1) and VEGF receptor type 2 (kinase domain receptor/Flk-1), wherein differentiation of the osteoclast precursor cell is inhibited.

2. The method of claim 1, wherein said conjugate is a fusion protein of said VEGF polypeptide and said cytotoxic polypeptide.

3. The method of claim 1, wherein said VEGF polypeptide comprises an amino acid sequence selected from the group consisting of SEQ ID NOs:28-34.

4. The method of claim 1, wherein said cytotoxic polypeptide is a toxin or a signal transduction protein capable of generating apoptotic signals.

5. The method of claim 4, wherein said toxin is gelonin.

6. The method of claim 4, wherein said signal transduction protein capable of generating apoptotic signals is selected from the group consisting of granzyme B, Bax, TNF-a, TNF-b, TNF-like molecule, TGF-b, IL-12, IL-3, IL-24, IL-18, TRAIL, IFN-a, IFN-b, IFN-g, Bcl-2, Fas ligand and caspases.

7. The method of claim 1, wherein said conjugate is a fusion protein comprising the 121-amino acid isoform of vascular endothelial growth factor (VEGF$_{121}$) and gelonin or a fusion protein comprising VEGF$_{121}$ and granzyme B.

8. The method of claim 1, wherein the osteoclast precursor cell is in a subject.

9. The method of claim 8, wherein said subject suffers from osteoporosis or osteoarthritis.

10. The method of claim 8, wherein said subject suffers from osteolytic lesions or bone lysis.

11. The method of claim 8, wherein said subject suffers from skeletal metastases.

12. The method of claim 8, wherein the biologically effective amount of the conjugate is administered to the subject.

* * * * *

UNITED STATES PATENT AND TRADEMARK OFFICE
CERTIFICATE OF CORRECTION

PATENT NO.       : 7,601,341 B2
APPLICATION NO. : 10/919193
DATED            : October 13, 2009
INVENTOR(S)      : Michael Rosenblum It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 900 days.

Signed and Sealed this

Fifth Day of October, 2010

David J. Kappos
*Director of the United States Patent and Trademark Office*

SEQUENCE LISTING

```
<160> NUMBER OF SEQ ID NOS: 35

<210> SEQ ID NO 1
<211> LENGTH: 33
<212> TYPE: DNA
<213> ORGANISM: Artificial Sequence
<220> FEATURE:
<221> NAME/KEY: primer_bind
<223> OTHER INFORMATION: primer VEGF Nterm

<400> SEQUENCE: 1
tggtcccagg ctcatatggc acccatggca gaa                            33

<210> SEQ ID NO 2
<211> LENGTH: 38
<212> TYPE: DNA
<213> ORGANISM: Artificial Sequence
<220> FEATURE:
<221> NAME/KEY: primer_bind
<223> OTHER INFORMATION: primer VEGF Cterm

<400> SEQUENCE: 2
tctagaccgg agccaccgcc accccgcctc ggcttgtc                       38

<210> SEQ ID NO 3
<211> LENGTH: 33
<212> TYPE: DNA
<213> ORGANISM: Artificial Sequence
<220> FEATURE:
<221> NAME/KEY: primer_bind
<223> OTHER INFORMATION: primer Gel Nterm

<400> SEQUENCE: 3
ggtggcggtg gctccggtct agacaccgtg agc                            33

<210> SEQ ID NO 4
<211> LENGTH: 45
<212> TYPE: DNA
<213> ORGANISM: Artificial Sequence
<220> FEATURE:
<221> NAME/KEY: primer_bind
<223> OTHER INFORMATION: primer Gel Cterm

<400> SEQUENCE: 4
```
aaggctcgtg tcgacctcga gtcattaagc tttaggatct ttatc  45

<210> SEQ ID NO 5
<211> LENGTH: 36
<212> TYPE: DNA
<213> ORGANISM: Artificial Sequence
<220> FEATURE:
<221> NAME/KEY: primer_bind
<223> OTHER INFORMATION: primer NcoIgb

<400> SEQUENCE: 5
ggtggcggtg gctccatgga accaatcctg cttctg  36

<210> SEQ ID NO 6
<211> LENGTH: 39
<212> TYPE: DNA
<213> ORGANISM: Artificial Sequence
<220> FEATURE:
<221> NAME/KEY: primer_bind
<223> OTHER INFORMATION: primer CxhoIgb

<400> SEQUENCE: 6
gccaccgcct ccctcgagct attagtagcg tttcatggt  39

<210> SEQ ID NO 7
<211> LENGTH: 5
<212> TYPE: PRT
<213> ORGANISM: Artificial Sequence
<220> FEATURE:
<221> NAME/KEY: DOMAIN
<223> OTHER INFORMATION: a cleavage site for EK

<400> SEQUENCE: 7

Asp Asp Asp Asp Lys
              5

<210> SEQ ID NO 8
<211> LENGTH: 39
<212> TYPE: DNA
<213> ORGANISM: Artificial Sequence
<220> FEATURE:
<221> NAME/KEY: primer_bind
<223> OTHER INFORMATION: primer NgbEK

<400> SEQUENCE: 8
ggtaccgacg acgacgacaa gatcatcggg ggacatgag  39

<210> SEQ ID NO 9
<211> LENGTH: 30
<212> TYPE: DNA
<213> ORGANISM: Artificial Sequence
<220> FEATURE:
<221> NAME/KEY: primer_bind
<223> OTHER INFORMATION: primer Cgb

<400> SEQUENCE: 9
ggagccaccg ccaccgtagc gtttcatggt  30

<210> SEQ ID NO 10
<211> LENGTH: 30
<212> TYPE: DNA
<213> ORGANISM: Artificial Sequence
<220> FEATURE:
<221> NAME/KEY: primer_bind
<223> OTHER INFORMATION: primer Nvegf

<400> SEQUENCE: 10
ggtggcggtg gctccgcacc catggcagaa                             30

<210> SEQ ID NO 11
<211> LENGTH: 42
<212> TYPE: DNA
<213> ORGANISM: Artificial Sequence
<220> FEATURE:
<221> NAME/KEY: primer_bind
<223> OTHER INFORMATION: primer CxhoI veg

<400> SEQUENCE: 11
aaggctcgtg tcgacctcga gtcattaccg cctcggcttg tc               42

<210> SEQ ID NO 12
<211> LENGTH: 18
<212> TYPE: DNA
<213> ORGANISM: Artificial Sequence
<220> FEATURE:
<221> NAME/KEY: primer_bind
<223> OTHER INFORMATION: primer T7 promoter

<400> SEQUENCE: 12
taatacgact cactatag                                          18

<210> SEQ ID NO 13
<211> LENGTH: 30
<212> TYPE: DNA
<213> ORGANISM: Artificial Sequence
<220> FEATURE:
<221> NAME/KEY: primer_bind
<223> OTHER INFORMATION: primer CpET32EK

<400> SEQUENCE: 13
cttgtcgtcg tcgtcggtac ccagatctgg                             30

<210> SEQ ID NO 14
<211> LENGTH: 744
<212> TYPE: DNA
<213> ORGANISM: Homo sapiens
<220> FEATURE:
<221> NAME/KEY: gene
<223> OTHER INFORMATION: human granzyme B with signal peptide sequence

<400> SEQUENCE: 14
atgcaaccaa tcctgcttct gctggccttc ctcctgctgc ccagggcaga       50 tgcagggag atcatcgggg acatgaggc caagccccac tcccgcccct        100
acatggctta tcttatgatc tgggatcaga agtctctgaa gaggtgcggt      150
ggcttcctga tacaagacga cttcgtgctg acagctgctc actgttgggg      200
aagctccata aatgtcacct gggggccca caatatcaaa gaacaggagc       250
cgacccagca gtttatccct gtgaaaagac ccatccccca tccagcctat      300
aatcctaaga acttctccaa cgacatcatg ctactgcagc tggagagaaa      350
ggccaagcgg accagagctg tgcagcccct caggctacct agcaacaagg      400
cccaggtgaa gccagggcag acatgcagtg tggccggctg ggggcagacg      450 gccccctgg aaaacactc acacacacta aagagggtga agatgacagt        500
gcaggaagat cgaaagtgcg aatctgactt acgccattat tacgacagta      550
ccattgagtt gtgcgtgggg gacccagaga ttaaaagac ttccttaag        600 ggggactctg gaggccctct tgtgtgtaac aaggtggccc agggcattgt      650
ctcctatgga cgaaacaatg gcatgcctcc acgagcctgc accaaagtct      700
caagctttgt acactggata aagaaaacca tgaaacgcta ctaa         744

<210> SEQ ID NO 15
<211> LENGTH: 247
<212> TYPE: PRT
<213> ORGANISM: Homo sapiens
<220> FEATURE:
<221> NAME/KEY: PROPEP
<223> OTHER INFORMATION: human granzyme B with signal peptide sequence

<400> SEQUENCE: 15

Met Gln Pro Ile Leu Leu Leu Ala Phe Leu Leu Leu Pro Arg
                 5                  10                  15

Ala Gly Ala Gly Glu Ile Ile Gly Gly His Glu Ala Lys Pro His
                20                  25                  30

Ser Arg Pro Tyr Met Ala Tyr Leu Met Ile Trp Asp Gln Lys Ser
                35                  40                  45

Leu Lys Arg Cys Gly Gly Phe Leu Ile Gln Asp Asp Phe Val Leu
                50                  55                  60

Thr Ala Ala His Cys Trp Gly Ser Ser Ile Asn Val Thr Leu Gly
                65                  70                  75

Ala His Asn Ile Lys Glu Gln Glu Pro Thr Gln Gln Phe Ile Pro
                80                  85                  90

Val Lys Arg Pro Ile Pro His Pro Ala Tyr Asn Pro Lys Asn Phe
                95                 100                 105

Ser Asn Asp Ile Met Leu Leu Gln Leu Glu Arg Lys Ala Lys Arg
               110                 115                 120

Thr Arg Ala Val Gln Pro Leu Arg Leu Pro Ser Asn Lys Ala Gln
               125                 130                 135

Val Lys Pro Gly Gln Thr Cys Ser Val Ala Gly Trp Gly Gln Thr
               140                 145                 150

Ala Pro Leu Gly Lys His Ser His Thr Leu Gln Glu Val Lys Met
               155                 160                 165

Thr Val Gln Glu Asp Arg Lys Cys Glu Ser Asp Leu Arg His Tyr
               170                 175                 180

Tyr Asp Ser Thr Ile Glu Leu Cys Val Gly Asp Pro Glu Ile Lys
               185                 190                 195

Lys Thr Ser Phe Lys Gly Asp Ser Gly Gly Pro Leu Val Cys Asn
               200                 205                 210

Lys Val Ala Gln Gly Ile Val Ser Tyr Gly Arg Asn Asn Gly Met
               215                 220                 225

Pro Pro Arg Ala Cys Thr Lys Val Ser Ser Phe Val His Trp Ile
               230                 235                 240

Lys Lys Thr Met Lys Arg Tyr
               245

<210> SEQ ID NO 16
<211> LENGTH: 19
<212> TYPE: DNA
<213> ORGANISM: Artificial Sequence
<220> FEATURE:
<221> NAME/KEY: primer_bind
<223> OTHER INFORMATION: E-selectin forward primer

<400> SEQUENCE: 16
ggtttggtga ggtgtgctc         19

<210> SEQ ID NO 17
<211> LENGTH: 19
<212> TYPE: DNA
<213> ORGANISM: Artificial Sequence
<220> FEATURE:
<221> NAME/KEY: primer_bind
<223> OTHER INFORMATION: E-selectin reverse primer

<400> SEQUENCE: 17
tgatctttcc cggaactgc                                                19

<210> SEQ ID NO 18
<211> LENGTH: 20
<212> TYPE: DNA
<213> ORGANISM: Artificial Sequence
<220> FEATURE:
<221> NAME/KEY: primer_bind
<223> OTHER INFORMATION: cytokine A2 (SCYA2, MCP-1) forward primer

<400> SEQUENCE: 18
tctgtgcctg ctgctcatag                                               20

<210> SEQ ID NO 19
<211> LENGTH: 20
<212> TYPE: DNA
<213> ORGANISM: Artificial Sequence
<220> FEATURE:
<221> NAME/KEY: primer_bind
<223> OTHER INFORMATION: cytokine A2 (SCYA2, MCP-1) reverse primer

<400> SEQUENCE: 19
tggaatcctg aacccacttc                                               20

<210> SEQ ID NO 20
<211> LENGTH: 20
<212> TYPE: DNA
<213> ORGANISM: Artificial Sequence
<220> FEATURE:
<221> NAME/KEY: primer_bind
<223> OTHER INFORMATION: tumor necrosis factor alpha induced protein 3
      (TNFAIP3) forward primer

<400> SEQUENCE: 20
atgcaccgat acacactgga                                               20

<210> SEQ ID NO 21
<211> LENGTH: 20
<212> TYPE: DNA
<213> ORGANISM: Artificial Sequence
<220> FEATURE:
<221> NAME/KEY: primer_bind
<223> OTHER INFORMATION: tumor necrosis factor alpha induced protein 3
      (TNFAIP3) reverse primer

<400> SEQUENCE: 21
cgccttcctc agtaccaagt                                               20

<210> SEQ ID NO 22
<211> LENGTH: 20
<212> TYPE: DNA
<213> ORGANISM: Artificial Sequence
<220> FEATURE:
<221> NAME/KEY: primer_bind
<223> OTHER INFORMATION: NF-_B inhibitor alpha (NF-_BI_) forward primer

<400> SEQUENCE: 22
aacctgcagc agactccact                                               20

-continued

```
<210> SEQ ID NO 23
<211> LENGTH: 20
<212> TYPE: DNA
<213> ORGANISM: Artificial Sequence
<220> FEATURE:
<221> NAME/KEY: primer_bind
<223> OTHER INFORMATION: NF-_B inhibitor alpha (NF-_BI_) reverse primer

<400> SEQUENCE: 23
gacacgtgtg gccattgtag                                                    20

<210> SEQ ID NO 24
<211> LENGTH: 20
<212> TYPE: DNA
<213> ORGANISM: Artificial Sequence
<220> FEATURE:
<221> NAME/KEY: primer_bind
<223> OTHER INFORMATION: porcine E-selectin forward primer

<400> SEQUENCE: 24
gccaacgtgt aaagctgtga                                                    20

<210> SEQ ID NO 25
<211> LENGTH: 20
<212> TYPE: DNA
<213> ORGANISM: Artificial Sequence
<220> FEATURE:
<221> NAME/KEY: primer_bind
<223> OTHER INFORMATION: porcine E-selectin reverse primer

<400> SEQUENCE: 25
tcctcacagc tgaaggcaca                                                    20

<210> SEQ ID NO 26
<211> LENGTH: 18
<212> TYPE: DNA
<213> ORGANISM: Artificial Sequence
<220> FEATURE:
<221> NAME/KEY: primer_bind
<223> OTHER INFORMATION: GAPDH forward primer

<400> SEQUENCE: 26
gtcttcacca ccatggag                                                      18

<210> SEQ ID NO 27
<211> LENGTH: 18
<212> TYPE: DNA
<213> ORGANISM: Artificial Sequence
<220> FEATURE:
<221> NAME/KEY: primer_bind
<223> OTHER INFORMATION: GAPDH reverse primer

<400> SEQUENCE: 27
ccaccctgtt gctgtagc                                                      18

<210> SEQ ID NO 28
<211> LENGTH: 121
<212> TYPE: PRT
<213> ORGANISM: Artificial Sequence
<220> FEATURE:
<221> NAME/KEY: PEPTIDE
<223> OTHER INFORMATION: VEGF121 isoform

<400> SEQUENCE: 28

Ala Pro Met Ala Glu Gly Gly Gly Gln Asn His His Glu Val Val
              5                  10                  15
```

```
Lys Phe Met Asp Val Tyr Gln Arg Ser Tyr Cys His Pro Ile Glu
                20                  25                  30

Thr Leu Val Asp Ile Phe Gln Glu Tyr Pro Asp Glu Ile Glu Tyr
                35                  40                  45

Ile Phe Lys Pro Ser Cys Val Pro Leu Met Arg Cys Gly Gly Cys
                50                  55                  60

Cys Asn Asp Glu Gly Leu Glu Cys Val Pro Thr Glu Glu Ser Asn
                65                  70                  75

Ile Thr Met Gln Ile Met Arg Ile Lys Pro His Gln Gly Gln His
                80                  85                  90

Ile Gly Glu Met Ser Phe Leu Gln His Asn Lys Cys Glu Cys Arg
                95                 100                 105

Pro Lys Lys Asp Arg Ala Arg Gln Glu Asn Cys Asp Lys Pro Arg
               110                 115                 120

Arg

<210> SEQ ID NO 29
<211> LENGTH: 206
<212> TYPE: PRT
<213> ORGANISM: Artificial Sequence
<220> FEATURE:
<221> NAME/KEY: PEPTIDE
<223> OTHER INFORMATION: VEGF206

<400> SEQUENCE: 29

Ala Pro Met Ala Glu Gly Gly Gly Gln Asn His His Glu Val Val
                 5                  10                  15

Lys Phe Met Asp Val Tyr Gln Arg Ser Tyr Cys His Pro Ile Glu
                20                  25                  30

Thr Leu Val Asp Ile Phe Gln Glu Tyr Pro Asp Glu Ile Glu Tyr
                35                  40                  45

Ile Phe Lys Pro Ser Cys Val Pro Leu Met Arg Cys Gly Gly Cys
                50                  55                  60

Cys Asn Asp Glu Gly Leu Glu Cys Val Pro Thr Glu Glu Ser Asn
                65                  70                  75

Ile Thr Met Gln Ile Met Arg Ile Lys Pro His Gln Gly Gln His
                80                  85                  90

Ile Gly Glu Met Ser Phe Leu Gln His Asn Lys Cys Glu Cys Arg
                95                 100                 105

Pro Lys Lys Asp Arg Ala Arg Gln Glu Lys Lys Ser Val Arg Gly
               110                 115                 120

Lys Gly Lys Gly Gln Lys Arg Lys Arg Lys Lys Ser Arg Tyr Lys
               125                 130                 135

Ser Trp Ser Val Tyr Val Gly Ala Arg Cys Cys Leu Met Pro Trp
               140                 145                 150

Ser Leu Pro Gly Pro His Pro Cys Gly Pro Cys Ser Glu Arg Arg
               155                 160                 165

Lys His Leu Phe Val Gln Asp Pro Gln Thr Cys Lys Cys Ser Cys
               170                 175                 180

Lys Asn Thr Asp Ser Arg Cys Lys Ala Arg Gln Leu Glu Leu Asn
               185                 190                 195

Glu Arg Thr Cys Arg Cys Asp Lys Pro Arg Arg
               200                 205

<210> SEQ ID NO 30
<211> LENGTH: 189
```

```
<212> TYPE: PRT
<213> ORGANISM: Artificial Sequence
<220> FEATURE:
<221> NAME/KEY: PEPTIDE
<223> OTHER INFORMATION: VEGF189 isoform

<400> SEQUENCE: 30

Ala Pro Met Ala Glu Gly Gly Gly Gln Asn His His Glu Val Val
                 5                  10                  15

Lys Phe Met Asp Val Tyr Gln Arg Ser Tyr Cys His Pro Ile Glu
                20                  25                  30

Thr Leu Val Asp Ile Phe Gln Glu Tyr Pro Asp Glu Ile Glu Tyr
                35                  40                  45

Ile Phe Lys Pro Ser Cys Val Pro Leu Met Arg Cys Gly Gly Cys
                50                  55                  60

Cys Asn Asp Glu Gly Leu Glu Cys Val Pro Thr Glu Glu Ser Asn
                65                  70                  75

Ile Thr Met Gln Ile Met Arg Ile Lys Pro His Gln Gly Gln His
                80                  85                  90

Ile Gly Glu Met Ser Phe Leu Gln His Asn Lys Cys Glu Cys Arg
                95                  100                 105

Pro Lys Lys Asp Arg Ala Arg Gln Glu Lys Lys Ser Val Arg Gly
                110                 115                 120

Lys Gly Lys Gly Gln Lys Arg Lys Arg Lys Lys Ser Arg Tyr Lys
                125                 130                 135

Ser Trp Ser Val Pro Cys Gly Pro Cys Ser Glu Arg Arg Lys His
                140                 145                 150

Leu Phe Val Gln Asp Pro Gln Thr Cys Lys Cys Ser Cys Lys Asn
                155                 160                 165

Thr Asp Ser Arg Cys Lys Ala Arg Gln Leu Glu Leu Asn Glu Arg
                170                 175                 180

Thr Cys Arg Cys Asp Lys Pro Arg Arg
                185

<210> SEQ ID NO 31
<211> LENGTH: 183
<212> TYPE: PRT
<213> ORGANISM: Artificial Sequence
<220> FEATURE:
<221> NAME/KEY: PEPTIDE
<223> OTHER INFORMATION: VEGF183 isoform

<400> SEQUENCE: 31

Ala Pro Met Ala Glu Gly Gly Gly Gln Asn His His Glu Val Val
                 5                  10                  15

Lys Phe Met Asp Val Tyr Gln Arg Ser Tyr Cys His Pro Ile Glu
                20                  25                  30

Thr Leu Val Asp Ile Phe Gln Glu Tyr Pro Asp Glu Ile Glu Tyr
                35                  40                  45

Ile Phe Lys Pro Ser Cys Val Pro Leu Met Arg Cys Gly Gly Cys
                50                  55                  60

Cys Asn Asp Glu Gly Leu Glu Cys Val Pro Thr Glu Glu Ser Asn
                65                  70                  75

Ile Thr Met Gln Ile Met Arg Ile Lys Pro His Gln Gly Gln His
                80                  85                  90

Ile Gly Glu Met Ser Phe Leu Gln His Asn Lys Cys Glu Cys Arg
                95                  100                 105
```

-continued

Pro Lys Lys Asp Arg Ala Arg Gln Glu Lys Lys Ser Val Arg Gly
            110                 115                 120

Lys Gly Lys Gly Gln Lys Arg Lys Arg Lys Lys Ser Arg Pro Cys
            125                 130                 135

Gly Pro Cys Ser Glu Arg Arg Lys His Leu Phe Val Gln Asp Pro
            140                 145                 150

Gln Thr Cys Lys Cys Ser Cys Lys Asn Thr Asp Ser Arg Cys Lys
            155                 160                 165

Ala Arg Gln Leu Glu Leu Asn Glu Arg Thr Cys Arg Cys Asp Lys
            170                 175                 180

Pro Arg Arg

<210> SEQ ID NO 32
<211> LENGTH: 165
<212> TYPE: PRT
<213> ORGANISM: Artificial Sequence
<220> FEATURE:
<221> NAME/KEY: PEPTIDE
<223> OTHER INFORMATION: VEGF165 isoform

<400> SEQUENCE: 32

Ala Pro Met Ala Glu Gly Gly Gly Gln Asn His His Glu Val Val
            5                   10                  15

Lys Phe Met Asp Val Tyr Gln Arg Ser Tyr Cys His Pro Ile Glu
            20                  25                  30

Thr Leu Val Asp Ile Phe Gln Glu Tyr Pro Asp Glu Ile Glu Tyr
            35                  40                  45

Ile Phe Lys Pro Ser Cys Val Pro Leu Met Arg Cys Gly Gly Cys
            50                  55                  60

Cys Asn Asp Glu Gly Leu Glu Cys Val Pro Thr Glu Glu Ser Asn
            65                  70                  75

Ile Thr Met Gln Ile Met Arg Ile Lys Pro His Gln Gly Gln His
            80                  85                  90

Ile Gly Glu Met Ser Phe Leu Gln His Asn Lys Cys Glu Cys Arg
            95                  100                 105

Pro Lys Lys Asp Arg Ala Arg Gln Glu Asn Pro Cys Gly Pro Cys
            110                 115                 120

Ser Glu Arg Arg Lys His Leu Phe Val Gln Asp Pro Gln Thr Cys
            125                 130                 135

Lys Cys Ser Cys Lys Asn Thr Asp Ser Arg Cys Lys Ala Arg Gln
            140                 145                 150

Leu Glu Leu Asn Glu Arg Thr Cys Arg Cys Asp Lys Pro Arg Arg
            155                 160                 165

<210> SEQ ID NO 33
<211> LENGTH: 148
<212> TYPE: PRT
<213> ORGANISM: Artificial Sequence
<220> FEATURE:
<221> NAME/KEY: PEPTIDE
<223> OTHER INFORMATION: VEGF148 isoform

<400> SEQUENCE: 33

Ala Pro Met Ala Glu Gly Gly Gly Gln Asn His His Glu Val Val
            5                   10                  15

Lys Phe Met Asp Val Tyr Gln Arg Ser Tyr Cys His Pro Ile Glu
            20                  25                  30

Thr Leu Val Asp Ile Phe Gln Glu Tyr Pro Asp Glu Ile Glu Tyr

```
                35                  40                  45

Ile Phe Lys Pro Ser Cys Val Pro Leu Met Arg Cys Gly Gly Cys
                50                  55                  60

Cys Asn Asp Glu Gly Leu Glu Cys Val Pro Thr Glu Ser Asn
                65                  70                  75

Ile Thr Met Gln Ile Met Arg Ile Lys Pro His Gln Gly Gln His
                80                  85                  90

Ile Gly Glu Met Ser Phe Leu Gln His Asn Lys Cys Glu Cys Arg
                95                 100                 105

Pro Lys Lys Asp Arg Ala Arg Gln Glu Asn Pro Cys Gly Pro Cys
               110                 115                 120

Ser Glu Arg Arg Lys His Leu Phe Val Gln Asp Pro Gln Thr Cys
               125                 130                 135

Lys Cys Ser Cys Lys Asn Thr Asp Ser Arg Cys Lys Met
               140                 145

<210> SEQ ID NO 34
<211> LENGTH: 145
<212> TYPE: PRT
<213> ORGANISM: Artificial Sequence
<220> FEATURE:
<221> NAME/KEY: PEPTIDE
<223> OTHER INFORMATION: VEGF145 isoform

<400> SEQUENCE: 34

Ala Pro Met Ala Glu Gly Gly Gly Gln Asn His His Glu Val Val
                 5                  10                  15

Lys Phe Met Asp Val Tyr Gln Arg Ser Tyr Cys His Pro Ile Glu
                20                  25                  30

Thr Leu Val Asp Ile Phe Gln Glu Tyr Pro Asp Glu Ile Glu Tyr
                35                  40                  45

Ile Phe Lys Pro Ser Cys Val Pro Leu Met Arg Cys Gly Gly Cys
                50                  55                  60

Cys Asn Asp Glu Gly Leu Glu Cys Val Pro Thr Glu Ser Asn
                65                  70                  75

Ile Thr Met Gln Ile Met Arg Ile Lys Pro His Gln Gly Gln His
                80                  85                  90

Ile Gly Glu Met Ser Phe Leu Gln His Asn Lys Cys Glu Cys Arg
                95                 100                 105

Pro Lys Lys Asp Arg Ala Arg Gln Glu Lys Lys Ser Val Arg Gly
               110                 115                 120

Lys Gly Lys Gly Gln Lys Arg Lys Arg Lys Lys Ser Arg Tyr Lys
               125                 130                 135

Ser Trp Ser Val Cys Asp Lys Pro Arg Arg
               140                 145

<210> SEQ ID NO 35
<211> LENGTH: 26
<212> TYPE: PRT
<213> ORGANISM: Artificial Sequence
<220> FEATURE:
<221> NAME/KEY: PEPTIDE
<223> OTHER INFORMATION: Signal sequence at 5' end of VEGF isoforms

<400> SEQUENCE: 35

Met Asn Phe Leu Leu Ser Trp Val His Trp Ser Leu Ala Leu Leu
                 5                  10                  15
```

```
Leu Tyr Leu His His Ala Lys Trp Ser Gln Ala
            20                  25
```